(12) United States Patent
Dyckman et al.

(10) Patent No.: US 7,759,343 B2
(45) Date of Patent: Jul. 20, 2010

(54) PYRROLO-TRIAZINE ANILINE COMPOUNDS USEFUL AS KINASE INHIBITORS

(75) Inventors: Alaric Dyckman, Lawrenceville, NJ (US); John Hynes, Washington Crossing, PA (US); Katerina Leftheris, Skillman, NJ (US); Chunjian Liu, Pennington, NJ (US); Stephen T. Wrobleski, Whitehouse Station, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/259,483

(22) Filed: Oct. 28, 2008

(65) Prior Publication Data

US 2009/0105243 A1 Apr. 23, 2009

Related U.S. Application Data

(62) Division of application No. 10/420,399, filed on Apr. 22, 2003, now Pat. No. 7,160,883.

(60) Provisional application No. 60/374,938, filed on Apr. 23, 2002.

(51) Int. Cl.
C07D 487/04 (2006.01)
C07D 403/12 (2006.01)
C07D 413/08 (2006.01)
A61K 31/53 (2006.01)
A61P 9/10 (2006.01)
A61P 19/02 (2006.01)
A61P 19/04 (2006.01)
A61P 35/00 (2006.01)

(52) U.S. Cl. ..................... 514/243; 544/183
(58) Field of Classification Search ............ 544/183; 514/243
See application file for complete search history.

(56) References Cited

U.S. PATENT DOCUMENTS

| | | | |
|---|---|---|---|
| 6,147,080 A | 11/2000 | Bemis et al. | |
| 6,251,914 B1 | 6/2001 | Adams et al. | |
| 6,277,989 B1 | 8/2001 | Chakravarty et al. | |
| 6,670,357 B2 | 12/2003 | Leftheris et al. | |
| 6,867,300 B2 * | 3/2005 | Godfrey et al. | 544/183 |
| 6,982,265 B1 | 1/2006 | Hunt et al. | |
| 7,034,151 B2 | 4/2006 | Chen et al. | |
| 7,160,883 B2 * | 1/2007 | Dyckman et al. | 514/243 |
| 7,211,666 B2 * | 5/2007 | Godfrey et al. | 544/183 |
| 7,462,616 B2 * | 12/2008 | Dyckman et al. | 514/243 |
| 2002/0065270 A1 | 5/2002 | Moriarty et al. | |
| 2002/0137747 A1 | 9/2002 | Moriarty et al. | |
| 2003/0139435 A1 | 7/2003 | Ahmed et al. | |
| 2003/0186982 A1 | 10/2003 | Godfrey et al. | |
| 2003/0186983 A1 | 10/2003 | Mastalerz et al. | |
| 2004/0023992 A1 | 2/2004 | Das et al. | |
| 2004/0063707 A1 | 4/2004 | Bhide et al. | |
| 2004/0063708 A1 | 4/2004 | Bhide et al. | |
| 2004/0072832 A1 | 4/2004 | Bhide et al. | |
| 2004/0077858 A1 | 4/2004 | Bhide et al. | |
| 2004/0142931 A1 | 7/2004 | Vite et al. | |
| 2006/0003967 A1 | 1/2006 | Shi et al. | |
| 2006/0030708 A1 | 2/2006 | Lobben | |
| 2006/0229449 A1 | 10/2006 | Bhattacharya et al. | |
| 2006/0235020 A1 | 10/2006 | Kim et al. | |
| 2007/0213300 A1 | 9/2007 | Liu et al. | |

FOREIGN PATENT DOCUMENTS

| | | |
|---|---|---|
| WO | WO00/20402 | 4/2000 |
| WO | WO 00/56738 | 9/2000 |
| WO | WO 00/71129 | 11/2000 |
| WO | WO 01/14378 | 3/2001 |
| WO | WO 01/27089 | 4/2001 |
| WO | WO 01/34605 | 5/2001 |
| WO | WO02/40486 A2 | 5/2002 |
| WO | WO03/091229 | 11/2003 |
| WO | WO2004/043912 | 5/2004 |

OTHER PUBLICATIONS

Wolft Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, p. 596.*
West, Anthony R., Solid State Chemistry and its Applications, Wiley, New York, 1988, pp. 358 & 365.*
Vippagunta et al., Advanced Drug Delivery Reviews 48: 3-26, 2001.*
Henry et al., Drugs. Fut., vol. 24, pp. 1345-1354 (1999).
Rankin et al., Br. J. Rheumatol., vol. 34, pp. 334-342 (1995).
Moreland et al., Ann. Intern.Med., vol. 130, pp. 478-486 (1999).
Branger, J., et al., "Anti-Inflammatory Effects of a p38 Mitogen-Activated Protein Kinase Inhibitor During Human Endotoxemia", The Journal of Immunology, vol. 168, pp. 4070-4077, (2002).

(Continued)

Primary Examiner—Venkataraman Balasubramanian
(74) Attorney, Agent, or Firm—Laurelee A. Duncan

(57) ABSTRACT

Compounds having the formula (I),

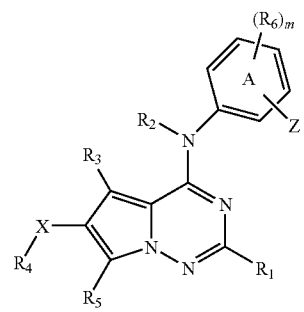

and pharmaceutically acceptable salts, prodrugs, and solvates thereof, are useful as kinase inhibitors, wherein $R_1$, $R_2$, $R_3$, $R_4$, $R_5$, $R_6$, X and Z are as described in the specification.

12 Claims, No Drawings

OTHER PUBLICATIONS

Davis, J. C., Jr., "Understanding the Role of Tumor Necrosis Factor Inhibition in Ankylosing Spondylitis", Seminars in Arthritis and Rheumatism, vol. 34, pp. 668-677, (2004).

Gottlieb, A. B., et al., TNF Inhibition Rapidly Down-Regulates Multiple Proinflammatory Pathways in Psoriasis Plaques[1], The Journal of Immunology, vol. 175, pp. 2721-2729, (2005).

Hideshima, T. et al, "Targeting p38 MAPK inhibits multiple myeloma cell growth in the bone marrow milieu", Blood, vol. 101(2), pp. 703-706, (2003).

Johansen, C., et al., "Protein Expression of TNF-α in Psoriatic Skin Is Regulated at a Posttranscriptional Level by MAPK-Activated Protein Kinase 2[1]", The Journal of Immunology, vol. 176, pp. 1431-1438, (2006).

Johansen, C., et al., "The mitogen-activated protein kinases p38 and KRK1/2 are increased in lesional psoriatic skin", British Journal of Dermatology, vol. 152, pp. 37-42, (2005).

Kumar, S., et al., "P38 MAP Kinases: Key Signalling Molecules as Therapeutic Targets for Inflammatory Diseases", vol. 2, pp. 717-726, (2003).

Mease, P. J., et al., "Psoriatic arthritis treatment: biological response modifiers", Ann. Rheum. Dis., vol. 64 (Suppl. II), pp. ii78-ii82, (2005).

Navas, TA, et al., Inhibition of p38α MAPK enhances proteasome inhibitor-induced apoptosis of myeloma cells by modulating Hsp27, Bcl-$X_L$, MCl-1 and p53 levels in vitro and inhibits tumor growth in vivo, Leukemia, 1-11 (2006).

Papp. K. A., "The long-term efficacy and safety of new biological therapies for psoriasis", Arch. Dermatol. Res. vol. 298, pp. 7-15, (2006).

Saklatvala, J., "The p38 MAP kinase pathway as a therapeutic target in inflammatory disease", Current Opinion in Pharmacology, vol. 4, pp. 372-377, (2004).

Waetzig G. H., "p38 Mitogen-Activated Protein Kinase Is Activated and Linked to TNF-α Signaling in Inflammatory Bowel Disease[1]", The Journal of Immunology, vol. 168, pp. 5342-5351, (2002).

* cited by examiner

PYRROLO-TRIAZINE ANILINE COMPOUNDS USEFUL AS KINASE INHIBITORS

This application claims priority to U.S. Provisional Application Ser. No. 60/374,938 filed Apr. 23, 2002, the entirety of which is incorporated herein by reference.

FIELD OF THE INVENTION

This invention relates to pyrrolotriazine compounds, more particularly, to cycloalkyl, heterocyclo and heteroaryl pyrrolotriazine aniline compounds useful for treating p38 kinase-associated conditions. The invention further pertains to pharmaceutical compositions containing at least one compound according to the invention useful for treating p38 kinase-associated conditions and methods of inhibiting the activity of p38 kinase in a mammal.

BACKGROUND OF THE INVENTION

A large number of cytokines participate in the inflammatory response, including IL-1, IL-6, IL-8 and TNF-α. Overproduction of cytokines such as IL-1 and TNF-α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others [Henry et al., *Drugs Fut.*, 24:1345-1354 (1999); Salituro et al., *Curr. Med. Chem.* 6:807-823 (1999)]. Evidence in human patients indicates that protein antagonists of cytokines are effective in treating chronic inflammatory diseases, such as, for example, monoclonal antibody to TNF-α (Enbrel) [Rankin et al., *Br. J. Rheumatol.*, 34:334-342 (1995)], and soluble TNF-α receptor-Fc fusion protein (Etanercept) [Moreland et al., *Ann. Intern. Med.*, 130:478-486 (1999)].

The biosynthesis of TNF-α occurs in many cell types in response to an external stimulus, such as, for example, a mitogen, an infectious organism, or trauma. Important mediators of TNF-α production are the mitogen-activated protein (MAP) kinases, and in particular, p38 kinase. These kinases are activated in response to various stress stimuli, including but not limited to proinflammatory cytokines, endotoxin, ultraviolet light, and osmotic shock. Activation of p38 requires dual phosphorylation by upstream MAP kinase kinases (MKK3 and MKK6) on threonine and tyrosine within a Thr-Gly-Tyr motif characteristic of p38 isozymes.

There are four known isoforms of p38, i.e., p38-α, p38β, p38γ, and p38δ. The α and β isoforms are expressed in inflammatory cells and are key mediators of TNF-α production. Inhibiting the p38α and β enzymes in cells results in reduced levels of TNF-α expression. Also, administering p38α and β inhibitors in animal models of inflammatory disease has proven that such inhibitors are effective in treating those diseases. Accordingly, the p38 enzymes serve an important role in inflammatory processes mediated by IL-1 and TNF-α. Compounds that reportedly inhibit p38 kinase and cytokines such as IL-1 and TNF-α for use in treating inflammatory diseases are disclosed in U.S. Pat. Nos. 6,277,989 and 6,130,235 to Scios, Inc; U.S. Pat. Nos. 6,147,080 and 5,945,418 to Vertex Pharmaceuticals Inc; U.S. Pat. Nos. 6,251,914, 5,977,103 and 5,658,903 to Smith-Kline Beecham Corp.; U.S. Pat. Nos. 5,932,576 and 6,087,496 to G.D. Searle & Co.; WO 00/56738 and WO 01/27089 to Astra Zeneca; WO 01/34605 to Johnson & Johnson; WO 00/12497 (quinazoline derivatives as p38 kinase inhibitors); WO 00/56738 (pyridine and pyrimidine derivatives for the same purpose); WO 00/12497 (discusses the relationship between p38 kinase inhibitors); and WO 00/12074 (piperazine and piperidine compounds useful as p38 inhibitors).

The present invention provides certain pyrrolotriazine compounds, particularly, pyrrolotriazine aniline compounds useful as kinase inhibitors, particularly kinases p38α and β. Pyrrolotriazine compounds useful as tyrosine kinase inhibitors are disclosed in U.S. patent application Ser. No. 09/573,829, filed May 18, 2000, assigned to the present assignee. Methods of treating p38 kinase-associated conditions as well as pyrrolotriazine compounds useful for that purpose are described in U.S. patent application Ser. No. 10/036,293, assigned to the present assignee and having common inventors herewith, which claims the benefit of U.S. Provisional Application No. 60/249,877, filed Nov. 17, 2000, and U.S. Provisional Application No. 60/310,561, filed Aug. 7, 2001. Pyrrolotriazine compounds substituted with an acidic group reportedly having sPLA$_2$-inhibitory activity are disclosed in WO 01/14378 A1 to Shionogi & Co., Ltd, published Mar. 1, 2001 in Japanese. Each of the patent applications, patents, and publications referred to herein is incorporated herein by reference.

SUMMARY OF THE INVENTION

The instant invention pertains to compounds of formula (I),

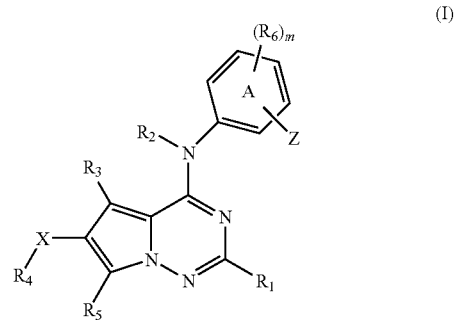

(I)

enantiomers, diastereomers, salts, and solvates thereof, wherein:

X is selected from —O—, —OC(=O)—, —S—, —S(=O)—, —SO$_2$—, —C(=O)—, —CO$_2$—, —NR$_8$—, —NR$_8$C(=O)—, —NR$_8$C(=O)NR$_9$—, —NR$_8$CO$_2$—, —NR$_8$SO$_2$—, —NR$_8$SO$_2$NR$_9$—, —SO$_2$NR$_8$—, —C(=O)NR$_8$—, halogen, nitro, and cyano, or X is absent;

Z is —C(=O)NR$_{10}$—B$^b$, —(CH$_2$)—C(=O)NR$_{10}$—B$^c$, —NR$_{10a}$C(=O)—B$^a$, —(CH$_2$)—NR$_{10a}$C(=O)—B$^c$, —NR$_{10a}$C(=O)NR$_{10}$—B, —NR$_{10}$SO$_2$—B, —SO$_2$NR$_{10}$—B, —C(=O)—B$^a$, —CO$_2$—B$^e$, —OC(=O)—B$^a$, —C(=O)NR$_{10}$—NR$_{10a}$—B$^d$, —NR$_{10}$CO$_2$—B$^a$ or —C(=O)NR$_{10}$—(CH$_2$)C(=O)B$^a$;

B is
(a) optionally-substituted cycloalkyl, optionally-substituted heterocyclo, or optionally substituted heteroaryl; or
(b) aryl substituted with one R$_{11}$ and zero to two R$_{12}$;

B$^a$ is optionally substituted alkyl, optionally-substituted cycloalkyl, optionally-substituted heterocyclo, optionally substituted aryl, or optionally substituted heteroaryl;

B$^b$ is
(a) optionally-substituted cycloalkyl, optionally-substituted heterocyclo, or optionally substituted heteroaryl;

(b) aryl substituted with one $R_{11}$ and zero to two $R_{12}$; or
(c) —C(=O)$R_{13}$, —CO$_2R_{13}$, —C(=O)NR$_{13}R_{13a}$;

$B^c$ is optionally substituted alkyl, optionally substituted alkoxy, optionally-substituted cycloalkyl, optionally-substituted heterocyclo, optionally substituted aryl, or optionally substituted heteroaryl;

$B^d$ is hydrogen, —C(=O)$R_{13}$, or —CO$_2R_{13}$;

$B^e$ is hydrogen, optionally substituted alkyl, optionally-substituted cycloalkyl, optionally-substituted heterocyclo, optionally substituted aryl, or optionally substituted heteroaryl;

$R_1$ and $R_5$ are independently selected from hydrogen, alkyl, substituted alkyl, —OR$_{14}$, —SR$_{14}$, —OC(=O)R$_{14}$, —CO$_2R_{14}$, —C(=O)NR$_{14}R_{14a}$, —NR$_{14}R_{14a}$, —S(=O)R$_{14}$, —SO$_2R_{14}$, —SO$_2$NR$_{14}R_{14a}$, —NR$_{14}$SO$_2$NR$_{14a}R_{14b}$, —NR$_{14a}$SO$_2R_{14}$, —NR$_{14}$C(=O)R$_{14a}$, —NR$_{14}$CO$_2R_{14a}$, —NR$_{14}$C(=O)NR$_{14a}R_{14b}$, halogen, nitro, and cyano;

$R_2$ is hydrogen or $C_{1-4}$alkyl;

$R_3$ is hydrogen, methyl, perfluoromethyl, methoxy, halogen, cyano, $NH_2$, or $NH(CH_3)$;

$R_4$ is selected from:
  a) hydrogen, provided that $R_4$ is not hydrogen if X is —S(=O)—, —SO$_2$—, —NR$_8$CO$_2$—, or —NR$_8$SO$_2$—;
  b) alkyl, alkenyl, and alkynyl optionally independently substituted with keto and/or one to four $R_{17}$;
  c) aryl and heteroaryl either of which may be optionally independently substituted with one to three $R_{16}$; and
  d) heterocyclo and cycloalkyl either of which may be optionally independently substituted with keto and/or one to three $R_{16}$; or
  e) $R_4$ is absent if X is halogen, nitro, or cyano;

$R_6$ is attached to any available carbon atom of phenyl ring A and at each occurrence is independently selected from alkyl, halogen, trifluoromethoxy, trifluoromethyl, hydroxy, alkoxy, alkanoyl, alkanoyloxy, thiol, alkylthio, ureido, nitro, cyano, carboxy, carboxyalkyl, carbamyl, alkoxycarbonyl, alkylthiono, arylthiono, arylsulfonylamine, alkylsulfonylamine, sulfonic acid, alkysulfonyl, sulfonamido, phenyl, benzyl, aryloxy, and benzyloxy, wherein each $R_6$ group in turn may be further substituted by one to two $R_{18}$;

$R_8$ and $R_9$ are independently selected from hydrogen, alkyl, substituted alkyl, aryl, cycloalkyl, heterocyclo, and heteroaryl;

$R_{10}$ and $R_{10a}$ are independently selected from hydrogen, alkyl, substituted alkyl, alkoxy, and aryl;

$R_{11}$ is selected from
  (a) alkyl, haloalkyl, alkoxy, haloalkoxy, —SO$_2$alkyl, cycloalkyl, heterocyclo, and heteroaryl any of which may be optionally substituted; or
  (b) halo, cyano, amino, alkylamino, and dialkylamino;

$R_{12}$ is selected from alkyl, $R_{17}$, and $C_{1-4}$alkyl substituted with keto (=O) and/or one to three $R_{17}$;

$R_{13}$ and $R_{13a}$ are independently selected from hydrogen, optionally substituted alkyl, optionally substituted cycloalkyl and optionally substituted aryl;

$R_{14}$, $R_{14a}$ and $R_{14b}$ are independently selected from hydrogen, alkyl, substituted alkyl, aryl, cycloalkyl, heterocyclo, and heteroaryl, except when $R_{14}$ is joined to a sulphonyl group as in —S(=O)R$_{14}$, —SO$_2R_{14}$, and —NR$_{14a}$SO$_2R_{14}$, then $R_{14}$ is not hydrogen;

$R_{16}$ is selected from alkyl, $R_{17}$, and $C_{1-4}$alkyl substituted with keto (=O) and/or one to three $R_{17}$;

$R_{17}$ is selected from
  (a) halogen, haloalkyl, haloalkoxy, nitro, cyano, —SR$_{23}$, —OR$_{23}$, —NR$_{23}R_{24}$, —NR$_{23}$SO$_2R_{25}$, —SO$_2R_{25}$, —SO$_2$NR$_{23}R_{24}$, —CO$_2R_{23}$, —C(=O)R$_{23}$, —C(=O)NR$_{23}R_{24}$, —OC(=O)R$_{23}$, —OC(=O)NR$_{23}R_{24}$, —NR$_{23}$C(=O)R$_{24}$, —NR$_{23}$CO$_2R_{24}$;
  (b) aryl or heteroaryl either of which may be optionally substituted with one to three $R_{26}$; or
  (c) cycloalkyl or heterocyclo optionally substituted with keto (=O) and/or one to three $R_{26}$;

$R_{18}$ and $R_{26}$ are independently selected from $C_{1-6}$alkyl, $C_{2-6}$alkenyl, halogen, haloalkyl, haloalkoxy, cyano, nitro, amino, $C_{1-4}$alkylamino, amino$C_{1-4}$alkyl, hydroxy, hydroxy$C_{1-4}$alkyl, alkoxy, $C_{1-4}$alkylthio, aryl, heterocyclo, (aryl)alkyl, aryloxy, and (aryl)alkoxy;

$R_{23}$ and $R_{24}$ are each independently selected from hydrogen, alkyl, alkenyl, substituted alkyl, substituted alkenyl, aryl, cycloalkyl, heteroaryl, and heterocyclo;

$R_{25}$ is selected from alkyl, substituted alkyl, aryl, heteroaryl, cycloalkyl and heterocyclo; and m is 0, 1, 2 or 3.

The invention further pertains to pharmaceutical compositions containing compounds of formula (I), and to methods of treating conditions associated with the activity of p38 kinase (α and β), comprising administering to a mammal a pharmaceutically-acceptable amount of a compound of formula (I).

DESCRIPTION OF THE INVENTION

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms. When a subscript is used with reference to an alkyl or other group, the subscript refers to the number of carbon atoms that the group may contain. For example, the term "$C_{0-4}$alkyl" includes a bond and alkyl groups of 1 to 4 carbon atoms.

The term "substituted alkyl" refers to an alkyl group substituted by one to four substituents selected from halogen, hydroxy, alkoxy, keto (=O), alkanoyl, aryloxy, alkanoyloxy, NR$_a$R$_b$, alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, —SO$_2$NR$_a$R$_b$, nitro, cyano, —CO$_2$H, —CONR$_a$R$_b$, alkoxycarbonyl, aryl, guanidino and heteroaryls or heterocyclos (such as indolyl, imidazolyl, furyl, thienyl, thiazolyl, pyrrolidyl, pyridyl, pyrimidyl and the like), wherein $R_a$ and $R_b$ are selected from hydrogen, alkyl, aryl, aralkyl, cycloalkyl, cycloalkylalkyl, heteroaryl, heteroarylalkyl, heterocycle, and heterocyclealkyl. The substituent on the alkyl optionally in turn may be further substituted, in which case it will be with substituted one or more of $C_{1-4}$alkyl, $C_{2-4}$alkenyl, halogen, haloalkyl, haloalkoxy, cyano, nitro, amino, $C_{1-4}$alkylamino, amino$C_{1-4}$alkyl, hydroxy, hydroxy$C_{1-4}$alkyl, alkoxy, alkylthio, phenyl, benzyl, phenyloxy, and/or benzyloxy.

The term "alkenyl" refers to straight or branched chain hydrocarbon groups of 2 to 20 carbon atoms, preferably 2 to 15 carbon atoms, and most preferably 2 to 8 carbon atoms, having at least one double bond, and depending on the number of carbon atoms, up to four double bonds.

The term "substituted alkenyl" refers to an alkenyl group substituted by one to two substituents selected from those recited above for substituted alkyl groups.

The term "alkynyl" refers to straight or branched chain hydrocarbon groups of 2 to 20 carbon atoms, preferably 2 to 15 carbon atoms, and most preferably 2 to 8 carbon atoms, having at least one triple bond, and depending on the number of carbon atoms, up to four triple bonds.

The term "substituted alkynyl" refers to an alkynyl group substituted by one to two substituents selected from those recited above for alkyl groups.

When the term alkyl is used in connection with another group, as in heterocycloalkyl or cycloalkylalkyl, this means the identified (first named) group is bonded directly through an alkyl group which may be branched or straight chain (e.g., cyclopropyl$C_{1-4}$alkyl means a cyclopropyl group bonded through a straight or branched chain alkyl group having one to four carbon atoms.). In the case of substituents, as in "substituted cycloalkylalkyl," the alkyl portion of the group, besides being branched or straight chain, may be substituted as recited above for substituted alkyl groups and/or the first named group (e.g., cycloalkyl) may be substituted as recited herein for that group.

The term "halogen" or "halo" refers to fluorine, chlorine, bromine and iodine.

The term "aryl" refers to monocyclic or bicyclic aromatic substituted or unsubstituted hydrocarbon groups having 6 to 12 carbon atoms in the ring portion, such as phenyl, naphthyl, and biphenyl groups.) Aryl groups may optionally include one to three additional rings (either cycloalkyl, heterocyclo or heteroaryl) fused thereto.

Examples include:

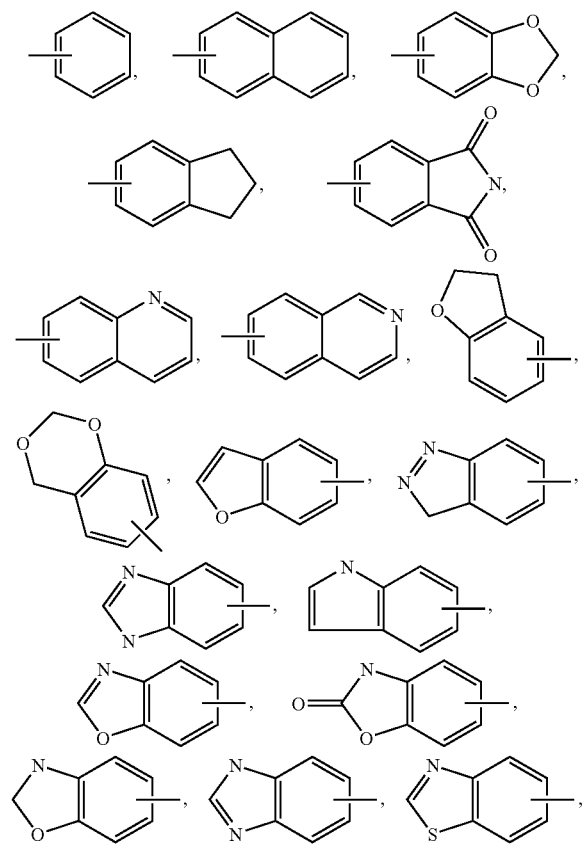

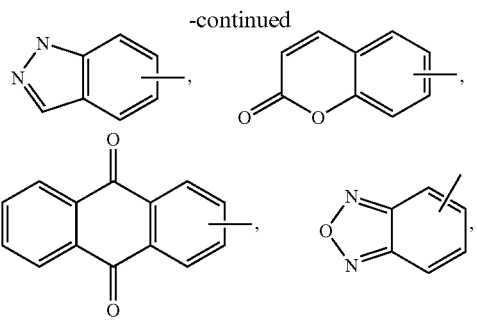

and the like. Each ring of the aryl may be optionally substituted with one to three $R_c$, groups, wherein $R_c$ at each occurrence is selected from alkyl, substituted alkyl, halogen, trifluoromethoxy, trifluoromethyl, —SR, —OR, —NRR', —NRSO$_2$R', —SO$_2$R, —SO$_2$NRR', —CO$_2$R', —C(=O)R', —C(=O)NRR', —OC(=O)R', —OC(=O)NRR', —NRC(=O)R', —NRCO$_2$R', phenyl, $C_{3-7}$ cycloalkyl, and five-to-six membered heterocyclo or heteroaryl, wherein each R and R' is selected from hydrogen, alkyl, substituted alkyl, alkenyl, substituted alkenyl, phenyl, $C_{3-7}$cycloalkyl, and five-to-six membered heterocyclo or heteroaryl, except in the case of a sulfonyl group, then R is not going to be hydrogen. Each substituent $R_c$ optionally in turn may be further substituted by one or more (preferably 0 to 2) $R_d$ groups, wherein $R_d$ is selected from $C_{1-6}$alkyl, $C_{2-6}$alkenyl, halogen, haloalkyl, haloalkoxy, cyano, nitro, amino, $C_{1-4}$ alkylamino, amino$C_{1-4}$alkyl, hydroxy, hydroxy$C_{1-4}$alkyl, alkoxy, alkylthio, phenyl, benzyl, phenylethyl, phenyloxy, and benzyloxy.

The term "aralkyl" refers to an aryl group bonded directly through an alkyl group, such as benzyl, wherein the alkyl group may be branched or straight chain. In the case of a "substituted aralkyl," the alkyl portion of the group besides being branched or straight chain, may be substituted as recited above for substituted alkyl groups and/or the aryl portion may be substituted as recited herein for aryl. Thus, the term "optionally substituted benzyl" refers to the group

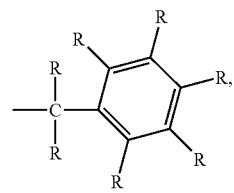

wherein each R group may be hydrogen or may also be selected from $R_c$ as defined above, in turn optionally substituted with one or more $R_d$. At least two of these "R" groups should be hydrogen and preferably at least five of the "R" groups is hydrogen. A preferred benzyl group involves the alkyl-portion being branched to define

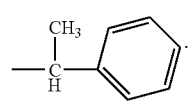

The term "heteroaryl" refers to a substituted or unsubstituted aromatic group for example, which is a 4 to 7 membered monocyclic, 7 to 11 membered bicyclic, or 5 to 15 membered tricyclic ring system, which has at least one heteroatom and at least one carbon atom-containing ring. Each ring of the heteroaryl group containing a heteroatom can contain one or two oxygen or sulfur atoms and/or from one to four nitrogen atoms, provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or nonaromatic. The heteroaryl group may be attached at any available nitrogen or carbon atom of any ring. It may optionally be substituted with one to three (preferably 0 to 2) $R_c$ groups, as defined above for aryl, which in turn may be substituted with one or more (preferably 0 to 2) $R_d$ groups, also as recited above.

Exemplary monocyclic heteroaryl groups include pyrrolyl, pyrazolyl, pyrazolinyl, imidazolyl, oxazolyl, isoxazolyl, thiazolyl (i.e.,

), thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrolinyl, acridinyl, phenanthridinyl, xanthenyl and the like.

The term "cycloalkyl" refers to a saturated or partially unsaturated non-aromatic cyclic hydrocarbon ring system, preferably containing 1 to 3 rings and 3 to 7 carbon atoms per ring, which may be substituted or unsubstituted and/or which may be fused with a $C_3$-$C_7$ carbocylic ring, a heterocyclic ring, or which may have a bridge of 3 to 4 carbon atoms. The cycloalkyl groups including any available carbon or nitrogen atoms on any fused or bridged rings optionally may have 0 to 3 (preferably 0-2) substituents selected from R, groups, as recited above, and/or from keto (where appropriate) which in turn may be substituted with one to three $R_d$ groups, also as recited above. Thus, when it is stated that a carbon-carbon bridge may be optionally substituted, it is meant that the carbon atoms in the bridged ring optionally may be substituted with an $R_c$ group, which preferably is selected from $C_{1-4}$alkyl, $C_{2-4}$alkenyl, halogen, haloalkyl, haloalkoxy, cyano, amino, $C_{1-4}$alkylamino, amino$C_{1-4}$alkyl, hydroxy, hydroxy$C_{1-4}$alkyl, and $C_{1-4}$alkoxy. Exemplary cycloalkyl groups include cyclopropyl, cyclobutyl, cyclopentyl, cyclohexyl, cycloheptyl, bicycloheptane, cyclooctyl, cyclodecyl, cyclododecyl, and adamantyl.

The terms "heterocycle", "heterocyclic" and "heterocyclo" each refer to a fully saturated or partially unsaturated nonaromatic cyclic group, which may be substituted or unsubstituted, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen, oxygen, and sulfur atoms, where the nitrogen and sulfur heteroatoms also optionally may be oxidized and the nitrogen heteroatoms also optionally may be quaternized. Preferably two adjacent heteroatoms are not simultaneously selected from oxygen and nitrogen. The heterocyclic group may be attached at any nitrogen or carbon atom. The heterocyclo groups optionally may have 0 to 3 (preferably 0-2) substituents selected from keto (=O), and/or one or more $R_c$ groups, as recited above, which in turn may be substituted with one to three $R_d$ groups, also as recited above.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic hetrocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Also included are smaller heterocyclos, such as epoxides and aziridines.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., indolyl), the reference is intended to include rings having 0 to 3, preferably 0-2, substituents selected from those recited above for the aryl, cycloalkyl, heterocyclo and/or heteroaryl groups, as appropriate. Additionally, when reference is made to a specific heteroaryl or heterocyclo group, the reference is intended to include those systems having the maximum number of non-cumulative double bonds or less than the maximum number of double bonds. Thus, for example, the term "isoquinoline" refers to isoquinoline and tetrahydroisoquinoline.

Additionally, it should be understood that one skilled in the field may make appropriate selections for the substituents for the aryl, cycloalkyl, heterocyclo, and heteroaryl groups to provide stable compounds and compounds useful as pharmaceutically-acceptable compounds and/or intermediate compounds useful in making pharmaceutically-acceptable compounds. Thus, for example, in compounds of formula (I), when B is a cyclopropyl ring, preferably the ring has no more than two substituents, and preferably said substituents do not comprise nitro ($NO_2$), more than one cyano group, or three halogen groups. Similarly, when m is 3, preferably $R_6$, the substituents on the phenyl ring A, are not all nitro, and so forth.

The term "heteroatoms" shall include oxygen, sulfur and nitrogen.

The term "haloalkyl" means an alkyl having one or more halo substituents.

The term "perfluoromethyl" means a methyl group substituted by one, two, or three fluoro atoms, i.e., $CH_2F$, $CHF_2$ and $CF_3$. The term "perfluoroalkyl" means an alkyl group having from one to five fluoro atoms, such as pentafluoroethyl.

The term "haloalkoxy" means an alkoxy group having one or more halo substituents. For example, "haloalkoxy" includes —$OCF_3$.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Definitions for the various other groups that are recited above in connection with substituted alkyl, substituted alkenyl, aryl, cycloalkyl, and so forth, are as follows: alkoxy is —$OR^e$, alkanoyl is —$C(=O)R^e$, aryloxy is —OAr, alkanoyloxy is —$OC(=O)R^e$, amino is —$NH_2$, alkylamino is —$NHR^e$ or —$N(R^e)_2$, arylamino is —NHAr or —$NR^eAr$, aralkylamino is —NH—$R^f$—Ar, alkanoylamino is —NH—$C(=O)R^e$, aroylamino is —NH—$C(=O)Ar$, aralkanoylamino is —NH—$C(=O)R$—Ar, thiol is —SH, alkylthio is —$SR^e$, arylthio is —SAr, aralkylthio is —S—$R^f$—Ar, alkylthiono is —$S(=O)R^e$, arylthiono is —$S(=O)Ar$, aralkylthiono is —$S(=O)R^f$—Ar, alkylsulfonyl is —$SO_{(q)}R^e$, arylsulfonyl is —$SO_{(q)}Ar$, arylsulfonylamine is —$NHSO_{(q)}Ar$, alkylsulfonylamine is —$NHSO_2R^e$, aralkylsulfonyl is —$SO_{(q)}R^fAr$, sulfonamido is —$SO_2NH_2$, substituted sulfonamide is —$SO_2NHR^e$ or —$SO_2N(R^e)_2$, nitro is —$NO_2$, carboxy is —$CO_2H$, carbamyl is —$CONH_2$, substituted carbamyl is —$C(=O)NHR^g$ or —$C(=O)NR^gR^h$, alkoxycarbonyl is —$C(=O)OR^e$ carboxyalkyl is —$R^f$—$CO_2H$, sulfonic acid is —$SO_3H$, guanidino is

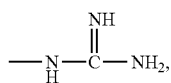

and ureido is

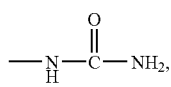

wherein $R^e$ is alkyl or substituted alkyl as defined above, $R^f$ is alkylene or substituted alkylene as defined above, $R^g$ and $R^h$ are selected from alkyl, substituted alkyl, aryl, aralkyl, cycloalkyl, heterocyclo, and heteroaryl; Ar is an aryl as defined above, and q is 2 or 3.

Throughout the specification, groups and substituents thereof may be chosen by one skilled in the field to provide stable moieties and compounds.

The compounds of the present invention may form salts which are also within the scope of this invention. Pharmaceutically acceptable (i.e. non-toxic, physiologically acceptable) salts are preferred, although other salts are also useful, e.g. in isolating or purifying the compounds of this invention.

The compounds of the present invention may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds of the present invention may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art. Salt forms of the compounds may be advantageous for improving the compound dissolution rate and oral bioavailability.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the present invention may also have prodrug forms. Any compound that will be converted in vivo to provide the bioactive agent (i.e., the compound for formula I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 42, p. 309-396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113-191 (1991); and c) H. Bundgaard, *Advanced Drug Delivery Reviews*, 8, 1-38 (1992), each of which is incorporated herein by reference.

It should further be understood that solvates (e.g., hydrates) of the compounds of Formula (I) are also with the scope of the present invention. Methods of solvation are generally known in the art.

Preferred compounds of formula (I) include compounds having the structure:

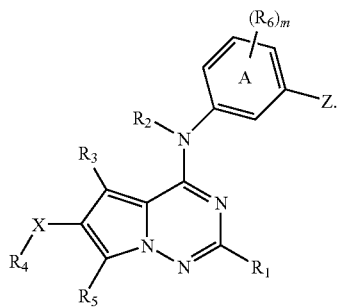

Preferred compounds include those having the structure of formula (I*),

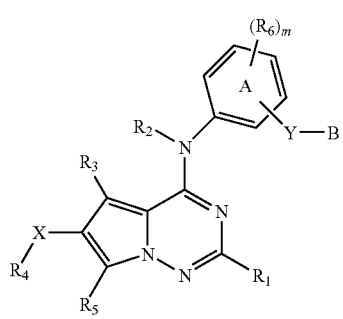

enantiomers, diastereomers, salts and solvates thereof, wherein:

X is selected from —O—, —OC(=O)—, —S—, —S(=O)—, —SO$_2$—, —C(=O)—, —CO$_2$—, —NR$_8$—, —NR$_8$C(=O)—, —NR$_8$C(=O)NR$_9$—, —NR$_8$CO$_2$—, —NR$_8$SO$_2$—, —NR$_8$SO$_2$NR$_9$—, —SO$_2$NR$_8$—, —C(=O)NR$_8$—, halogen, nitro, and cyano, or X is absent;

Y is —C(=O)NR$_{10}$—, —NR$_{10a}$C(=O)NR$_{10}$—, —NR$_{10}$SO$_2$—, —SO$_2$NR$_{10}$—, —C(=O)—, —CO$_2$— or —OC(=O)—;

B is optionally-substituted cycloalkyl, heterocyclo, or heteroaryl; or aryl substituted with one R$_{11}$ and zero to two R$_{12}$; or when Y is —C(=O)NR$_{10}$—, B also may be selected from —C(=O)R$_{13}$, —CO$_2$R$_{13}$, —C(=O)NR$_{13}$R$_{13a}$;

R$_1$ and R$_5$ are independently selected from hydrogen, alkyl, substituted alkyl, —OR$_{14}$, —SR$_{14}$, —OC(=O)R$_{14}$, —CO$_2$R$_{14}$, —C(=O)NR$_{14}$R$_{14a}$, —NR$_{14}$R$_{14a}$, —S(=O)R$_{14}$, —SO$_2$R$_{14}$, —SO$_2$NR$_{14}$R$_{14a}$, —NR$_{14}$SO$_2$NR$_{14a}$R$_{14b}$, —NR$_{14a}$SO$_2$R$_{14}$, —NR$_{14}$C(=O)R$_{14a}$, —NR$_{14}$CO$_2$R$_{14a}$, —NR$_{14}$C(=O)NR$_{14a}$R$_{14b}$, halogen, nitro, and cyano;

R$_2$ is hydrogen or C$_{1-4}$alkyl;

R$_3$ is hydrogen, methyl, perfluoromethyl, methoxy, halogen, cyano, NH$_2$, or NH(CH$_3$);

R$_4$ is selected from:
b) hydrogen, provided that R$_4$ is not hydrogen if X is —S(=O)—, —SO$_2$—, —NR$_8$CO$_2$—, or —NR$_8$SO$_2$—;
b) alkyl, alkenyl, and alkynyl optionally substituted with keto and/or one to four R$_{17}$;
f) aryl and heteroaryl optionally substituted with one to three R$_{16}$; and
g) heterocyclo and cycloalkyl optionally substituted with keto and/or one to three R$_{16}$; or
h) R$_4$ is absent if X is halogen, nitro, or cyano;

R$_6$ is attached to any available carbon atom of phenyl ring A and at each occurrence is independently selected from alkyl, halogen, trifluoromethoxy, trifluoromethyl, hydroxy, alkoxy, alkanoyl, alkanoyloxy, thiol, alkylthio, ureido, nitro, cyano, carboxy, carboxyalkyl, carbamyl, alkoxycarbonyl, alkylthiono, arylthiono, arylsulfonylamine, alkylsulfonylamine, sulfonic acid, alkysulfonyl, sulfonamido, phenyl, benzyl, aryloxy, and benzyloxy, wherein each R$_6$ group in turn may be further substituted by one to two R$_{18}$;

R$_8$ and R$_9$ are independently selected from hydrogen, alkyl, substituted alkyl, aryl, cycloalkyl, heterocyclo, and heteroaryl;

R$_{10}$ and R$_{10a}$ are independently selected from hydrogen, alkyl, substituted alkyl, alkoxy, and aryl;

R$_{11}$ is selected from optionally-substituted cycloalkyl, heterocyclo, and heteroaryl;

R$_{12}$ is selected from alkyl, R$_{17}$, and C$_{1-4}$alkyl substituted with keto (=O) and/or one to three R$_{17}$;

R$_{13}$ and R$_{13a}$ are selected from hydrogen, alkyl, and substituted alkyl;

R$_{14}$, R$_{14a}$ and R$_{14b}$ are independently selected from hydrogen, alkyl, substituted alkyl, aryl, cycloalkyl, heterocyclo, and heteroaryl, except when R$_{14}$ is joined to a sulphonyl group as in —S(=O)R$_{14}$, —SO$_2$R$_{14}$, and —NR$_{14a}$SO$_2$R$_{14}$, then R$_{14}$ is not hydrogen;

R$_{16}$ is selected from alkyl, R$_{17}$, and C$_{1-4}$alkyl substituted with keto (=O) and/or one to three R$_{17}$;

R$_{17}$ is selected from halogen, haloalkyl, haloalkoxy, nitro, cyano, —SR$_{23}$, —OR$_{23}$, —NR$_{23}$R$_{24}$, —NR$_{23}$SO$_2$R$_{25}$, —SO$_2$R$_{25}$, —SO$_2$NR$_{23}$R$_{24}$, —CO$_2$R$_{23}$, —C(=O)R$_{23}$, —C(=O)NR$_{23}$R$_{24}$, —OC(=O)R$_{23}$, —OC(=O) NR$_{23}$R$_{24}$, —NR$_{23}$C(=O)R$_{24}$, —NR$_{23}$CO$_2$R$_{24}$, aryl or heteroaryl optionally substituted with one to three R$_{26}$; or cycloalkyl or heterocyclo optionally substituted with keto (=O) and/or one to three R$_{26}$;

R$_{18}$ and R$_{26}$ are independently selected from C$_{1-6}$alkyl, C$_{2-6}$alkenyl, halogen, haloalkyl, haloalkoxy, cyano, nitro, amino, C$_{1-4}$alkylamino, aminoC$_{1-4}$alkyl, hydroxy, hydroxyC$_{1-4}$alkyl, alkoxy, C$_{1-4}$alkylthio, phenyl, benzyl, phenyloxy, and benzyloxy;

R$_{23}$ and R$_{24}$ are each independently selected from hydrogen, alkyl, alkenyl, substituted alkyl, substituted alkenyl, aryl, cycloalkyl, heteroaryl, and heterocyclo;

R$_{25}$ is selected from alkyl, substituted alkyl, aryl, heteroaryl, cycloalkyl and heterocyclo; and m is 0, 1, 2 or 3.

Preferred compounds of formula (I*) are those having formula (Ia),

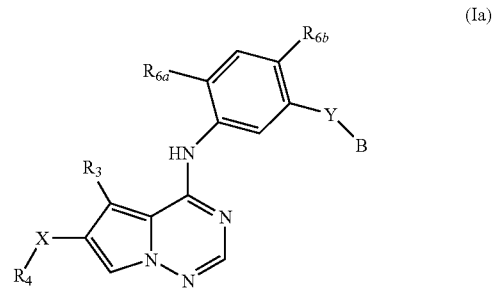

and pharmaceutically-acceptable salts, prodrugs, and solvates thereof, wherein:

$R_3$ is methyl, —$CF_3$, or —$OCF_3$;

X is —C(=O)—, —$NR_8$C(=O)—, or —C(=O)$NR_8$—, wherein $R_8$ is hydrogen or $C_{1-4}$alkyl;

Y is —C(=O)NH—, —NHC(=O)NH—, —NHC(=O)— or —$NHSO_2$—;

B is an optionally-substituted monocyclic or bicyclic cycloalkyl, heteroaryl, or heterocycle, aryl substituted with at least one $R_{11}$ and zero to two $R_{12}$, or when Y is —C(=O)NH—, B also may be selected from —C(=O)$R_{13}$, —$CO_2R_{13}$, and —C(=O)$NR_{13}R_{13a}$;

$R_4$ is hydrogen, $C_{2-6}$alkyl, $C_{1-4}$alkyl optionally substituted with one to three $R_{17}$, aryl or heteroaryl optionally substituted with one to three $R_{16}$, or cycloalkyl or heterocycle optionally-substituted with keto (=O) and/or one to three $R_{16}$;

$R_{6a}$ and $R_{6b}$ are independently selected from hydrogen, $C_{1-6}$alkyl, substituted $C_{1-4}$alkyl, halogen, trifluoromethoxy, trifluoromethyl, —$OR_{27}$, —C(=O)alkyl, —OC(=O)alkyl, —$NR_{27}R_{28}$, —$SR_{27}$, —$NO_2$, —CN, —$CO_2R_{27}$, —$CONH_2$, —$SO_3H$, —S(=O)alkyl, —S(=O)aryl, —$NHSO_2$-aryl-$R_{27}$, —$SO_2NHR_{27}$, —$CONHR_{27}$, and —NHC(=O)$NHR_{27}$;

$R_{11}$ is cycloalkyl, heterocyclo, or heteroaryl optionally substituted with one to two $R_{16}$;

$R_{13}$ and $R_{13a}$ are hydrogen, alkyl or substituted alkyl;

$R_{12}$ and $R_{16}$ are independently selected from $C_{1-4}$alkyl, $R_{17}$, and $C_{1-4}$alkyl substituted with keto and/or one to two $R_{17}$;

$R_{17}$ is selected from halogen, hydroxy, $C_{1-4}$alkoxy, trifluoromethyl, trifluoromethoxy, cyano, nitro, phenyl, benzyl, phenyloxy, benzyloxy, $NH_2$, NH($C_{1-4}$alkyl), N($C_{1-4}$alkyl)$_2$, $C_{3-7}$cycloalkyl, and five or six membered heteroaryl or heterocycle; and $R_{27}$ and $R_{28}$ are selected from hydrogen, $C_{1-4}$alkyl, phenyl, $C_{3-7}$cycloalkyl, and five-to-six membered heterocyclo or heteroaryl.

More preferred are compounds having the formula (Ia), as recited above, wherein:

$R_3$ is methyl, —$CF_3$, or —$OCF_3$;

X is —C(=O)—, —C(=O)NH— or —C(=O)N($C_{1-4}$alkyl)-;

Y is —C(=O)NH—;

B is a $C_{3-7}$cycloalkyl optionally substituted with one to two $R_7$, a five membered heteroaryl optionally substituted with one to two $R_7$, a five or six membered heterocyclo optionally substituted with one to two $R_7$, aryl substituted with at least one $R_{11}$ and optionally substituted with zero to two $R_{12}$, or when Y is —C(=O)NH—, B may also be selected from —C(=O)(alkyl), —$CO_2$(alkyl), and —C(=O)NH(alkyl);

$R_4$ is hydrogen, $C_{2-6}$alkyl, $C_{1-4}$alkyl optionally substituted with one to three $R_{17}$, aryl or heteroaryl optionally substituted with one to three $R_{16}$, or cycloalkyl or heterocycle optionally-substituted with keto (=O), and/or one to three $R_{16}$;

$R_{6a}$ and $R_{6b}$ are independently selected from hydrogen, $C_{1-4}$alkyl, halogen, trifluoromethoxy, trifluoromethyl, hydroxy, $C_{1-4}$alkoxy, cyano, $NH_2$, NH($C_{1-4}$ alkyl), and N($C_{1-4}$alkyl)$_2$;

$R_7$ is selected from $C_{1-6}$alkyl, substituted $C_{1-4}$alkyl, halogen, trifluoromethoxy, trifluoromethyl, cyano, —$SR_{20}$, —$OR_{20}$, —$NR_2OR_{21}$, —$NR_{20}SO_2R_{21}$, —$SO_2R_{19}$, —$SO_2NR_2OR_{21}$, —$CO_2R_{20}$, —C(=O)$R_{20}$, —C(=O)$NR_2OR_{21}$, —OC(=O)$R_{20}$, —OC(=O)$NR_2OR_{21}$, —$NR_{20}$C(=O)$R_{21}$, —$NR_{20}CO_2R_{21}$, phenyl, benzyl, $C_{3-7}$cycloalkyl, and five-to-six membered heterocyclo or heteroaryl;

$R_{11}$ is cycloalkyl, heterocyclo, or heteroaryl optionally substituted with one to two $R_{16}$;

$R_{13}$ and $R_{13a}$ are hydrogen, alkyl or substituted alkyl;

$R_{12}$ and $R_{16}$ are independently selected from $C_{1-4}$alkyl, $R_{17}$, and $C_{1-4}$alkyl substituted with keto and/or one to two $R_{17}$;

$R_{17}$ is selected from halogen, hydroxy, $C_{1-4}$alkoxy, trifluoromethyl, trifluoromethoxy, cyano, nitro, phenyl, benzyl, phenyloxy, benzyloxy, $NH_2$, NH($C_{1-4}$alkyl), N($C_{1-4}$alkyl)$_2$, $C_{3-7}$cycloalkyl, and five or six membered heteroaryl or heterocycle;

$R_{19}$ is $C_{1-4}$alkyl, phenyl, $C_{3-7}$cycloalkyl, or five-to-six membered heterocyclo or heteroaryl;

$R_{20}$ and $R_{21}$ are selected from hydrogen, $C_{1-4}$alkyl, phenyl, $C_{3-7}$cycloalkyl, and five-to-six membered heterocyclo or heteroaryl; and $R_{27}$ and $R_{28}$ are selected from hydrogen, $C_{1-4}$alkyl, phenyl, $C_{3-7}$cycloalkyl, and five-to-six membered heterocyclo or heteroaryl.

In compounds of formula (I), preferably $R_3$ is methyl, —$CF_3$, or —$OCF_3$, more preferably methyl; X preferably is —C(=O)— or —C(=O)NH—; and Y is preferably —C(=O)NH—. Preferably when X is —C(=O)NH—, $R_4$ is $C_{2-6}$alkyl or substituted $C_{1-4}$alkyl, more preferably $C_{1-4}$alkyl or optionally-substituted benzyl. When X is —C(=O)—, preferably $R_4$ is an optionally-substituted aryl or heteroaryl.

When $R_4$ is a heterocyclo, advantageously it is selected from diazepinyl, morpholinyl, piperidinyl, and pyrrolidinyl, said heterocycle being optionally substituted with one to two of $C_{1-4}$alkyl, hydroxy, $C_{1-4}$alkoxy, phenyl, and/or benzyl. When X is —C(=O)— and $R_4$ is aryl or heteroaryl, preferably $R_4$ is phenyl, pyridinyl, pyrimidinyl, or pyrazinyl, optionally-substituted with $C_{1-4}$alkyl, halogen, hydroxy, $C_{1-4}$alkoxy, trifluoromethyl, trifluoromethoxy, cyano, nitro, phenyl, benzyl, phenyloxy, benzyloxy, $NH_2$, NH($C_{1-4}$alkyl), N($C_{1-4}$alkyl)$_2$, cyclopentyl, cyclohexyl, or five or six membered heteroaryl or heterocycle.

In compounds of formula (I), preferably phenyl ring A is unsubstituted or has one substituent. Said optional substituent $R_{6a}$ or $R_{6b}$ is preferably selected from $C_{1-4}$alkyl, halogen, trifluoromethoxy, trifluoromethyl, hydroxy, $C_{1-4}$alkoxy, nitro, and cyano, more preferably the substituent is $R_{6a}$ and is methyl or ethyl.

In compounds of formula (I), preferably ring B is a cycloalkyl, heteroaryl, or heterocyclo ring selected from:

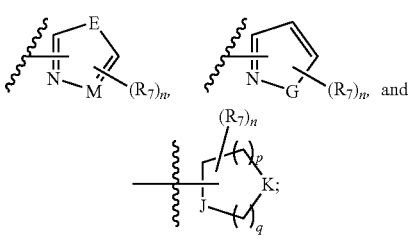

wherein E, G, J and K are selected from O, S, NH and $CH_2$, provided that when q is 0, then J and K are not simultaneously selected from O and S; and M is N or CH;

wherein each hydrogen atom of E, G, J, K and M may optionally be replaced with an $R_7$ group;

$R_7$ is selected from $C_{1-6}$alkyl, substituted $C_{1-4}$alkyl, halogen, trifluoromethoxy, trifluoromethyl, hydroxy, —$C_{1-4}$alkoxy, —C(=O)alkyl, —OC(=O)alkyl, NH$_2$, NH(C$_{1-4}$alkyl), N(C$_{1-4}$alkyl)$_2$, —CN, —CO$_2$alkyl, —CONH$_2$, —CONH (CH$_3$), —CON(CH$_3$)$_2$, phenyl, benzyl, C$_{3-7}$ cycloalkyl, and five-to-six membered heterocyclo or heteroaryl;

n is 0, 1 or 2; and p and q are selected from 0, 1, 2, 3 or 4, provided that p and q taken together are not greater than 4.

In compounds of formula (I), also preferred are compounds where ring B is cyclopropyl, oxazolyl, or isoxazolyl which is unsubstituted or has one substituent R$_7$. Said substituent R$_7$ preferably is selected from C$_{1-6}$alkyl, halogen, trifluoromethoxy, trifluoromethyl, hydroxy, —C$_{1-4}$alkoxy, —C(=O)alkyl, —OC(=O)alkyl, NH$_2$, NH(C$_{1-4}$alkyl), N(C$_{1-4}$alkyl)$_2$, —CN, —CO$_2$alkyl, —CONH$_2$, phenyl, benzyl, C$_{3-7}$ cycloalkyl, and five-to-six membered heterocyclo or heteroaryl, or a C$_{1-4}$alkyl substituted with hydroxy, amino, alkylamino, halogen, trifluoromethyl, trifluoromethoxy, or cyano. More preferably R$_7$ is not present or is —C$_{1-4}$alkoxy.

Also preferred compounds are those of formula (2a) and (2b),

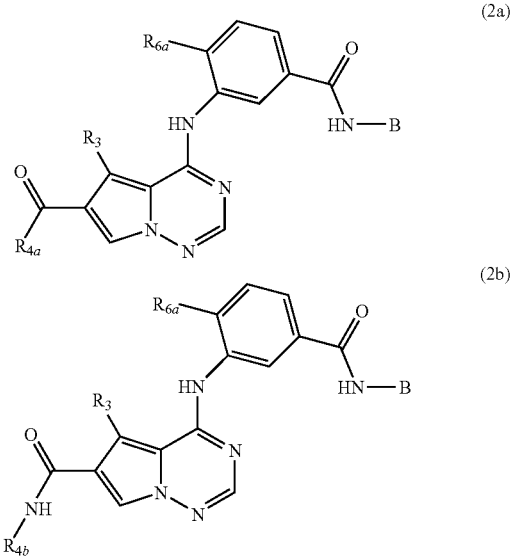

and pharmaceutically acceptable salts, prodrugs, and solvates thereof, wherein:

R$_3$ is methyl or CF$_3$;

B is phenyl having at least one R$_{11}$ substituent and zero to two R$_{12}$ substituents, or B may be selected from:

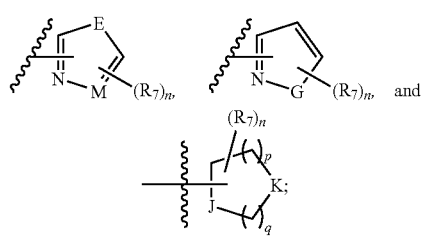

wherein E, G, J and K are selected from O, S, NH and CH$_2$, provided that when q is 0, then J and K are not simultaneously selected from O and S; and M is N or CH; wherein each hydrogen atom of E, G, J, K and M optionally may be replaced with an R$_7$ group;

R$_{4a}$ is phenyl or five or six membered heteroaryl optionally substituted with up to two R$_{16}$;

R$_{4b}$ is straight or branched C$_{2-6}$alkyl; cycloalkyl optionally substituted with keto and/or up to two R$_{16}$; heterocycle optionally substituted with keto and/or up to two R$_{16}$; or C$_{1-4}$alkyl substituted with up to three of halogen, trifluoromethyl, cyano, hydroxy, alkoxy, haloalkyl, haloalkoxy, nitro, phenyl, phenyloxy or benzyloxy, wherein said phenyl group in turn is optionally substituted with one to two R$_{26}$;

R$_{6a}$ is lower alkyl, halogen, trifluoromethoxy, trifluoromethyl, hydroxy, C$_{1-4}$alkoxy, nitro, amino, C$_{1-4}$alkylalmino, or cyano;

R$_7$ is C$_{1-4}$alkyl, trifluoromethyl, trifluoromethoxy, halogen, cyano, nitro, amino, C$_{1-4}$alkylalmino, hydroxy, C$_{1-4}$alkoxy, phenyl, benzyl, phenyloxy, or benzyloxy;

R$_{11}$ is cycloalkyl, heterocyclo, or heteroaryl optionally substituted with one to two R$_{16}$;

R$_{12}$ and R$_{16}$ at each occurrence are independently selected from hydrogen, alkyl, trifluoromethyl, trifluoromethoxy, halogen, cyano, nitro, amino, C$_{1-4}$alkylalmino, hydroxy, alkoxy, phenyl, benzyl, phenyloxy, and benzyloxy;

R$_{26}$ is selected from C$_{1-4}$alkyl, trifluoromethyl, trifluoromethoxy, halogen, cyano, amino, C$_{1-4}$alkylalmino, hydroxy, alkoxy, phenyl, benzyl, phenyloxy, and benzyloxy;

n is 0, 1 or 2; and p and q are 0, 1, 2, 3, or 4, provided that p and q taken together are not greater than 4.

Most preferred are compounds of formula (2a) or (2b), referenced above, and pharmaceutically acceptable salts, prodrugs, and solvates thereof, wherein:

R$_3$ is methyl;

B is selected from a) cyclopropyl or cyclobutyl optionally substituted with one to two R$_7$;

b) phenyl substituted with five or six membered heterocyclo and zero to two R$_{12}$, or c) B is selected from one of:

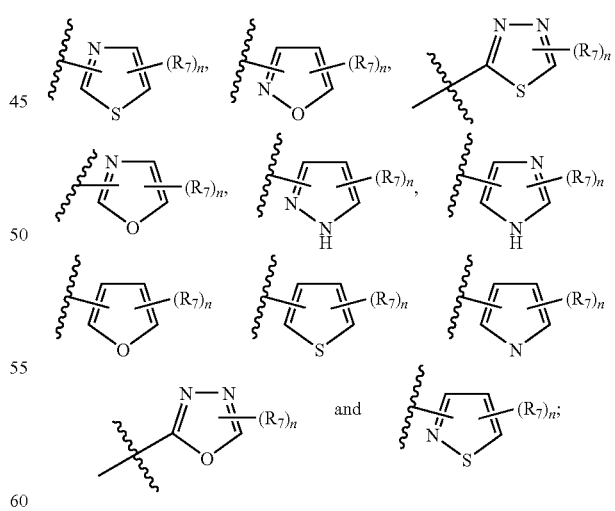

R$_{4a}$ is phenyl or pyridyl optionally substituted with up to two R$_{16}$, as defined above;

R$_{4b}$ is straight or branched C$_{2-6}$alkyl or optionally-substituted benzyl;

R$_{6a}$ is methyl, ethyl, halogen, trifluoromethoxy, trifluoromethyl, hydroxy, methoxy, ethoxy, or cyano;

$R_7$, $R_{12}$ and $R_{16}$ are selected from $C_{1-4}$alkyl, trifluoromethyl, trifluoromethoxy, halogen, cyano, nitro, amino, $C_{1-4}$alkylamino, amino$C_{1-4}$alkyl, hydroxy, hydroxy$C_{1-4}$alkyl, halo$C_{1-4}$alkyl, $C_{1-4}$alkoxy, phenyl, benzyl, phenyloxy, and benzyloxy; and n is 0 or 1.

Utility

The compounds of the invention are selective inhibitors of p38 kinase activity, and in particular, isoforms p38α and p38β. Accordingly, compounds of formula (I) have utility in treating conditions associated with p38 kinase activity. Such conditions include diseases in which cytokine levels are modulated as a consequence of intracellular signaling via p38, and in particular, diseases that are associated with an overproduction of cytokines IL-1, IL-4, IL-8, and TNF-α. As used herein, the terms "treating" or "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms. When reference is made herein to inhibition of "p-38α/β kinase," this means that either p38α and/or p38β kinase are inhibited. Thus, reference to an $IC_{50}$ value for inhibiting p-38α/β kinase means that the compound has such effectiveness for inhibiting at least one of, or both of, p38α and p38β kinases.

In view of their activity as inhibitors of p-38α/β kinase, compounds of Formula (I) are useful in treating p-38 associated conditions including, but not limited to, inflammatory diseases, autoimmune diseases, destructive bone disorders, proliferative disorders, angiogenic disorders, infectious diseases, neurodegenerative diseases, and viral diseases.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Grave's disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis and multiple myeloma-related bone disorder, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, and conditions associated with prostaglandin endoperoxidase syndase-2.

In addition, p38 inhibitors of this invention inhibit the expression of inducible pro-inflammatory proteins such as prostaglandin endoperoxide synthase-2 (PGHS-2), also referred to as cyclooxygenase-2 (COX-2). Accordingly, additional p38-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "p38 associated condition" or "p38 associated disease or disorder" are used herein, each is intended to encompass all of the conditions identified above as if repeated at length, as well as any other condition that is affected by p38 kinase activity.

The present invention thus provides methods for treating such conditions, comprising administering to a subject in need thereof an effective amount of at least one compound of Formula (I) or a salt thereof. The methods of treating p38 kinase-associated conditions may comprise administering compounds of Formula (I) alone or in combination with each other and/or other suitable therapeutic agents useful in treating such conditions. Exemplary of such other therapeutic agents include corticosteroids, rolipram, calphostin, CSAIDs, 4-substituted imidazo[1,2-A]quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The present invention also provides pharmaceutical compositions capable of treating p38-kinase associated conditions, including TNF-α, IL-1, and/or IL-8 mediated conditions, as described above. The inventive compositions may contain other therapeutic agents as described above and may be formulated, for example, by employing conventional solid or liquid vehicles or diluents, as well as pharmaceutical additives of a type appropriate to the mode of desired administration (e.g. excipients, binders, preservatives, stabilizers, flavors, etc.) according to techniques such as those well known in the art of pharmaceutical formulation.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of p38 enzyme levels.

Compounds of formula (I), including the compounds described in the examples hereof, have been tested in one or more of the assays described below and have shown activity as inhibitors of p38α/β enzymes and TNF-α.

Biological Assays

Generation of p38 Kinases cDNAs of human p38α, β and γ isozymes were cloned by PCR. These cDNAs were subcloned in the pGEX expression vector (Pharmacia). GST-p38 fusion protein was expressed in *E. Coli* and purified from bacterial pellets by affinity chromatography using glutathione agarose. p38 fusion protein was activated by incubating with constitutively active MKK6. Active p38 was separated from MKK6 by affinity chromatography. Constitutively active MKK6 was generated according to Raingeaud et al. [*Mol. Cell. Biol.*, 1247-1255 (1996)].

TNF-α Production by LPS-Stimulated PBMCs

Heparinized human whole blood was obtained from healthy volunteers. Peripheral blood mononuclear cells (PBMCs) were purified from human whole blood by Ficoll-Hypaque density gradient centrifugation and resuspended at a concentration of $5\times10^6$/ml in assay medium (RPMI medium containing 10% fetal bovine serum). 50 ul of cell suspension was incubated with 50 ul of test compound (4× concentration in assay medium containing 0.2% DMSO) in 96-well tissue culture plates for 5 minutes at RT. 100 ul of LPS (200 ng/ml stock) was then added to the cell suspension and the plate was incubated for 6 hours at 37° C. Following incubation, the culture medium was collected and stored at −20° C. TNF-α concentration in the medium was quantified using a standard ELISA kit (Pharmingen-San Diego, Calif.). Concentrations of TNF-α and $IC_{50}$ values for test compounds (concentration of compound that inhibited LPS-stimulated TNF-α production by 50%) were calculated by linear regression analysis.

p38 Assay

The assays were performed in V-bottomed 96-well plates. The final assay volume was 60 μl prepared from three 20 μl additions of enzyme, substrates (MBP and ATP) and test compounds in assay buffer (50 mM Tris pH 7.5, 10 mM $MgCl_2$, 50 mM NaCl and 1 mM DTT). Bacterially expressed, activated p38 was pre-incubated with test compounds for 10 min. prior to initiation of reaction with substrates. The reaction was incubated at 25° C. for 45 min. and terminated by adding 5 µl of 0.5 M EDTA to each sample. The reaction mixture was aspirated onto a pre-wet filtermat using a Skatron Micro96 Cell Harvester (Skatron, Inc.), then washed with PBS. The filtermat was then dried in a microwave oven for 1 min., treated with MeltilLex A scintillation wax (Wallac), and counted on a Microbeta scintillation counter Model 1450 (Wallac). Inhibition data were analyzed by nonlinear least-squares regression using Prizm (GraphPadSoftware). The final concentration of reagents in the assays are ATP, 1 µM; [γ-$^{33}$P]ATP, 3 nM; MBP (Sigma, #M1891), 2 µg/well; p38, 10 nM; and DMSO, 0.3%.

TNF-α Production by LPS-Stimulated Mice

Mice (Balb/c female, 6-8 weeks of age, Harlan Labs; n=8/treatment group) were injected intraperitoneally with 50 ug/kg lipopolysaccharide (LPS; E. coli strain 0111:B4, Sigma) suspended in sterile saline. Ninety minutes later, mice were sedated by $CO_2$:$O_2$ inhalation and a blood sample was obtained. Serum was separated and analyzed for TNF-alpha concentrations by commercial ELISA assay per the manufacturer's instructions (R&D Systems, Minneapolis, Minn.).

Test compounds were administered orally at various times before LPS injection. The compounds were dosed either as suspensions or as solutions in various vehicles or solubilizing agents.

ABBREVIATIONS

For ease of reference, the following abbreviations are employed herein, including the methods of preparation and Examples that follow:
Ph=phenyl
Bz=benzyl
t-Bu=tertiary butyl
Me=methyl
Et=ethyl
Pr=propyl
Iso-P=isopropyl
MeOH=methanol
EtOH=ethanol
EtOAc=ethyl acetate
Boc=tert-butyloxycarbonyl
DCM=dichloromethane
DCE=1,2-dichloroethane
DMF=dimethyl formamide
DMSO=dimethyl sulfoxide
TFA=trifluoroacetic acid
THF=tetrahydrofuran
HATU=O-(7-Azabenzotriazol-1-yl-N,N,N',N'-tetramethyluronim hexafluorophosphate
KOH=potassium hydroxide
$K_2CO_3$=potassium carbonate
$POCl_3$=phosphorous oxychloride
EDC or EDCI=1-(3-Dimethylaminopropyl)-3-ethylcarbodiimide hydrochloride
DIPEA=diisopropylethylamine
HOBt=1-hydroxybenzotriazole hydrate
m-CPBA=m-chloroperbenzoic acid
NaH=sodium hydride
NaOH=sodium hydroxide
Pd=palladium
Pd/C=palladium on carbon
min=minute(s)
L=liter
mL=milliliter
µL=microliter
g=gram(s)
mg=milligram(s)
mol=moles
mmol=millimole(s)
meq=milliequivalent
RT or rt=room temperature
ret. t. =HPLC retention time (minutes)
sat or sat'd=saturated
aq.=aqueous
TLC=thin layer chromatography
HPLC=high performance liquid chromatography
RP HPLC=reverse phase HPLC
LC/MS=high performance liquid chromatography/mass spectrometry
MS=mass spectrometry
NMR=nuclear magnetic resonance
mp=melting point In the Examples, designations associated with HPLC data reflect the following conditions:
a. Column: YMC ODSA S-5 5u C18 4.6×50 mm; Solvent: solvent A=10% MeOH/90% water/0.1% THF, and solvent B=90% MeOH/10% water/0.1% THF; Method: 4 min gradient;
b. Column: YMC s5 ODS 4.6×50 mm; Solvent: solvent A=10% MeOH/90% water/0.2% $H_3PO_4$, and solvent B=90% MeOH/10% water/0.2% $H_3PO_4$; Method: 4 min gradient.

Methods of Preparation

Compounds of formula I may generally be prepared according to the following schemes and the knowledge of one skilled in the art, and/or the methods described in U.S. patent application Ser. Nos. 10/036,293 and/or 09/573,829, incorporated herein by reference. In the schemes, the groups $R_1$-$R_7$, X, Y, m, n and p are as described herein for compounds of Formula (I). The reference to "B" is intended to encompass an optionally-substituted cycloalkyl, heterocyclo, or heteroaryl ring in formula (I), including without limitation the rings shown as:

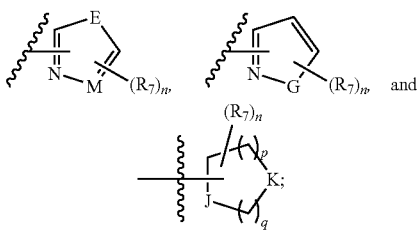

Scheme 1

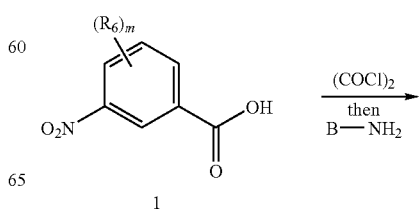

-continued

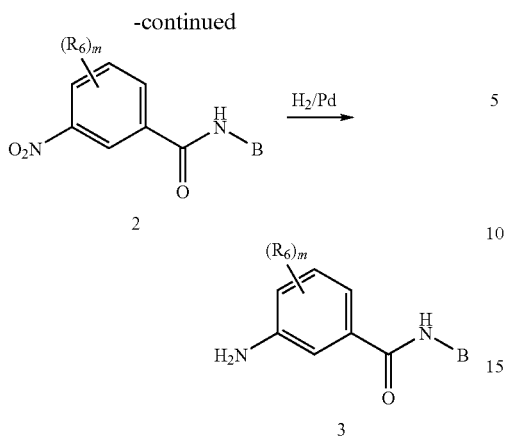

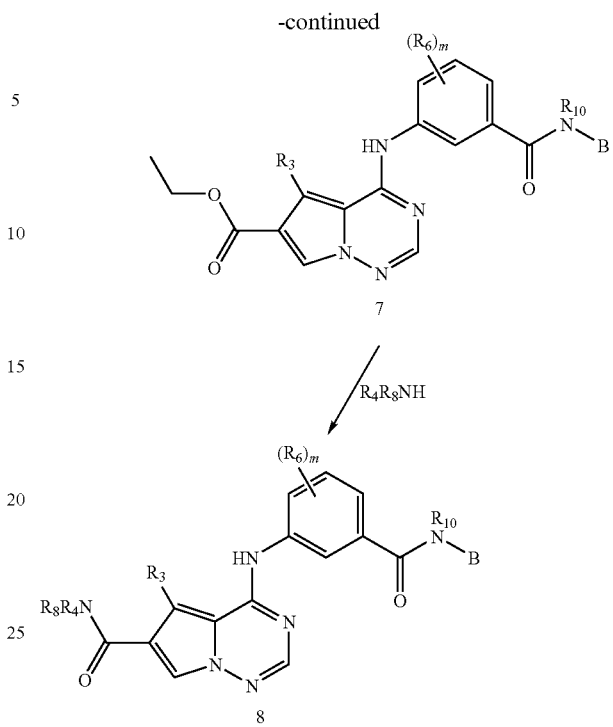

Commercially-available compound (1) can be reacted with oxalyl chloride with heating and then concentrated in vacuo and reacted with an amine B—NH$_2$ in the presence of a base, such as diisopropylamine, in an organic solvent, such as DCM to yield compound (2). Compound (2) can be reacted with hydrogen in the presence of a catalyst, such as Pd, in an alcoholic solvent, such as EtOH, at rt to afford compound (3). Compound (3) can then be used as in Scheme 2 to produce compounds (8) of Scheme 2.

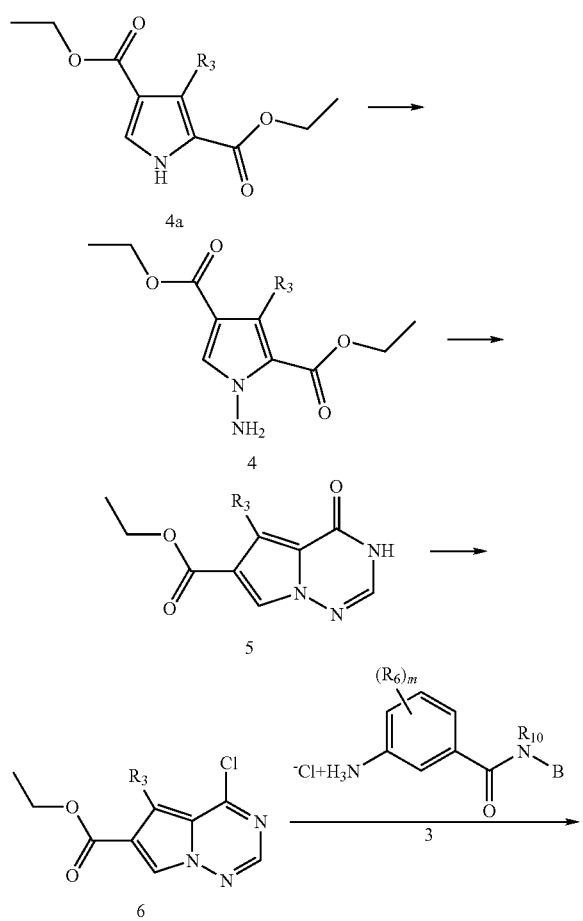

Scheme 2

3-methyl-1-pyrrole-2,4-diethyl ester can be reacted with chloramine in ether to produce compound (4). Reacting compound (4) in formamide with acetic acid produces compound (5). Compound (5) can be reacted with DIPEA and POCl$_3$ in toluene to produce compound (6). Compound (6) can be reacted with DIPEA and compound (3) in DMF to produce compound (7). Compound (7) can be reacted in THF with NaOH to produce an acid intermediate which upon treatment with HOBt, EDCI and the appropriate amine (NR$_2$R$_{10}$) in DMF produces compounds (8).

Compound (3) can be prepared by 1) reacting commercially-available 4-amino-3-methylbenzoic acid and N-(tert-butoxycarbonyl)anhydride in THF to produce a Boc-protected aniline intermediate; 2) reacting the aniline intermediate with -(3-dimethylaminopropyl)-3-ethylcarbodiimide hydrochloride, HOBt, and DMF, followed by addition of methoxyamine hydrochloride and DIPEA to produce a BOC-protected N-methoxyamide intermediate; and 3) reacting that methoxyamide intermediate in a solution of HCl in dioxane to produce compound (3) as a hydrochloride salt. Alternatively, compound (3) can be prepared as shown in Scheme 1.

Scheme 3

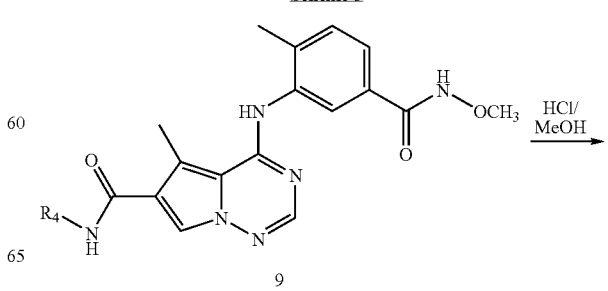

-continued

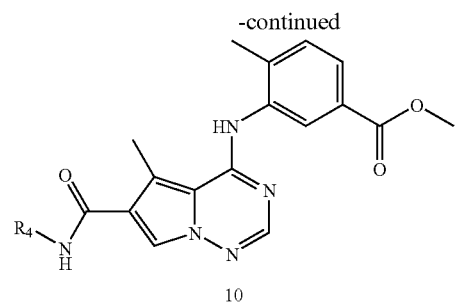
10

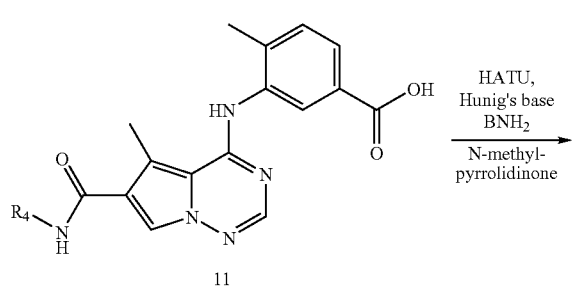
11

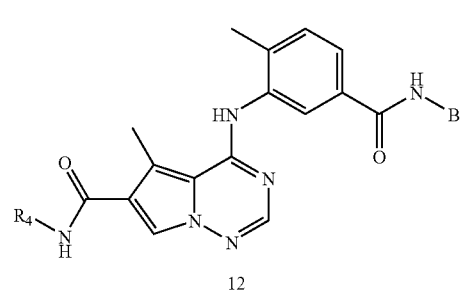
12

A substituted hydroxamate (9) can be reacted with acid, such as HCl, in anhydrous MeOH, to afford compound (10). Compound (10) can be reacted with an aq. base such KOH with heating to form compound (11). Compound (11) is reacted with an amine B—NH$_2$ in the presence of a coupling reagent, such as HATU, and a base such as diisopropylamine, in an organic solvent, such as N-methylpyrrolidinone to afford compounds (12). Hydroxamate (9) can be prepared as outlined in Schemes 1 and 2 and/or as shown in U.S. patent application Ser. No. 10/036,293.

Scheme 4

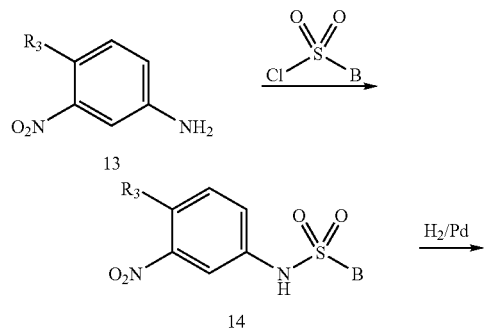

-continued

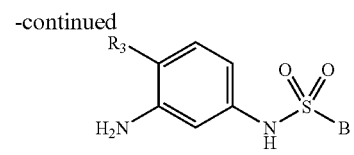
15

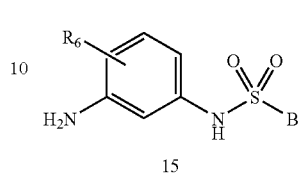
15
+

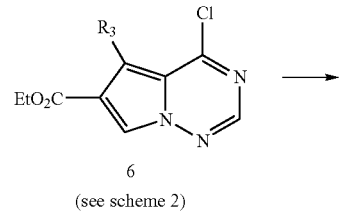
6
(see scheme 2)

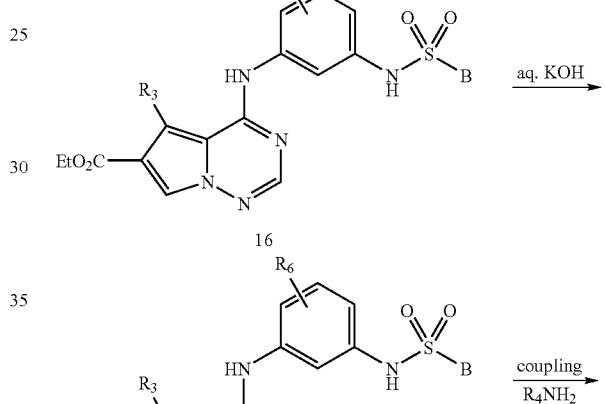
16

17

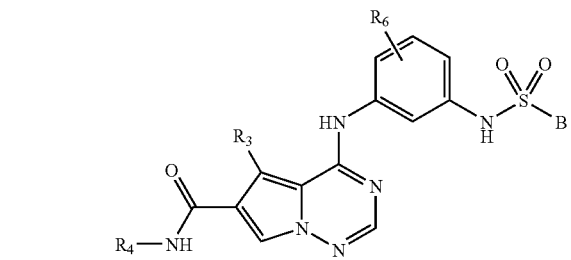
18

Commercially-available compound (13) can be reacted with a sulfonyl chloride in the presence of a base, such as TEA, in an organic solvent, such as DCM to yield compound (14). Reaction of compound (14) with hydrogen in the presence of a catalyst, such as Pd in a solvent, such as MeOH, yields compound (15). Reaction of compound (15) with chloride (6) (see scheme 2) in an organic solvent, such as DMF, at rt affords compound (16).

Reaction of compound (16) with aq. KOH with heating affords compound (17). Compound (17) can be reacted with an amine R₂NH₂ in the presence of a coupling reagent, such as EDCI, and a base such as diisopropylamine, in an organic solvent, such as DMF to afford compound (18).

Scheme 5

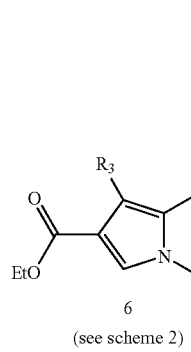
6
(see scheme 2)

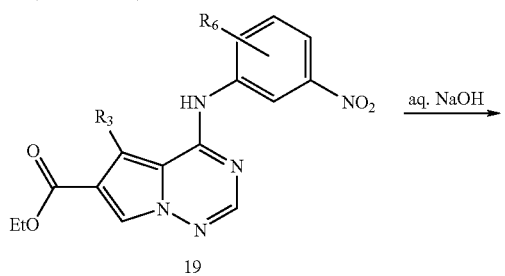
19

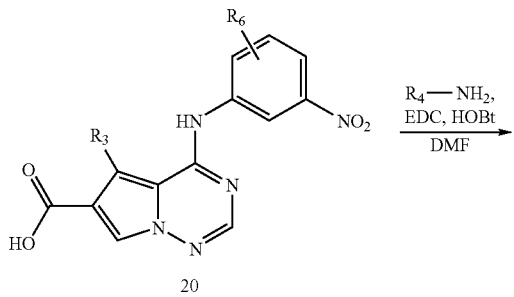
20

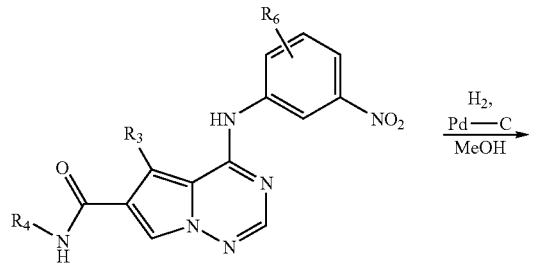
21

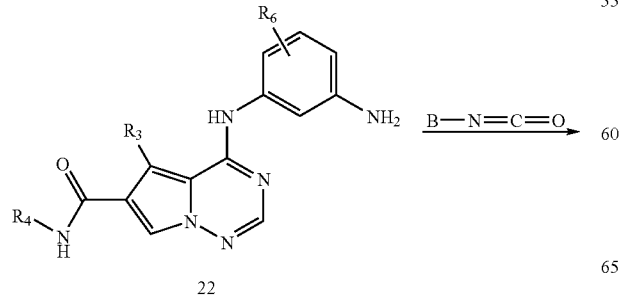
22

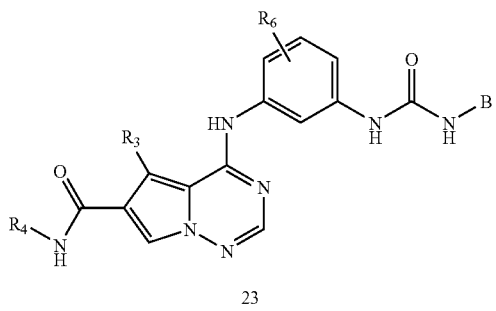
23

Chloropyrrolotriazine (6) (see Scheme 2) can be reacted with an aniline (13) (e.g., see Scheme 4) in anhydrous DMF at rt to afford compound (19). Reaction of compound (19) with an aq. base such as NaOH with heating affords compound (20). Compound (20) can be reacted with an amine R₄NH₂ in the presence of a coupling reagent, such as HOBt, with or without a base such as diisopropylamine, in an organic solvent, such as DMF to afford compound (21). Compound (21) can be reacted with hydrogen in the presence of a catalyst, such as Pd/C, in an organic solvent, such as MeOH to afford compound (22). Reaction of compound (22) with an isocyanate in an organic solvent, such as DCE affords compound (23).

Scheme 6

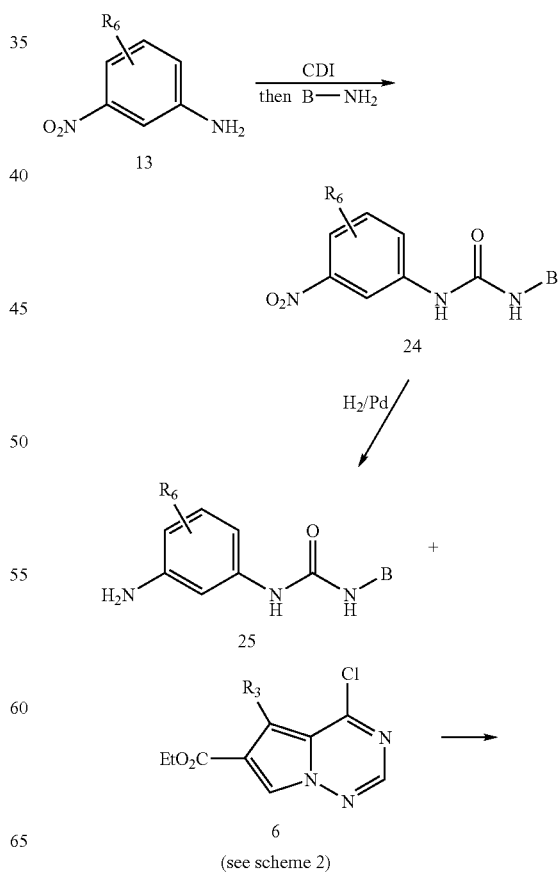

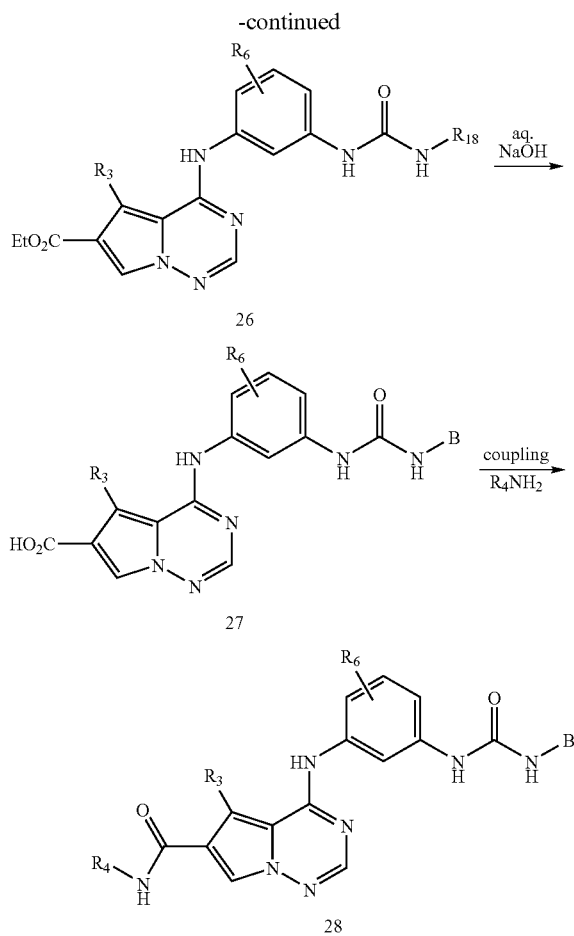

Commercially-available compound (13), can be reacted with carbonyl diimidazole and an amine B—NH$_2$ in an organic solvent, such as DCE, to yield compound (24). Reaction of compound (24) with hydrogen in the presence of a catalyst, such as Pd, in an alcoholic solvent such as EtOH affords compound (25). Reaction of (25) with chloride (6) in an organic solvent, such as DMF, affords compound (26). Reaction of (26) with aq. NaOH with heating affords product (27). Product (27) can be reacted with an amine R$_4$NH$_2$ in the presence of a coupling reagent, such as EDCI, and a base such as diisopropylamine, in an organic solvent, such as DMF to afford compound (28).

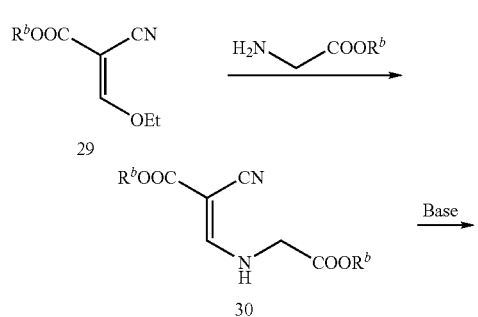

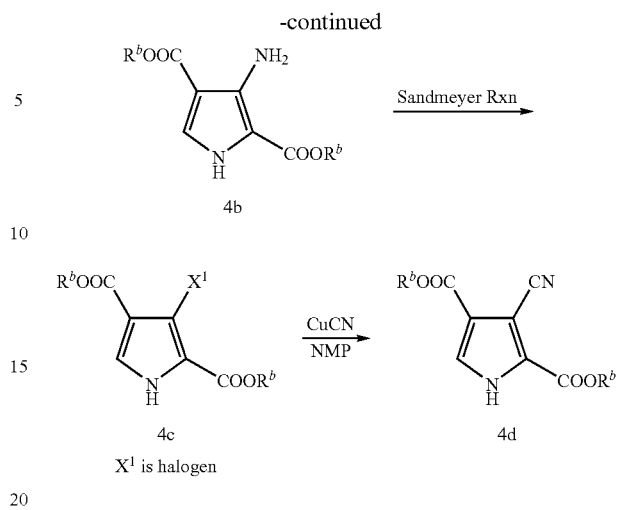

Scheme 7 shows methods for making compounds (4a) (see scheme 2), wherein R$_3$ is amino (4b), halogen (4c), or cyano (4d). Glycine ethyl ester (29) can be added to an alkyl alkoxy methylene cyanoacetate at from rt to 80° C. to obtain compound (30). Compound (30) is cyclized to form pyrrole (4b) upon treatment with a strong base, such as lithium hexamethyldisilazane, at from −78° C. to rt in an organic solvent such as THF. Pyrrole (4b) can be converted to a halide using sodium nitrite in an organic solvent, such as DMF, and a halide source, such as CuBr to yield compound (4c). Compound (4c) can be converted to compound (4d) using CuCN in an organic solvent such as NMP at elevated temperatures. Alternatively, compound (4b) can be directly converted to compound (4d) using sodium nitrite in an organic solvent, such as DMF, and a cyanide source such as CuCN. Compounds (4a)-(4d) can be used as described in previous schemes (e.g., Scheme 2), to form compounds of Formula (I) herein.

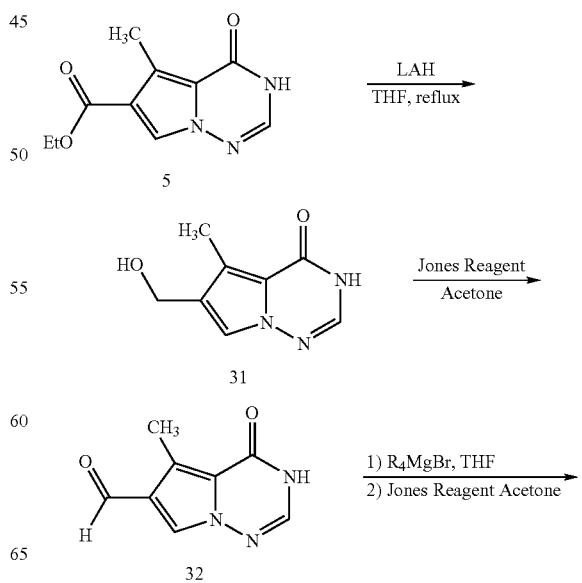

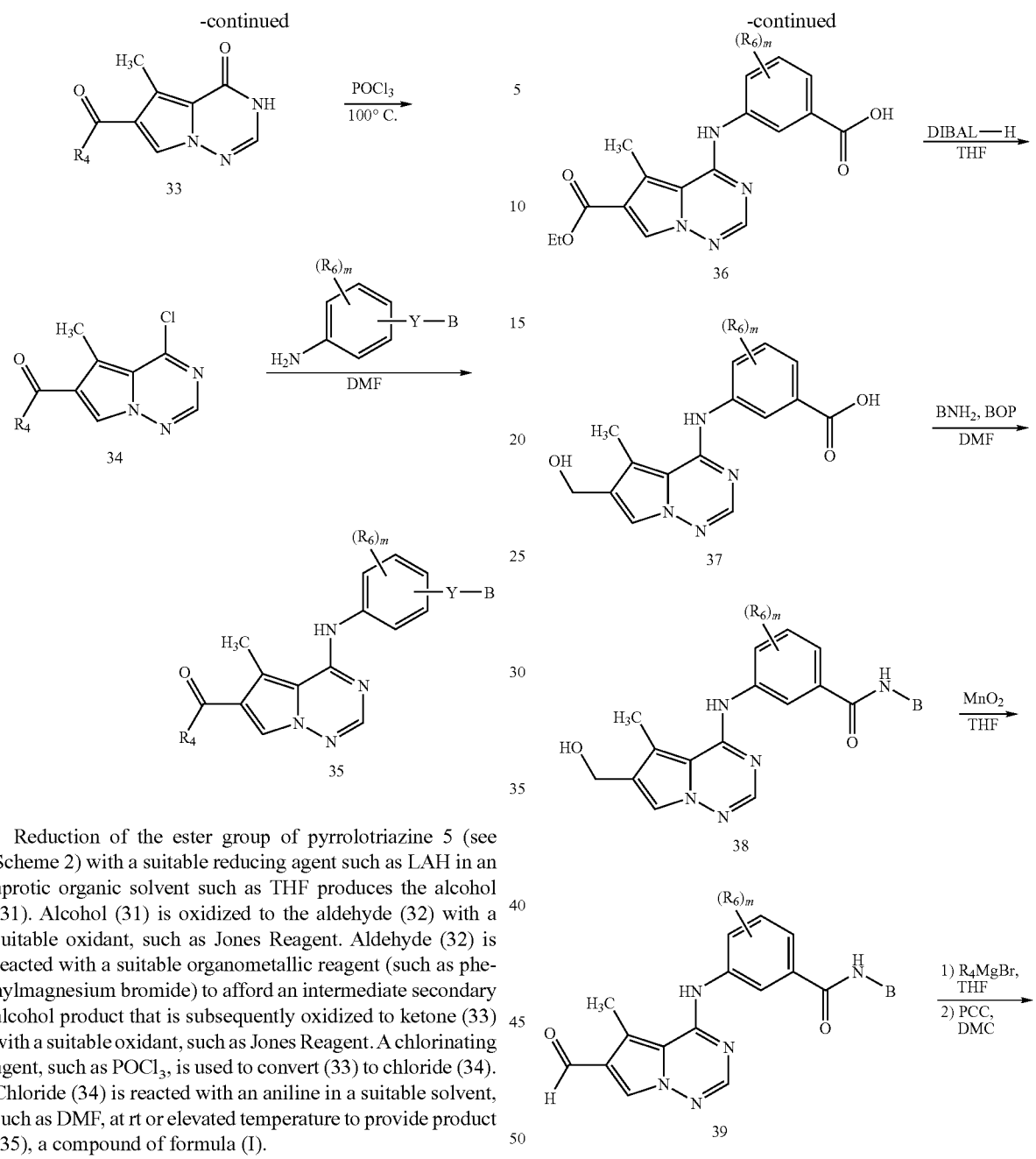

Reduction of the ester group of pyrrolotriazine 5 (see Scheme 2) with a suitable reducing agent such as LAH in an aprotic organic solvent such as THF produces the alcohol (31). Alcohol (31) is oxidized to the aldehyde (32) with a suitable oxidant, such as Jones Reagent. Aldehyde (32) is reacted with a suitable organometallic reagent (such as phenylmagnesium bromide) to afford an intermediate secondary alcohol product that is subsequently oxidized to ketone (33) with a suitable oxidant, such as Jones Reagent. A chlorinating agent, such as $POCl_3$, is used to convert (33) to chloride (34). Chloride (34) is reacted with an aniline in a suitable solvent, such as DMF, at rt or elevated temperature to provide product (35), a compound of formula (I).

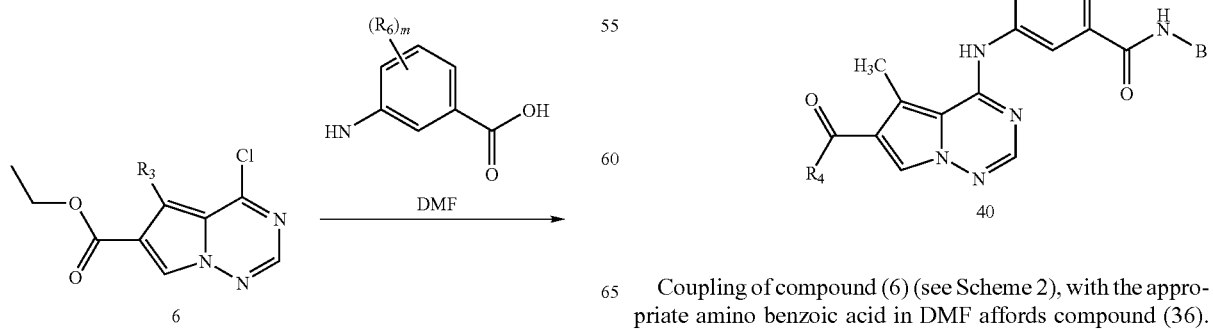

Coupling of compound (6) (see Scheme 2), with the appropriate amino benzoic acid in DMF affords compound (36). Reduction of the ester group of compound (36), with a suitable reducing agent such as DIBAL-H in an aprotic organic solvent such as THF produces the alcohol (37). Alcohol (37) can be reacted with an amine $RNH_2$ in the presence of a coupling reagent, such as BOP, in an organic solvent, such as DMF, to afford the product (38). Product (38) is oxidized to aldehyde (39) with a suitable oxidant, such as $MnO_2$, in an organic solvent such as THF. Aldehyde (39) is reacted with a suitable organometallic reagent (such as phenylmagnesium bromide) to afford an intermediate secondary alcohol product that is subsequently oxidized to the ketone (40) with a suitable oxidant, such as PCC.

In addition, other compounds of formula I may be prepared using procedures generally known to those skilled in the art. In particular, the following examples provide additional methods for the preparation of the compounds of this invention.

The invention will now be further described by the following working examples, which are preferred embodiments of the invention. HPLC purifications were done on C18 reverse phase (RP) columns using water MeOH mixtures and TFA as buffer solution. These examples are illustrative rather than limiting. There may be other embodiments that fall within the spirit and scope of the invention as defined by the appended claims.

EXAMPLE 1

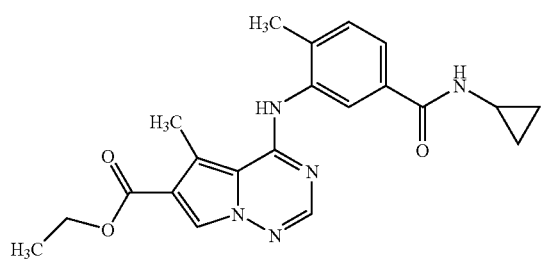

Step A:

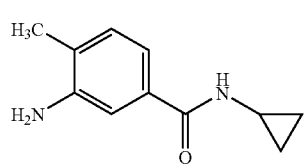
(1A)

To a solution of 3-amino-4-methylbenzoic acid (5.12 g, 33.9 mmol, 1.0 eq.), EDC (9.97 g, 52.0 mol, 1.5 eq.) and 4-(dimethylamino)pyridine (0.89 g, 7.3 mol, 0.2 eq.) in DMF (100 mL) at 0° C. was added cyclopropylamine (4.0 mL, 57.7 mol, 1.7 eq.) dropwise. After stirring for 15 min., the cold bath was removed, and the reaction mixture was stirred at rt overnight. Volatiles were removed at 50° C. under reduced pressure. The residue was diluted with water and extracted with DCM (3×). The organic layers were combined, dried over sodium sulfate, and concentrated in vacuo to give an oil. Silica gel chromatography using DCM:MeOH (20:1) afforded compound IA as a yellow oil (6.98 g, 108% yield). HPLC Ret. t.=0.637 min.; LC/MS (M+H)+=191.09+.

Step B:

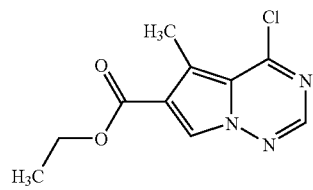
(1B)

To a suspension of the starting oxopyrrolotriazine (3.00 g, 13.6 mmol) in toluene (45 mL) was added dropwise phosphorus oxychloride (1.90 mL, 20.4 mmol) and N,N-DIPEA (2.37 mL, 13.6 mmol) successively at rt. The resulting mixture was heated at reflux for 36 h, allowed to cool to rt, and then poured into an ice-cold mixture of sat'd sodium bicarbonate solution (150 mL) and toluene (60 mL). The organic layer was separated and the aqueous layer extracted with toluene (3×50 mL). The combined extract was washed with sat'd sodium bicarbonate solution and brine and dried over anhydrous $MgSO_4$. Evaporation of solvent in vacuo afforded compound 1B (3.26 g, 100% yield) as a yellow solid.

Step C: Example 1

A solution of products 1A (1.60 g, 8.40 mmol, 1.6 eq.) and 1B (1.30 g, 5.40 mmol, 1.0 eq.) in DMF (13 mL) was stirred at rt overnight. Water was added and the precipitate collected by filtration, washed with water, and dried. Trituration with diethyl ether afforded Example 1 (1.70 g, 80% yield) as an off-white solid. HPLC Ret. t.=3.190 min.; LC/MS (M+H)+=394.31+.

EXAMPLE 2

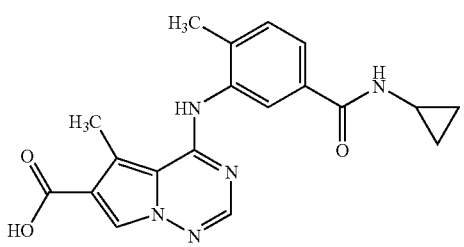

A solution of Example 1 (0.86 g, 2.20 mmol, 1.0 eq.) in THF (4.0 mL) and 1 N aqueous NaOH (9.0 mL, 4.1 eq.) was stirred at 60° C. overnight. After cooling to rt, the reaction mixture was concentrated in vacuo but not to dryness. To the solution at 0° C. was added 1 N aqueous hydrochloric acid until it was acidic and the precipitate was collected and dried to afford crude Example 2 (0.51 g, 64.0% yield). HPLC Ret. t.=2.400 min.; LC/MS (M+H)+=366.06+. The filtrate was then extracted with EtOAc (3×) and the organic layers were combined, dried over sodium sulfate, and concentrated in vacuo to give Example 2 (0.035 g, 4.4% yield).

EXAMPLE 3

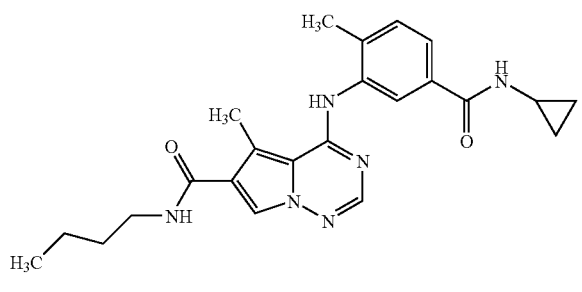

A solution of Example 2 (0.026 g, 0.071 mmol, 1.0 eq.), EDC (0.021 g, 0.11 mmol, 1.5 eq.), HOBt (0.015 g, 0.11 mmol, 1.5 eq), n-butylamine (0.015 mL, 0.15 mmol, 2.1 eq.) and DIPEA (0.040 mL, 0.23 mmol, 3.2 eq.) in DMF (0.20 mL) was shaken at rt overnight. Water (1 mL) was added and the precipitate collected by filtration, washed with water, and dried to give Example 3 (0.021 g, 70% yield); HPLC Ret. t.=2.883 min.; LC/MS (M+H)$^+$=421.18$^+$.

EXAMPLES 4-22

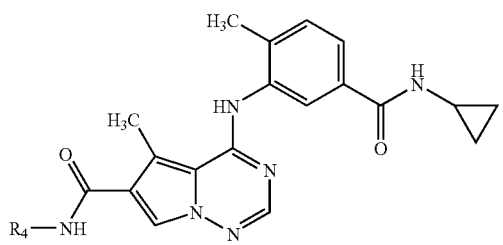

(Id)

Compounds having the formula (Id), above, wherein $R_4$ has the values listed in the following Table, were prepared following the same procedure described for Example 3, using the appropriate amine in place of n-butylamine.

| Ex. # | $R_4$ | $(M + H)^+$ | HPLC Ret. t. (min) |
|---|---|---|---|
| 4 | ethyl | 393.30 | 2.29$^a$ |
| 5 | isopropyl | 407.27 | 2.51$^a$ |
| 6 | (R)-1-phenylethyl | 469.35 | 3.08$^a$ |
| 7 | n-propyl | 407.21 | 2.56$^a$ |
| 8 | n-pentyl (sec) | 421.18 | 2.88$^a$ |
| 9 | 2-methoxyethyl | 423.17 | 2.22$^a$ |
| 10 | (1H-benzimidazol-2-yl)methyl | 495.26 | 2.22$^a$ |
| 11 | (2,3-dihydro-1,4-benzodioxin-2-yl)methyl | 513.15 | 3.16$^a$ |
| 12 | 1-cyclopropyl-1-methyl | 405.07 | 2.34$^a$ |
| 14 | CH$_3$— | 379.17 | 2.05$^a$ |
| 15 | 2-morpholinoethyl (methyl) | 478.17 | 1.61$^a$ |
| 16 | 4-hydroxybutyl | 423.20 | 2.03$^a$ |
| 17 | isobutyl | 421.22 | 2.74$^a$ |
| 18 | (S)-2-hydroxy-1-phenylethyl | 485.92 | 2.68$^a$ |

-continued

| Ex. # | R₄ | (M + H)⁺ | HPLC Ret. t. (min) |
|---|---|---|---|
| 19 | 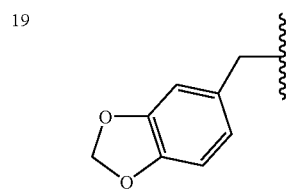 | 499.59 | 2.89ᵃ |
| 20 | 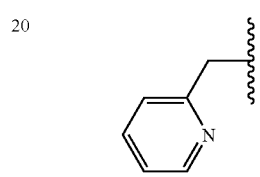 | 456.19 | 1.74ᵃ |
| 21 | 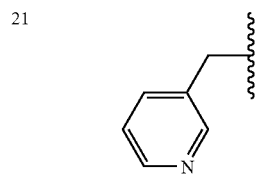 | 456.18 | 1.67ᵃ |
| 22 | 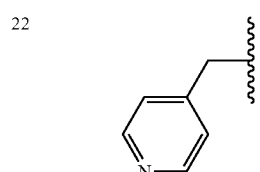 | 456.16 | 1.67ᵃ |

EXAMPLES 23-24

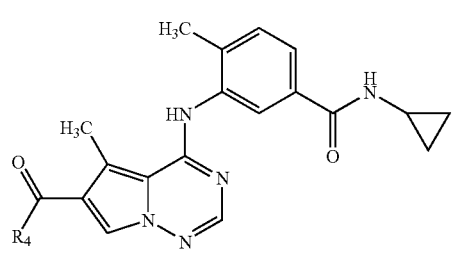

(Ie)

Compounds having the formula (Ie), above, wherein R₄ has the values listed in the following Table, were prepared following the same procedure described for Example 3, using piperizinylamine and morpholinylamine in place of n-butylamine.

| Ex. # | R₄ | (M + H)⁺ | HPLC Ret. t. (min) |
|---|---|---|---|
| 23 | piperidinyl | 433.12 | 2.73ᵃ |
| 24 | morpholinyl | 435.44 | 2.08ᵃ |

EXAMPLES 25-27

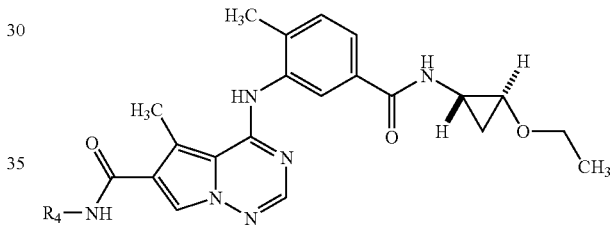

(If)

Compounds having the formula (If), wherein R₄ has the values listed in the Table provided below, were prepared following the same procedure described for Examples 1 through 3, using the appropriate amine in place of n-butylamine, and in place of cyclopropylamine in Step 1A, (±)-trans-ethoxycyclopropylamine, which was prepared following Steps A-D, below.

Step A:

(25A)

$H_3C\text{—}O\text{—}C(=O)\text{—}\triangle\text{—}O\text{—}CH_2CH_3$

To a well stirred mixture of ethyl vinyl ether (47.9 mL, 0.500 mol.) and Rhodium (II) acetate dimer (0.221 g, 0.500 mmol) in diethyl ether (10 mL) was slowly introduced ethyl diazoacetate (10.5 mL, 0.100 mol) in diethyl ether (30 mL) via a syringe pump at rt over 8 hours. The insoluble material was removed by filtration through Celite, and the excess ethyl vinyl ether and solvent were evaporated in vacuo. The residue was distilled in vacuo to give product 25A (10.3 g, 65% yield) as a colorless oil which was a mixture of cis and trans isomers in a ratio of approximately 1:1.

Step B:

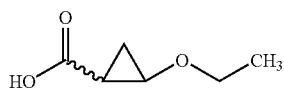
(25B)

To a solution of product 25A (10.3 g, 65.4 mmol) in MeOH (200 mL) was added a solution of NaOH (7.85 g, 196.2 mmol) in one portion, and the resulting solution was heated at reflux for 5 h. The mixture was concentrated under vacuum. The residue was acidified with 6 N HCl to pH=2 and extracted with EtOAc (5×). The combined organic phase was dried over MgSO$_4$. Evaporation of solvent in vacuo gave product 25B (8.46 g, 99% yield) as a colorless oil which was a mixture of cis and trans isomers in a ratio of approximately 1:1.

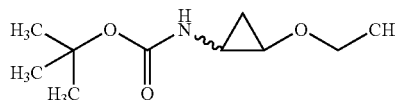
(25C)

A mixture of product 25B (1.00 g, 7.68 mmol), diphenylphosphoryl azide (1.82 mL, 8.44 mmol), and TEA (1.18 mL, 8.47 mmol) in anhydrous t-BuOH (30 mL) was heated at 90° C. for 27 h. The volatiles were evaporated in vacuo. The residue was diluted with 10% Na$_2$CO$_3$ solution (30 mL) and extracted with diethyl ether (4×30 mL). The combined organic phase was washed with brine, dried over MgSO$_4$, and the solution was concentrated in vacuo. Silica gel chromatography (40% Et$_2$O/hexane) of the residue afforded product 25C (0.901 g, 58% yield) as a colorless oil which was a mixture of cis and trans isomers in a ratio of approximately 15:85 in favor of trans isomer.

Step D:

A mixture of product 25C (0.881 g, 4.38 mmol) and 1 N HCl (20 mL) was heated at reflux for 5 h. After it was allowed to cool to rt, the mixture was extracted with diethyl ether. The aqueous layer was adjusted to pH=11 with 1 N NaOH solution, and then extracted with diethyl ether (4×). The combined organic phase was dried over MgSO$_4$ and evaporation of the solvent gave (±)-trans-ethoxycyclopropylamine (0.224 g, 50% yield) as a slightly yellow oil.

| Ex. # | R$_4$ | (M + H)$^+$ | HPLC Ret. t. (min) |
|---|---|---|---|
| 25 |  | 437.23 | 2.29$^a$ |
| 26 |  | 451.24 | 2.44$^a$ |
| 27 |  | 513.23 | 2.92$^a$ |

EXAMPLE 28

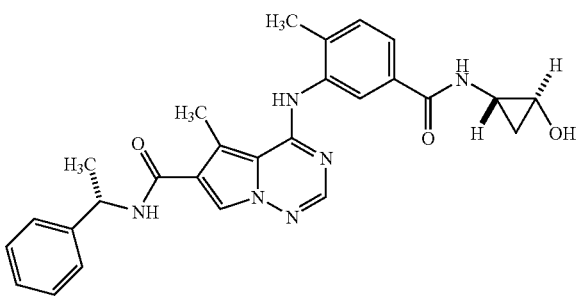

To a solution of Example 27 (30.0 mg, 0.0585 mmol) in DCE (6 mL) was added BBr$_3$ at 0° C. The resulting mixture was stirred at rt for 20 min., then quenched with water. The mixture was adjusted to pH=9 with sat'd Na$_2$CO$_3$ solution and extracted with EtOAc (3×). The combined organic phase was washed with brine and dried over MgSO$_4$. The solution was concentrated under vacuum and silica gel chromatography (6% MeOH/CHCl$_3$) of the residue afforded Example 28 (3.2 mg) as a white solid. HPLC Ret. t.=3.09 min. (b); LC/MS (M+H)$^+$=485.38$^+$.

EXAMPLES 29-30

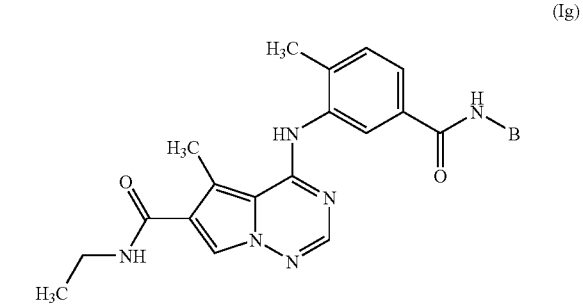
(Ig)

Compounds having the formula (Ig), wherein B has the values listed in the Table provided below, were prepared following the same procedures described for Examples 1 and 3, using an appropriately-substituted cyclopropyl amine in Step 1A and ethylamine in place of n-butylamine.

| Ex. # | B | (M + H)⁺ | HPLC Ret. t. (min) |
|---|---|---|---|
| 29 | | 469.50 | 3.02$^a$ |
| 30 | | 411.22 | 2.26$^a$ |

EXAMPLE 31

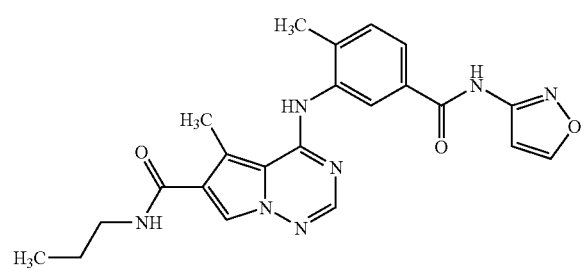

Step A:

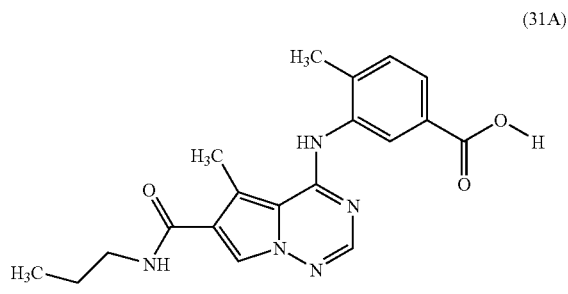
(31A)

Compound 31A was prepared following the procedures described in U.S. patent application Ser. No. 10/036,293, assigned to the present assignee, which is incorporated herein by reference.

Step B:

A mixture of compound 31A, 3-aminoisoxazole (0.30 mL, 4.06 mmol), benzotriazol-1-yloxytris(dimethylamino)phosphonium hexafluorophosphate (0.720 g, 1.63 mmol), and N-methylmorpholine (0.54 mL, 4.91 mmol) in DMF (4 mL) was heated at 65° C. for two days. The mixture was diluted with EtOAc and washed with water (2×), 10% Na$_2$CO$_3$ solution, and brine. The solution was concentrated in vacuo and the product isolated by preparative HPLC. HPLC Ret. t.=2.48 min. (a); LC/MS (M+H)⁺=434.11⁺.

EXAMPLES 32-38

Compounds having the formula (Ig), above, wherein B has the values listed in the Table provided below, were prepared following the same procedures described for Example 31, using ethylamine in place of propylamine to make the starting compound and in Step B, an appropriate aminoheteroaryl in place of aminoisooxazole.

| Ex. # | B | (M + H)⁺ | HPLC Ret. t. (min) |
|---|---|---|---|
| 32 | | 436.36 | 2.65$^a$ |
| 33 | | 492.62 | 3.66$^a$ |
| 34 | | 450.19 | 3.01$^a$ |
| 35 | | 420.14 | 2.52$^b$ |
| 36 | | 437.13 | 2.65$^b$ |
| 37 | | 420.25 | 2.23$^b$ |
| 38 | | 419.22 | 2.32$^b$ |

EXAMPLE 39

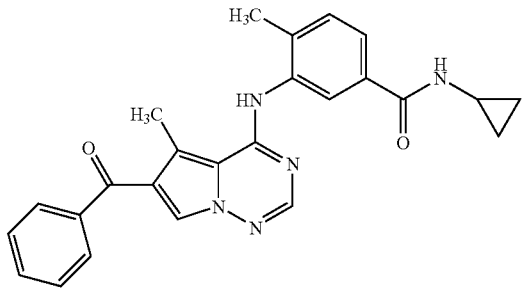

Step A:

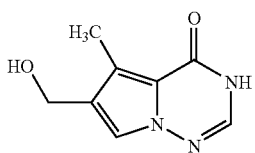

(39A)

To a solution of LAH (13.7 g, 362 mmol) in THF (800 mL) was added ester
having the formula

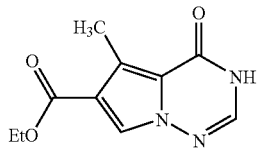

(8 g, 36.2 mmol) in several portions at rt. The reaction mixture was heated to reflux for 30 min., then cooled to rt, carefully quenched by being poured into ice water (1 L), and stirred rapidly for 1 h. The mixture was extracted with EtOAc and the combined extracts were washed with brine, dried over $MgSO_4$, filtered, and concentrated to give compound 39A (5.60 g, 86%).

Step B:

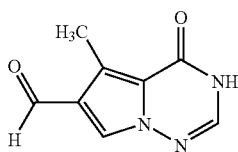

(39B)

To a suspension of compound 39A (1.0 g, 5.58 mmol) in acetone (80 mL) at 0° C. was added Jones Reagent (1.9 mL) dropwise. The reaction was stirred at 0° C. for 1 h, then carefully quenched with 2-propanol. Sat'd aq. sodium bicarbonate (100 mL) was added, and the mixture was extracted with EtOAc (5×100 mL). The combined extracts were washed with sat'd aq. sodium bicarbonate (1×100 mL), water (1×100 mL), and brine (1×100 mL), then dried over $MgSO_4$, filtered, and concentrated to afford compound 39B (647 mg, 65%). HPLC ret. t. (min): 1.50, MW: 177.16, LCMS $[M+H]^+=178$.

Step C:

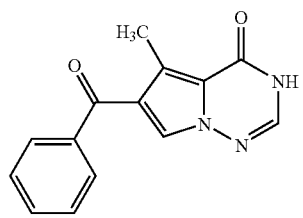

(39C)

To a solution of compound 39B (600 mg, 3.39 mmol) in THF (80 mL) at 0° C. was added phenylmagnesium bromide (3M, 2.94 mL, 8.8 mL) dropwise over 5 min. After stirring for 30 min at 0° C., the reaction was warmed to rt over 1 h and quenched with sat'd aq. ammonium chloride. The mixture was extracted with EtOAc and the extracts were dried, filtered, and concentrated to afford the benzylic alcohol intermediate. The crude benzylic alcohol was dissolved in acetone (50 mL) and cooled to 0° C. Jones Reagent (1 mL) was added dropwise and the reaction was stirred at 0° C. for 1 h, then carefully quenched with 2-propanol. Sat'd aq. sodium bicarbonate (50 mL) was added and the mixture was extracted with EtOAc (4×50 mL). The combined extracts were washed with sat'd aq. sodium bicarbonate (1×50 mL), water (1×50 mL), and brine (1×50 mL) before being dried over $MgSO_4$, filtered, and concentrated to afford compound 39C (563 mg, 66% over 2 steps). HPLC ret .t. (min): 2.82, MW: 253.26, LCMS $[M+H]^+=254$.

Step D:

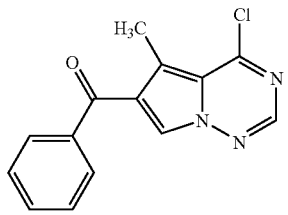

(39D)

Ketone 39C (152 mg, 0.6 mmol) was placed in $POCl_3$ (5 mL) and heated to 100° C. for 1.75 h. The reaction was cooled to rt and the excess $POCl_3$ was evaporated under vacuum. The residue was dissolved in anhydrous DCM (10 mL) and added dropwise to a rapidly stirred solution of sat'd aq. sodium bicarbonate (50 ml) and DCM (50 mL) at 0° C. The mixture was stirred for 1 h, then the aqueous phase was extracted with DCM (3×50 mL). The organic phases were washed with sat'd aq. sodium bicarbonate (1×50 mL), water (1×50 mL), and brine (1×50 mL), then dried over $MgSO_4$, filtered, and concentrated to afford the chloride 39D (163 mg, 100%).

Step E:

To a solution of the chloride 39D (31.5 mg, 0.116 mmol) in DMF (1 mL) was added 3-amino-N-cyclopropyl-4-methyl-benzamide (compound 1A) (44 mg, 0.23 mmol) and the solution was heated to 60° C. for 3 h. Water (5 mL) was added to precipitate the product, which was collected by filtration, washed with water, and allowed to air dry to give Example 39. HPLC ret. t. (min): 3.34, MW: 425.49, LCMS $[M+H]^+=426$.

EXAMPLES 40-42

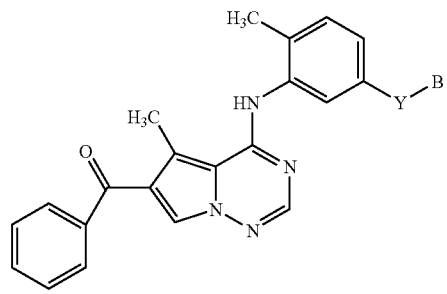

(Ih)

Compounds having the formula (Ih), wherein Y and B have the values listed in the Table provided below, were prepared following the same or similar procedure as described above for Example 39, using the appropriate amine in step E.

| Ex. No. | Y | B | MW | HPLC ret. time (min.) | MS (M+H)+ |
|---|---|---|---|---|---|
| 40 | —C(=O)NH— | ![3-fluoro-5-morpholinophenyl] | 564.62 | 3.87 | 565 |
| 41 | —C(=O)NH— | —CO$_2$CH$_3$ | 443.47 | 3.25 | 444 |
| 42 | —NHC(=O)— | ![3-fluoro-5-morpholinophenyl] | 564.62 | 3.50 | 565 |

EXAMPLE 43

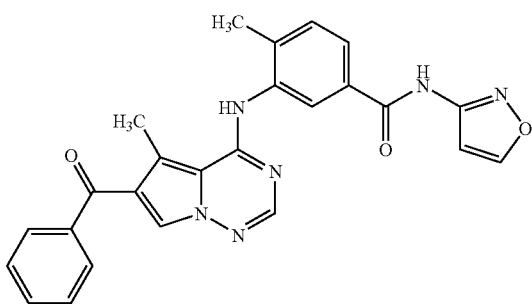

Step A:

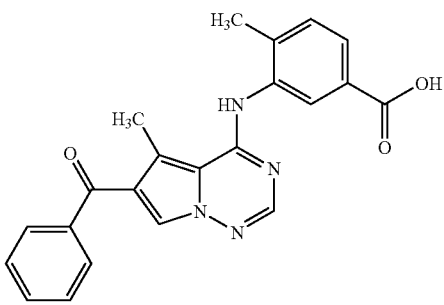

(43A)

To a solution of compound 39D (60 mg, 0.221 mmol) in DMF (1 mL) was added 3-amino-4-methyl-benzoic acid (66.8 mg, 0.442 mmol) and the solution was heated to 60° C. for 3 h. Water (5 mL) was added to precipitate the product, which was collected by filtration, washed with water, and allowed to air dry to give compound 43A (75 mg, 88%). HPLC ret. t. (min): 3.38, MW: 386.41, LCMS[M+H]$^+$=387.

Step B:

To a solution of the acid 43A (30 mg, 0.078 mmol) and HATU (44 mg, 0.117 mmol) and DIPEA (17 μL, 0.1 mmol) in DMF (0.5 mL) at rt was added 3-amino-isoxazole. The reaction was stirred at rt for 1 h, and water (5 mL) was added to precipitate the product, which was collected by filtration, and purified by preparative HPLC to afford Example 43. HPLC ret. t. (min): 3.39, MW: 452.48, LCMS[M+H]$^+$=453.

EXAMPLE 44

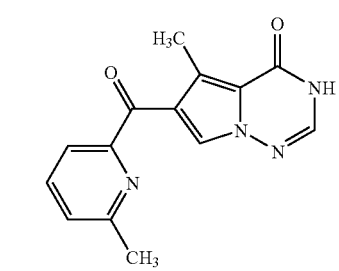

Step A:

(44A)

To a solution of the compound 39B (160 mg, 0.90 mmol) in THF (10 mL) at 0° C. was added 6-methyl-2-pyridylmagnesium bromide (0.25M, 14.4 mL, 3.6 mM) dropwise over 5 min. After stirring for 30 min at 0° C., the reaction was warmed to rt and stirred for 16 h. Additional aliquots of 6-methyl-2-pyridylmagnesium bromide were added to complete the conversion of the starting material and the reaction was quenched with sat'd aq. ammonium chloride. The mixture was extracted with EtOAc and the extracts were dried, filtered, and concentrated to afford a reddish brown semi-solid material. This material was dissolved in acetone (10 mL) and cooled to 0° C. Jones Reagent (0.4 mL) was added dropwise and the reaction was stirred at 0° C. for 1 h, then carefully quenched with 2-propanol. Sat'd aq. sodium bicarbonate (15 mL) was added and the mixture was extracted with EtOAc (4×20 mL). The combined extracts were washed with sat'd aq. sodium bicarbonate (1×20 mL), water (1×20 mL), and brine (1×20 mL), then dried over MgSO$_4$, filtered, and concentrated to afford compound 44A (145 mg, 60% over 2 steps).

Step B:

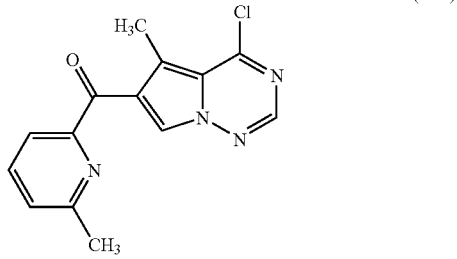

Ketone 44A (75 mg, 0.28 mmol) was placed in POCl$_3$ (4 mL) and heated to 100° C. overnight. The reaction was cooled to rt and the excess POCl$_3$ was evaporated under vacuum. The residue was dissolved in anhydrous DCM (10 mL) and added dropwise to a rapidly stirred solution of sat'd aq. sodium bicarbonate (50 ml) and DCM (50 mL) at 0° C. The mixture was stirred for 1 h, then the aqueous phase was extracted with DCM (3×50 mL). The organic phases were washed with sat'd aq. sodium bicarbonate (1×50 mL), water (1×50 mL), and brine (1×50 mL), then dried over MgSO$_4$, filtered, and concentrated to afford the chloride 44B (64 mg, 79%).

Step C:

Example 44

To a solution of compound 44B (53 mg, 0.18 mmol) in DMF (0.5 mL) was added compound 1A (84 mg, 0.44 mmol) and the solution was heated to 60° C. for 2 h. Water (5 mL) was added to precipitate the product, which was collected by filtration, washed with water, and allowed to air dry to afford Example 44 (34.2 mg, 41%).

HPLC ret. t. (min):3.39, MW: 452.48, LCMS[M+H]$^+$=453.

EXAMPLE 45

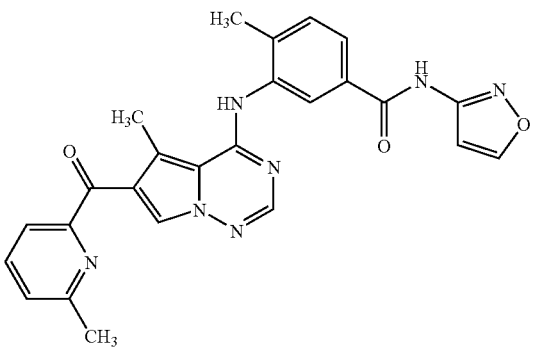

Example 45 WAS PREPARED following the same procedure as in Example 44, using a different benzamide in Step C. HPLC ret. t. (min):3.22, MW: 467.49, LCMS[M+H]$^+$=468.

EXAMPLE 46

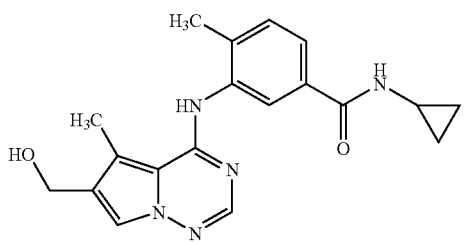

Step A:

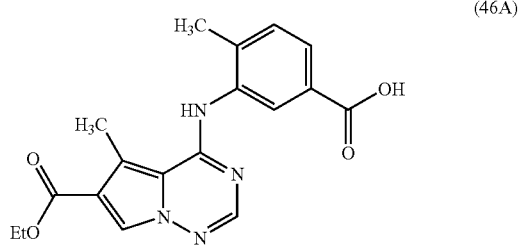

To a solution of the chloride having the formula

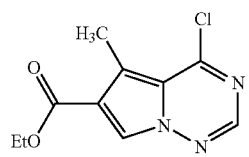

(10 g, 41.8 mmol) in DMF (60 mL) was added 3-amino-4-methyl-benzoic acid (6.3 g, 41.8 mmol) at rt. The reaction mixture was stirred for 16 h, poured into water (500 mL) and stirred rapidly for 1 h. The solids were filtered, washed with water (500 mL), and air dried to give the compound 46A (13.6 g, 92%) as a light pink solid. MS[M+H]$^+$=355.

Step B:

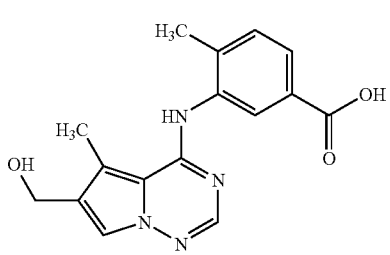

(46B)

To a solution of the compound 46A (1 g, 2.8 mmol) in DCM (6 mL) at −78° C. was added DIBAL-H (1M, 8.5 mL, 8.5 mmol) dropwise. The reaction was stirred for 2 h at −78° C., warmed to rt over 1.5 h, quenched with sat'd aq. NH$_4$Cl, then HCl (1 N) was added to adjust the pH to 4 and the solution was extracted with EtOAc. After drying of the organic phases and concentration, compound 46B was obtained as a pink solid (874 mg, 100%). HPLC ret. t. (min): 1.74, MW: 312.33, and LCMS[M+H]$^+$=313.

Step C:

Example 46

To a solution of compound 46B (1.8 g, 5.9 mmol) in DMF (10 mL) was added BOP (2.9 g, 615 mmol), cyclopropylamine (2 mL, 29.8 mmol). The reaction was stirred overnight at rt, then poured into water (60 mL) to precipitate the product. The solids were collected by filtration and purified by preparative HPLC to give Example 46 (1.5 g, 74%). HPLC ret. t. (min): 1.64, MW: 351.41, LCMS[M+H]$^+$=352.

EXAMPLE 47

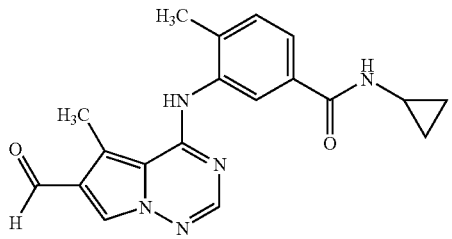

To a solution of Example 46 (1.5 g, 4.3 mmol) in THF (30 mL) at rt was added MnO$_2$ (5.4 g, 64 mmol). After stirring for 40 min., the reaction was completed. The product was collected by filtration and the precipitate was washed with acetonitrile. After drying of the filtrate and concentration, Example 47 was obtained as a yellow oil (1.5 g, quantitative). HPLC ret. t. (min): 2.52, MW: 349.40, LCMS[M+H]$^+$=350.

EXAMPLE 48

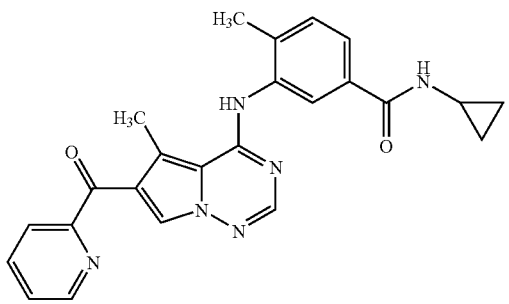

To a solution of 2-bromopyridine (54 μl, 0.57 mmol) and TMEDA (85 μl, 0.57 mmol) in THF (10 mL) at −78° C. was added nBuLi (1.6 M, 356 μl, 0.57 mmol) dropwise. To this solution was added Example 47 (50 mg, 0.14 mmol). The reaction was stirred for 0.5 h at −78° C., then warmed to rt and quenched with water. The mixture was extracted with EtOAc and the extracts were dried, filtered, and concentrated to afford the crude intermediate alcohol. To a solution of the crude alcohol in DCM (5 mL) at rt was added pyridinium chlorochromate (24.1 mg, 0.11 mmol). After stirring 1 h, the reaction was quenched with water (2 mL). The desired product was extracted with EtOAc and dried. After purification by preparative HPLC, Example 48 was obtained as yellow solid (24.6 mg, 40%). HPLC ret. t. (min): 2.95, MW: 426.48, LCMS[M+H]$^+$=427.

EXAMPLES 49-68

Compounds having the structure

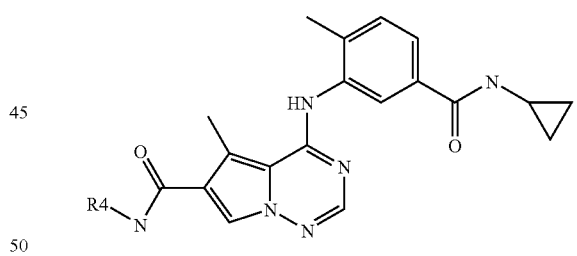

were prepared according to the procedure described for example 3 using the appropriate amine in place of n-butylamine.

| Ex. # | R$_4$ | (M + H)$^+$ | HPLC Ret. t. (min) |
|---|---|---|---|
| 49 | 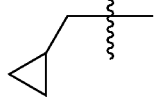 | 419.3 | 2.60 |

-continued
| Ex. # | R4 | (M + H)+ | HPLC Ret. t. (min) |
|---|---|---|---|
| 50 | 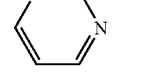 | 457.3 | 2.13 |
| 51 | 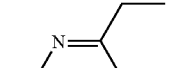 | 457.2 | 2.22 |
| 52 | 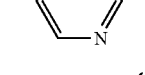 | 418.2 | 2.56 |
| 53 | H | 365.3 | 1.78 |
| 54 |  | 470.3 | 1.76 |
| 55 |  | 524.1 | 2.79 |
| 56 |  | 421.2 | 2.79 |
| 57 |  | 449.2 | 2.45 |
| 58 |  | 449.3 | 2.45 |
| 59 | 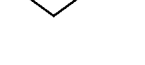 | 437.2 | 2.40 |
| 60 |  | 476.3 | 1.82 |
-continued
| Ex. # | R4 | (M + H)+ | HPLC Ret. t. (min) |
|---|---|---|---|
| 61 |  | 473.3 | 1.68 |
| 62 |  | 476.2 | 1.73 |
| 63 |  | 462.3 | 1.68 |
| 64 |  | 451.3 | 2.63 |
| 65 |  | 450.2 | 1.6 |
| 66 |  | 505.2 | 1.92 |
| 67 |  | 492.4 | 1.62 |
| 68 |  | 423.2 | 2.08 |

EXAMPLE 69

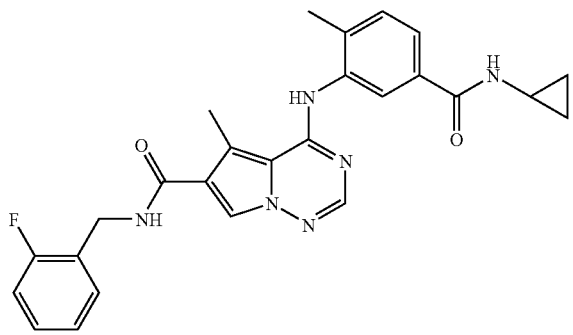

Step 1, Intermediate A:

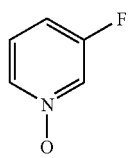

To a rt solution of 3-fluoropyridine (5.0 g) in dichloromethane (25 mL) and 30% aqueous hydrogen peroxide (10 mL) was added methyltrioxorhenium (25 mg) and the resulting mixture was stirred overnight. Manganese oxide (25 mg) was added and the solution was stirred at rt for an additional hour. Sodium chloride was added to saturate the aqueous portion and the layers were separated. The aqueous portion was extracted with additional dichloromethane (3×100 mL) and the combined organic extracts were dried over anhydrous sodium sulfate, filtered, and concentrated in vacuo to provided a light yellow oil which solidified upon standing to afford product A as a light yellow solid (4.92 g, 84%). HPLC Ret. Time: 0.30 min.

Step 2, Intermediate B:

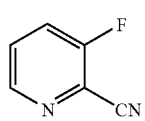

To solution of intermediate A (2.85 g, 25.2 mmol) in dichloromethane (25 ml) at rt was added trimethylsilylcyanide (10.0 mL, 75.6 mmol) and the mixture was refluxed for 10 h. After cooling to rt, saturated aqueous sodium bicarbonate solution (30 mL) was added and the resulting mixture was extracted with dichloromethane (3×150 mL). The combined organic extracts were dried over anhydrous sodium sulfate, filtered, and concentrated in vacuo to provided a light brown oil (4.60 g) as the crude product. This material was purified by flash column chromatography on silicas gel eluting with 30% ethyl acetate in hexane to provide a light tan oil which solidified upon standing to give product B as a light tan solid (2.48 g, 84). HPLC Ret. Time: 1.03 min.

Step 3, Intermediate C:

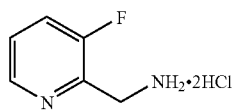

To intermediate B (1.40 g) in ethanol (50 ml) were successively added 10% palladium on carbon (500 mg) and concentrated hydrogen chloride (2.9 ml) and the resulting mixture was shaken under hydrogen (40 psi) for 20 h. The solution was filtered through a bed of celite and the filtrate was concentrated in vacuo to give 1.80 g of product C as a white solid. HPLC Ret. Time: 0.19 min.

Step 4, Title Compound:

A mixture of intermediate D (40 mg, 0.11 mmol), EDAC (25 mg, 0.13 mmol), and HOBt (16 mg, 0.12 mmol) in 0.3 mL of anhydrous DMF was stirred at rt for 2 hr then the amine hydrochloride C (0.13 mmol) and Hunig's base (38 µL, 0.22 mmol) were successively added. After stirring overnight at rt, the crude reaction mixture was subjected to purification by reverse-phase preparative HPLC to give the title compound.

EXAMPLES 70 AND 71

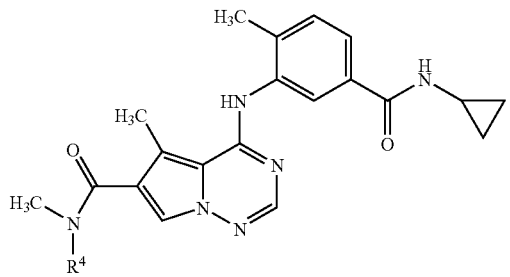

Examples 70 and 71 were prepared in the same manner as described for Examples 23-24.

| Ex. | R$_4$ | (M + H)$^+$ | HPLC Ret. t. (min) |
|---|---|---|---|
| 70 | ~O~ (methoxyethyl) | 437.3 | 2.19 |
| 71 | H$_3$C~ | 393.2 | 2.04 |

EXAMPLE 72

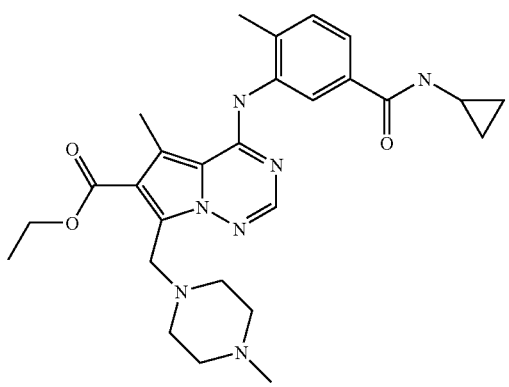

Step 1, Intermediate F:

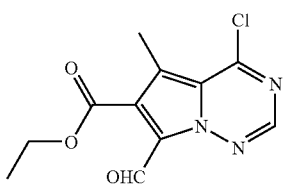

To intermediate E (10.0 g, 45.2 mmol) in POCl₃ (30 mL) at rt under argon was slowly added anhydrous DMF (7.0 mL, 90.4 mmol) and the resulting mixture was heated at 95° C. for 15 hours. After cooling to rt, the contents were slowly poured into a well-stirred mixture of 1 L of saturated aq. sodium bicarbonate solution and 200 mL of crushed ice. After allowing the heterogeneous slurry to stir at rt for 2.5 h, the resulting solid was collected by vacuum filtration and the solid was washed with two 150 mL portions of water then allowed to partially dry in the funnel. The solid was finally washed with two portions of dichloromethane (100 mL each) and the resulting organic filtrate was dried over anhydrous sodium sulfate and concentrated in vacuo to provide product F as a yellow solid (5.35 g, 47%) which was used directly without further purification. HPLC Ret. Time: 2.96 min.

Step 2, Intermediate G:

Intermediate F (3.19 g, 11.9 mmol) and the corresponding aniline hydrochloride (3.52 g, 15.5 mmol) in 40 mL of anhydrous DMF were stirred at rt overnight then diluted with 200 mL of water and 30 mL of saturated aqueous sodium bicarbonate solution. After stirring at rt for 1 h, the resulting solid was collected by vacuum filtration, washed with water, and dried in vacuo to afford product G as an orange solid (4.2 g, 84%) which was used directly without further purification. HPLC Ret. Time: 2.97 min. MH⁺=422.1 (m/z).

Step 3, Title Compound:

To intermediate G (0.8 g, 1.90 mmol) in anhydrous THF (10 mL) at rt under argon were successively added 1-methylpiperazine (0.24 g, 2.47 mmol) and NaBH(OAc)₃ (1.21 g, 5.70 mmol) followed by stirring at rt for 3 hour. The reaction mixture was quenched by addition of 50 mL of methanol followed by stirring for an additional hour at rt then concentrated and partitioned between 50 mL of saturated aqueous sodium bicarbonate solution and 200 ml of ethyl acetate. The layers were separated and the aqueous portion was saturated with sodium chloride and extracted with additional ethyl acetate (4×100 mL). The combined organic extracts were dried over anhydrous sodium sulfate and concentrated in vacuo to give the title compound as a light yellow solid (1.02 g, yield 89%). HPLC Ret. Time: 2.25 min. MH⁺ (m/z) 506.2.

EXAMPLES 73-80

The following compounds were prepared in the same manner as described for Example 72.

| Example | Structure | retention time | MH+ |
|---|---|---|---|
| 73 | 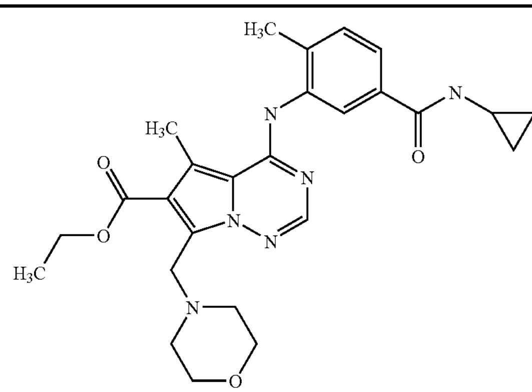 | 2.23 | 493.2 |

-continued

| Example | Structure | retention time | MH+ |
|---------|-----------|----------------|-----|
| 74 | 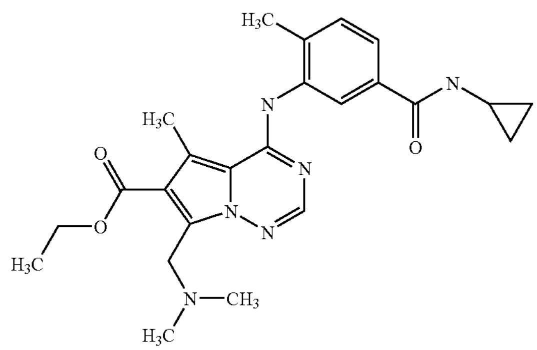 | 2.26 | 451.2 |
| 75 | 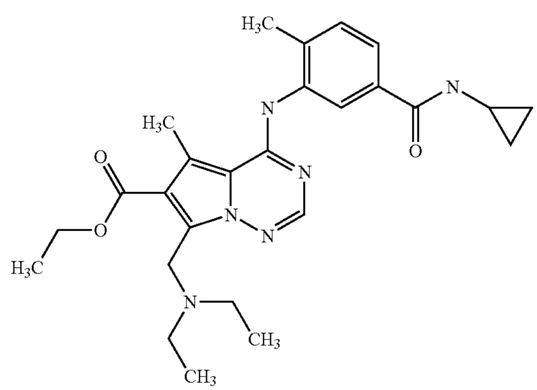 | 2.40 | 479.2 |
| 76 | 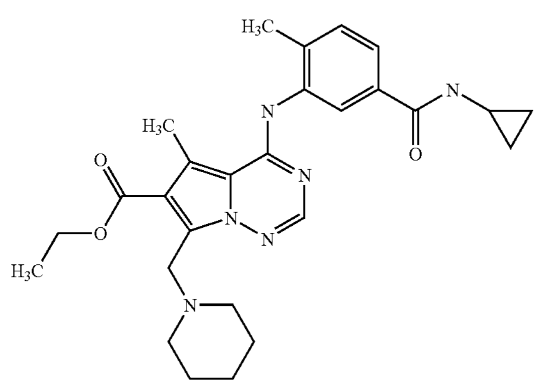 | 2.38 | 491.2 |
| 77 | 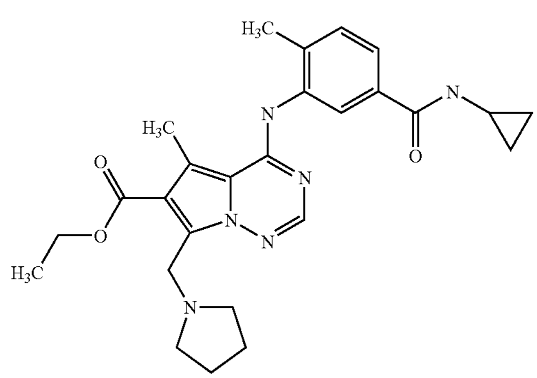 | 2.32 | 477.3 |

-continued
| Example | Structure | retention time | MH+ |
|---------|-----------|----------------|-----|
| 78 | 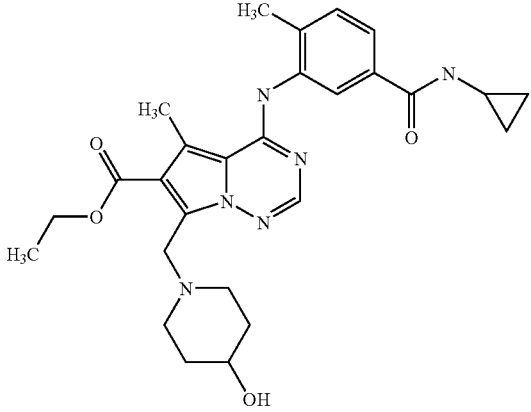 | 2.26 | 507.3 |
| 79 | 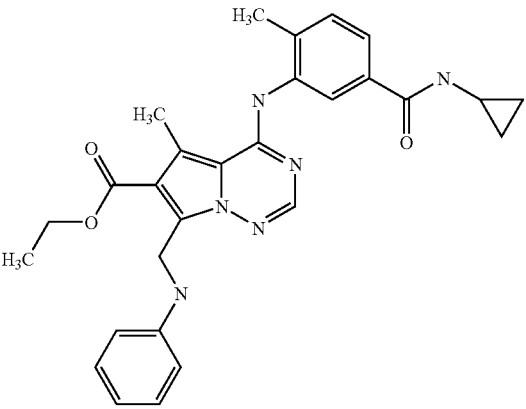 | 3.29 | 499.3 |
| 80 | 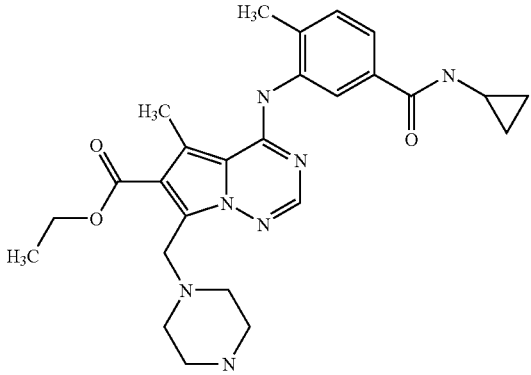 | 2.13 | 492.2 |

EXAMPLES 81-83

Step 1, Intermediate H

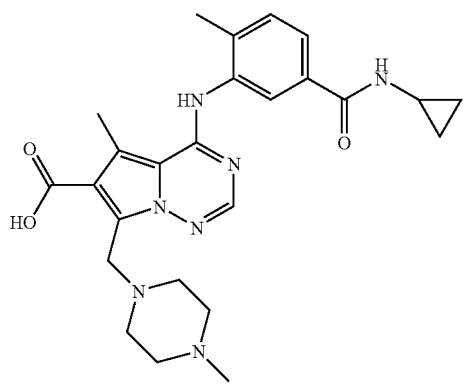

To compound 4 (0.80 g, 1.67 mmol) in methanol (10 mL) at rt was added 6N aqueous sodium hydroxide solution (1.8 mL, 10.8 mmol) and the mixture was refluxed for 20 h. After cooling to rt, the methanol was removed in vacuo and the mixture was brought to pH 6 with 1N HCl and freeze dried to give 1.02 g of the crude product H as a pale yellow solid containing residual sodium chloride. This material was used without further purification in the subsequent reaction. HPLC Ret. Time: 1.65 min. MH$^+$ (m/z) 478.14.

Step 2, Title Compounds

Intermediate H (40 mg, 0.083 mmol), EDAC (25 mg, 0.13 mmol), and HOBt (16 mg, 0.12 mmol) were stirred at rt for 2 hr then the corresponding amine RNH$_2$ (0.13 mmol) and Hunig's base (38 μL, 0.22 mmol) were successively added followed by stirring overnight at rt. The resulting mixture was subjected to reverse-phase preparative HPLC to obtain the title compounds.

| Ex. | Structure | retention time | MH+ |
|---|---|---|---|
| 81 | 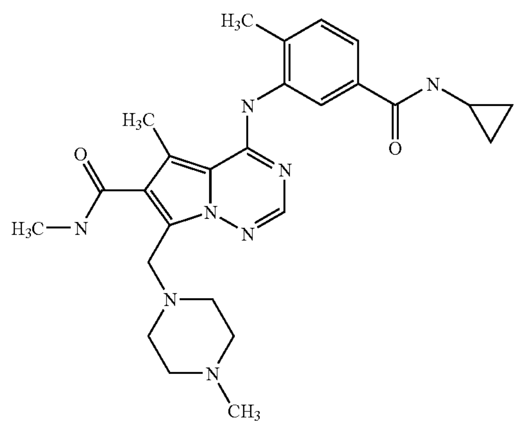 | 1.43 | 491.2 |
| 82 | 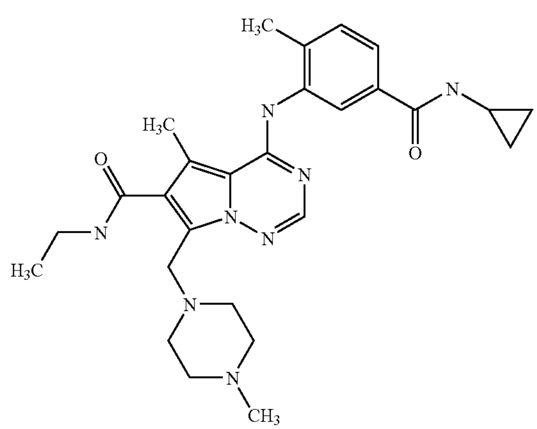 | 1.61 | 505.2 |

| Ex. | Structure | retention time | MH+ |
|---|---|---|---|
| 83 | (structure) | 1.82 | 519.2 |

EXAMPLES 84-86

Examples 84-86 were prepared from intermediate H as follows:

Intermediate H (40 mg, 0.083 mmol), EDAC (25 mg, 0.13 mmol), and HOBt (16 mg, 0.12 mmol) were stirred at rt for 2 hr then the corresponding alcohol ROH (1 mL) and Hunig's base (38 μL, 0.22 mmol) were successively added followed by stirring overnight at rt. The resulting mixture was subjected to reverse-phase preparative HPLC to obtain the title compounds.

| Example | Structure | retention time | MH + |
|---|---|---|---|
| 84 | (structure) | 2.00 | 492.3 |
| 85 | (structure) | 2.54 | 520.6 |

| Example | Structure | retention time | MH+ |
|---|---|---|---|
| 86 | 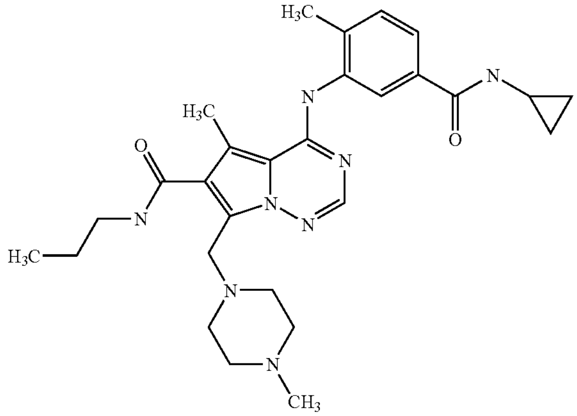 | 2.45 | 520.3 |

EXAMPLE 87

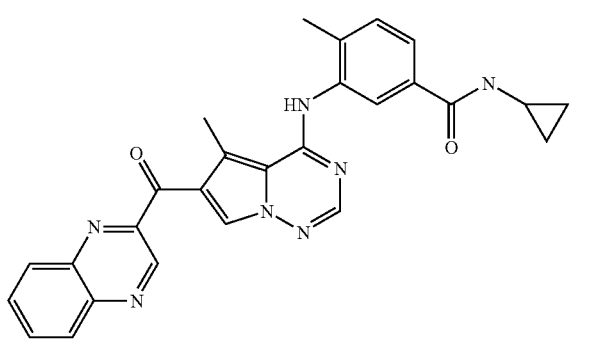

To a solution of aldehyde [Example 47] (0.040 g, 0.114 mmol) in DMF (1 mL) at rt was added 2-chloroquinoxaline (0.0188 g, 0.114 mmol), sodium hydride (0.0054 mg, 0.138 mmol), N,N'-dimethylimidazolium iodide (0.084 mg, 0.038 mmol), and p-toluenesulfinic acid, sodium salt (0.008 mg, 0.044 mmol). After stirring overnight at rt, the solution was heated to 80° C. and additional portions of N,N'-dimethylimidazolium iodide and sodium hydride were added. After 1 h the reaction was cooled to rt and water was added. The resulting precipitate was collected and further purified by preparative reverse phase HPLC to afford the title compound (0.003 g). HPLC ret. t. (min): 3.61, MW: 477.5, LCMS[M+H]$^+$=478.

EXAMPLE 88

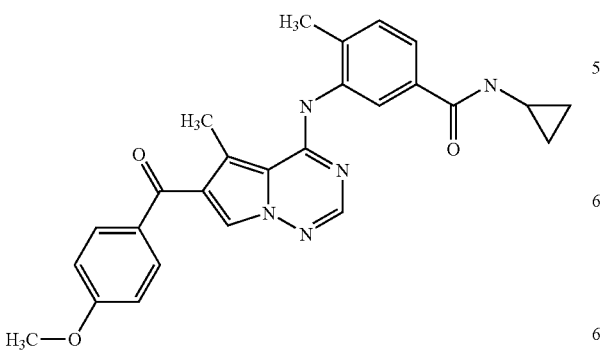

Step A:

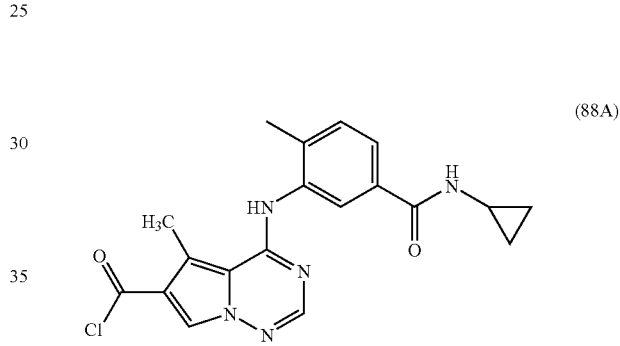

(88A)

To Example 2 (500 mg) was added thionyl chloride (6 mL) at rt. After stirring for 30 min at rt, the thionyl chloride was evaporated under reduced pressure affording 88A as a white solid (HCl Salt, 580 mg)

Step B:

To a solution of acid chloride 88A (0.020 g, 0.048 mmol) and anisole (0.026 mL, 0.238 mmol) in 1,2-dichloroethane (1 mL) at 0° C. was added aluminum trichloride (0.0095 g, 0.071 mmol). After 2 hr at 0° C. the solution was warmed to rt and additional aluminum trichloride (0.140 g) was added. After stirring at rt overnight, the reaction was quenched with water (0.2 mL) and the solvent was evaporated. The residue was recrystallized from a minimum of methanol/water and collected by filtration to afford the title compound (0.0065 g).). HPLC ret. t. (min): 3.29, MW: 455.5, LCMS[M+H]$^+$=456.

EXAMPLES 89-96

The following compounds were obtained in a manner similar to Example 88.

| Ex. | Structure | MW | HPLC ret. t (min) | MS (MH+) |
|---|---|---|---|---|
| 89 | 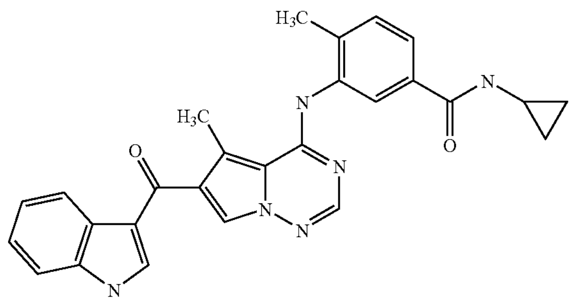 | 464.5 | 3.00 | 465 |
| 90 | 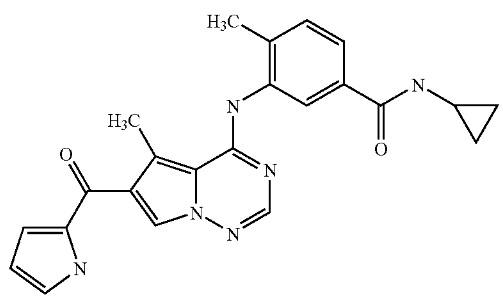 | 414.5 | 2.84 | 415 |
| 91 | 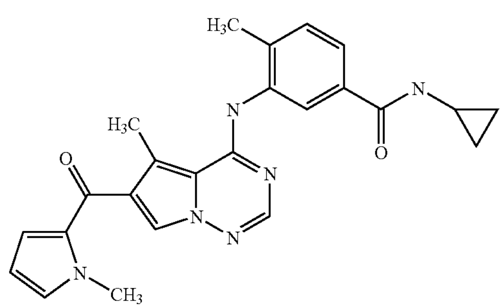 | 428.5 | 3.08 | 429 |
| 92 | 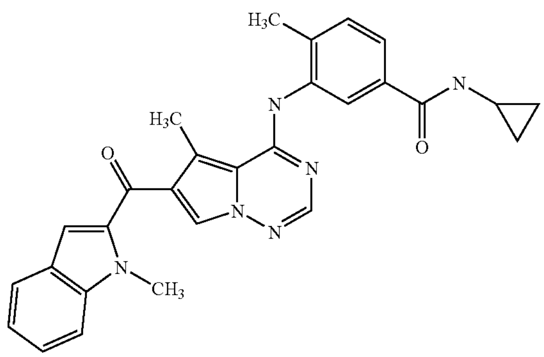 | 478.6 | 3.19 | 478 |

-continued

| Ex. | Structure | MW | HPLC ret. t (min) | MS (MH+) |
|---|---|---|---|---|
| 93 | 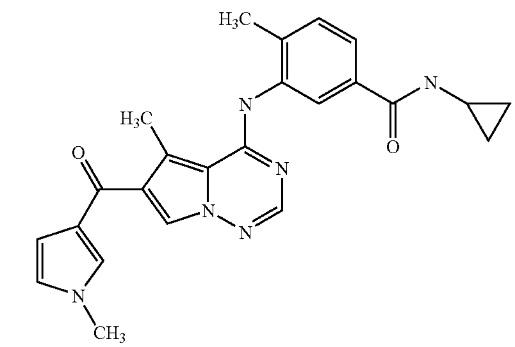 | 428.5 | 2.68 | 429 |
| 94 | 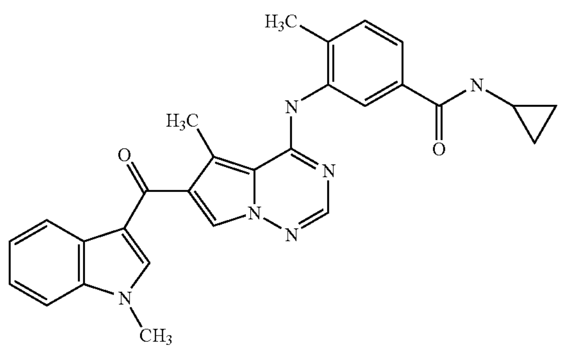 | 478.6 | 2.89 | 478 |
| 95 | 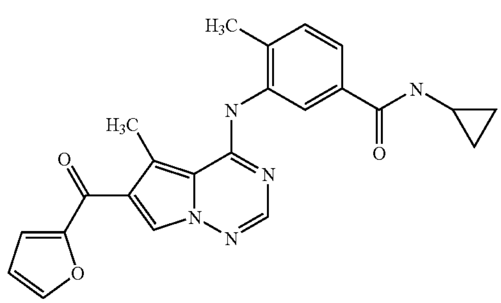 | 415.5 | 2.94 | 416 |
| 96 | 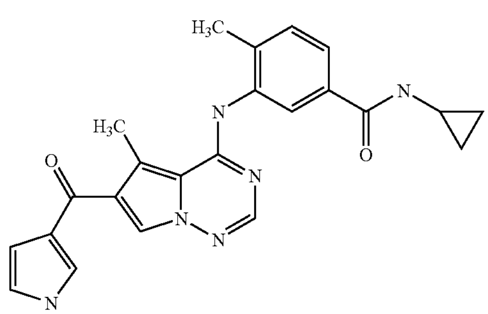 | 414.5 | 2.49 | 415 |

EXAMPLE 97

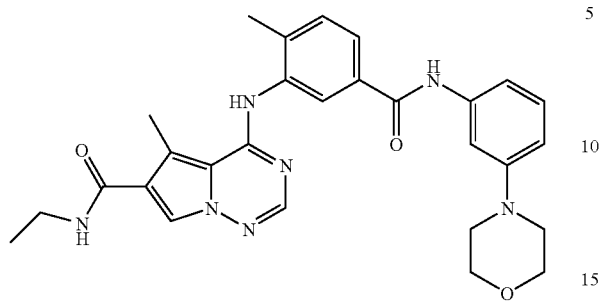

Step A:

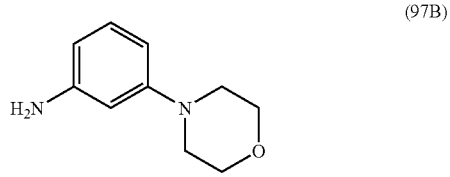
(97A)

A mixture of 3-fluoronitrobenzene (10.0 g, 71 mmol), morpholine (27 mL), and DMSO (118 mL) was stirred at 110° C. for 36 h then cooled to rt and poured into 800 mL of water. The resulting mixture was stirred for 20 min and the solid was collected by vacuum filtration and dried in vacuo to afford 13.6 g (92%) of 97A as a bright yellow solid.). LCMS (M+H$^+$)=209.1. HPLC Ret. time: 1.48 min.

Step B:

(97B)

To a slurry of 97A (13.6 g, 65 mmol) in methanol (225 mL) at rt were successively added ammonium formate (20.5 g, 326 mmol) and 10% palladium on charcoal (2.0 g) and the mixture was stirred at rt for 48 h. The resulting mixture was filtered through a pad of celite and the clear filtrate was concentrated in vacuo and the resulting residue was partitioned between water (50 mL) and ethyl acetate (150 mL). The layers were separated and the aqueous portion was extracted with additional ethyl acetate (2×50 mL). The combined extracts were washed with brine (50 mL), dried over anhydrous sodium sulfate, filtered, and concentrated in vacuo to afford 10.8 g (93%) of 97B as a tan solid. LCMS (M+H$^+$)=179.2.

Step C:

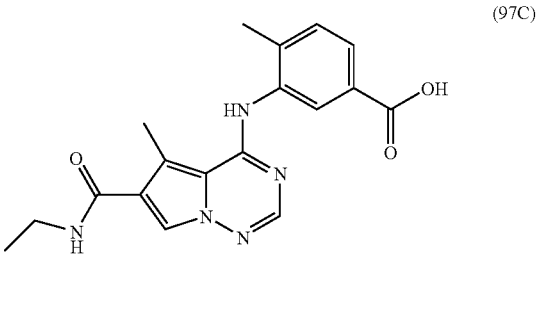
(97C)

To a slurry of 2.0 g (4.2 mmol) of the compound

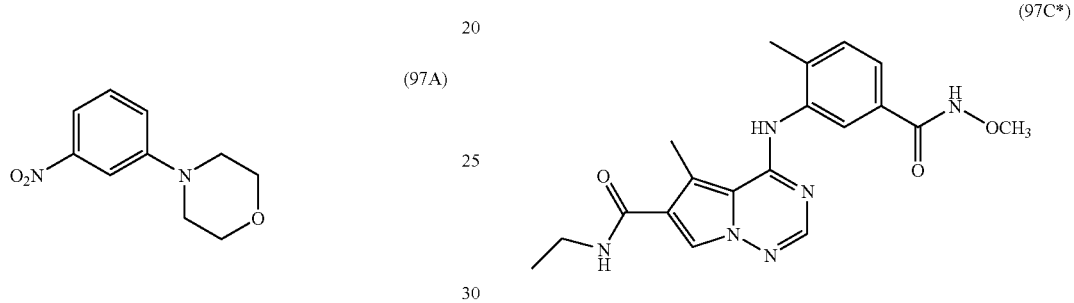
(97C*)

(synthesized as described in WO 02/40486) in 12 mL of anhydrous methanol was added 18 mL of a 4 N solution of anhydrous hydrochloric acid in dioxane at room temperature. The resulting clear solution was stirred at room temperature for 16 h and the reaction mixture was concentrated in vacuo. The resulting oil was dissolved in 16 mL of 1.5 N aqueous potassium hydroxide solution and heated to 50° C. for 3 h. After cooling to room temperature, the mixture was diluted with 50 mL of water and 10% aqueous hydrochloric acid was added until pH was approximately 3 or 4. The resulting precipitated product was collected by vacuum filtration and washed with 50 mL of water and dried in vacuo to afford 1.47 g (99%) of 97C as a white solid. An analytical sample of 97C was prepared by recrystallization from 10% aqueous acetonitrile. $^1$H NMR (CD$_3$OD): δ 8.21 (br s, 1H), 8.11 (br s, 1H), 7.89-7.91 (m, 2H), 7.67 (br s, 1H), 7.44 (d, 1H), 3.40 (q, 2H), 2.86 (s, 3H), 2.36 (s, 3H), 1.25 (s, 3H). LCMS (M+H$^+$)=354.2. HPLC: 2.24 min.

Step D: Title Compound

A mixture of 97C (40 mg, 0.11 mmol), HATU (65 mg, 0.17 mmol), diisopropylamine (20 μL, 0.11 mmol), and 97B (39 mg, 0.22 mmol) in 0.3 mL of N-methylpyrrolidinone was heated at 80° C. for 16 h and the reaction mixture was purified by reverse-phase preparative HPLC to afford 41 mg (74%) of the title compound as a light tan solid. $^1$H NMR (CD$_3$OD w/TFA): δ 8.28 (s, 1H), 8.19 (s, 1H), 8.16 (d, 1H), 8.11 (d, 1H), 7.84 (s, 1H), 7.71 (d, 1H), 7.58 (t, 2H), 7.47 (d, 1H), 3.44 (q, 2H), 2.94 (s, 3H), 2.47 (s, 3H), 1.26 (t, 3H). LCMS (M+H$^+$)=497.5. HPLC Ret. time: 3.30 min.

EXAMPLE 98

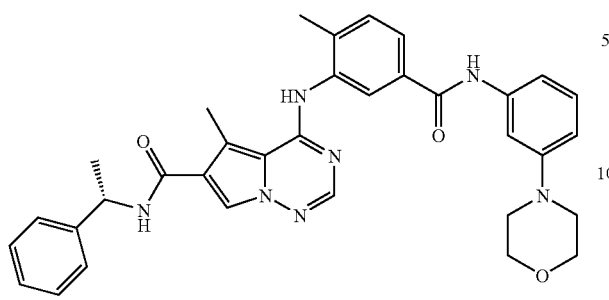

The title compound was prepared as described for the preparation of Example 97 by substituting 97C* in Step C with Example compound 70 in WO 02/40486. LCMS (M+H⁺)=590.2. HPLC Ret. time: 3.26 min.

EXAMPLE 99

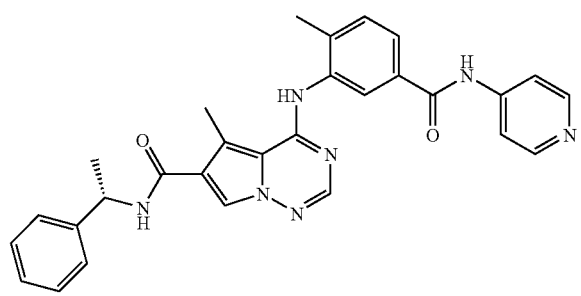

The title compound was prepared as described for the preparation of Example 97 by substituting 97C* in Step C with Example compound 70 in WO 02/40486 and by substituting 97B with 4-aminopyridine in Step D. LCMS (M+H⁺)=506.4. HPLC Ret. time: 2.95 min.

EXAMPLE 100

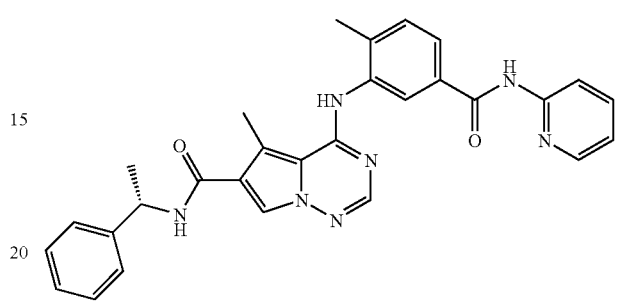

The title compound was prepared as described for the preparation of Example 97 by substituting 97C* in Step C with Example compound 70 in WO 02/40486 and by substituting 97B with 2-aminopyridine in Step D. LCMS (M+H⁺)=590.2. HPLC Ret. Time: 3.01 min.

EXAMPLES 101-104

The following compounds were prepared in a similar manner as that described for Example 100.

| EX # | Structure | (M + H)⁺ | HPLC Ret. t. (min) |
|---|---|---|---|
| 101 | 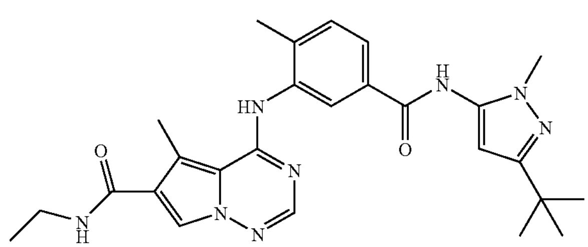 | 489.5 | 3.54 |
| 102 | 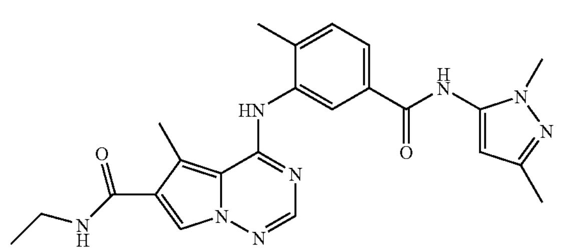 | 446.3 | 2.94 |

| EX # | Structure | (M + H)+ | HPLC Ret. t. (min) |
|---|---|---|---|
| 103 | 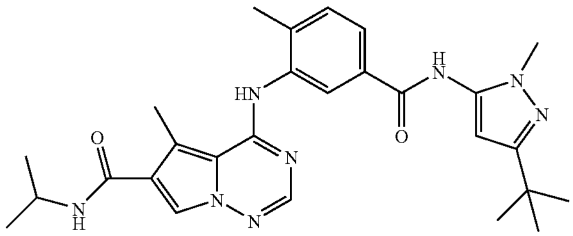 | 503.3 | 3.64 |
| 104 | 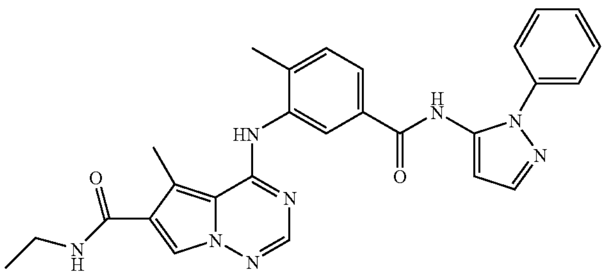 | 496.1 | 3.19 |

EXAMPLE 105

Step A:

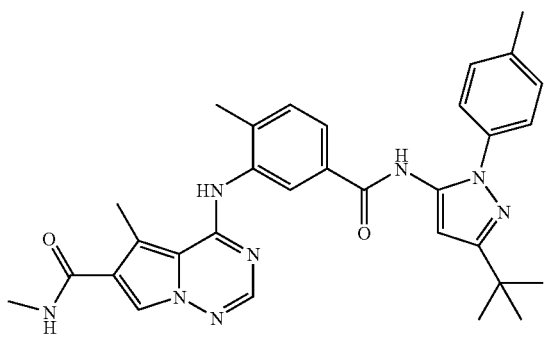

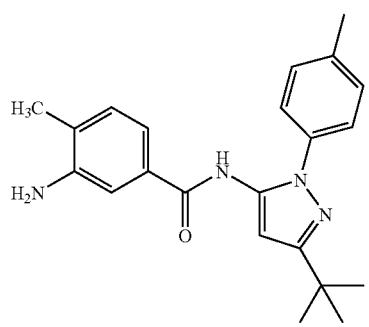

A solution of 3-nitro-4-methyl benzoyl chloride (215 mg, 1.08 mmol) and N-tolyl-3-tert-butyl-5-aminopyrazole hydrochloride (287 mg, 1.08 mmol) in dichloromethane (5 mL) was added DIPEA (0.38 mL, 2.2 mmol) and the reaction mixture stirred for 2 h. The reaction was concentrated to an oil which was dissolved in EtOAc (50 mL) and washed consecutively with aq NaHCO₃, water, 1N HCl, water and brine. The organic layer was dried over Na₂SO₄, filtered and concentrated to an oil which was purified via column chromatography (10% then 30% EtOAc/hexane) to give the nitro amide (420 mg, 99%).

The above solids was dissolved in EtOH (156 mL) and added 5% Pd—C (wet, 10035 mg) and evacuated and back filled under a hydrogen balloon. The reaction was stirred for 32 h, filtered and concentrated to a white solid which was used without further purification (403 mg, 99%), LRMS 363.6 (M+H).

Step B: Title Compound

The title compound was prepared from the intermediate obtained in Step A following the procedure described for Examples 1 and 2.

EXAMPLE 106

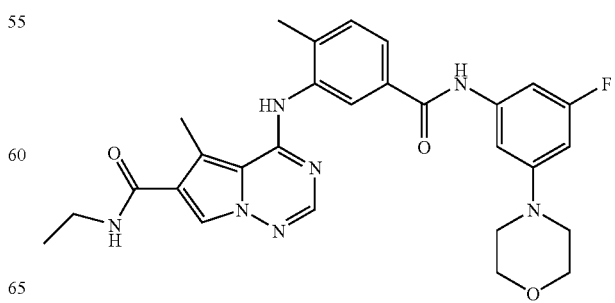

Step A:

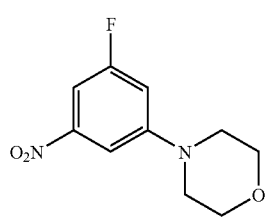
(106A)

A mixture of 3,5-difluoronitrobenzene (4.1 g, 26 mmol) and morpholine (11 mL) was heated to 100° C. for 16 h then cooled to rt overnight. The resulting solid was collected by vacuum filtration and dissolved into methylene chloride (250 mL) and the solution was successively washed with 1N aqueous HCl (2×100 mL) and brine (100 mL), then dried over anhydrous sodium sulfate, filtered, and concentrated in vacuo to afford 4.0 g (69%) of 106A as a yellow solid. LCMS (M+H$^+$)=227.2.

HPLC Ret. time: 2.85 min.

Step B:

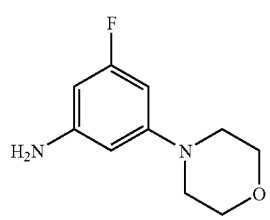
(106B)

A mixture of 106A (4.0 g, 18 mmol) and 10% palladium on charcoal (0.4 g) in 150 mL of ethanol was stirred under an atmosphere of hydrogen at rt for 16 h. The resulting mixture was filtered through a pad of celite and the filtrate was concentrated in vacuo to afford 3.4 g (96%) of 106B as an off-white solid. LCMS (M+H$^+$)=197.1.

HPLC Ret. time: 0.92 min.

Step C: Title Compound

The title compound was prepared as described for the preparation of Example 97 by substituting 97B with 106B in Step D. LCMS (M+H$^+$)=532.0. HPLC Ret. time: 3.04 min.

EXAMPLE 107

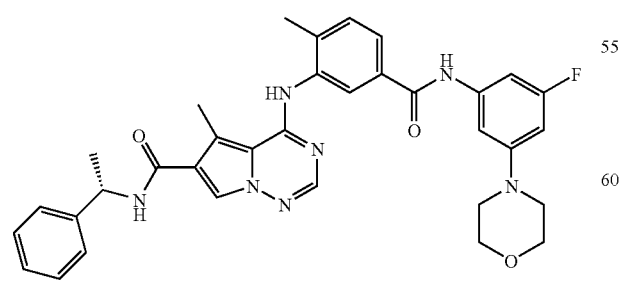

The title compound was prepared as described for the preparation of Example 97 by substituting 97C* in Step C with Example compound 70 in WO 02/40486 and by substituting 97B with 106B in Step D. LCMS (M+H$^+$)=608.5. HPLC Ret. time: 3.52 min.

EXAMPLE 108

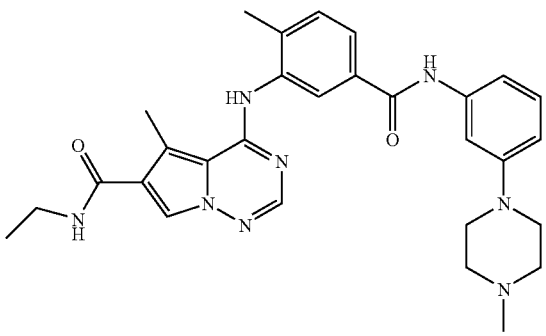

Step A:

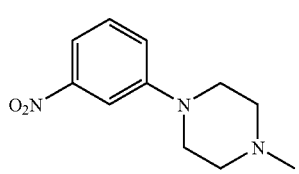
(108A)

A mixture of 3-fluoronitrobenzene (1.0 g, 7.1 mmol) and 1-methylpiperizine (5 mL) was heated to 130° C. for 3 days. After cooling to rt, the mixture was diluted with water (100 mL) and extracted with ethyl acetate (4×40 mL). Concentration of the combined extracts yielded a dark red oil which was dissolved in dichloromethane (75 mL) and washed with 1 N aqueous HCl (3×25 mL). The combined acidic aqueous extracts were neutralized to pH~7 by addition of 3 N aqueous potassium hydroxide solution and extracted with dichloromethane (3×40 mL). The combined extracts were washed with brine (40 mL), dried over anhydrous sodium sulfate, filtered, and concentrated in vacuo to afford 0.92 g (59%) of 108A as a dark brown oil. LCMS (M+H$^+$)=222.1. HPLC Ret. time: 0.97 min.

Step B:

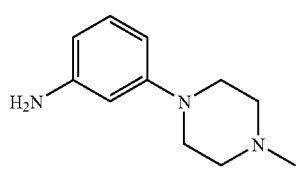
(108B)

108B was prepared as described for the preparation of 106B. LCMS (M+H$^+$)=192.3. HPLC Ret. time: 0.17 min.

Step C: Title Compound

The title compound was prepared as described for the preparation of Example 97 by substituting 97B with 108B in Step D. LCMS (M+H$^+$)=527.3. HPLC Ret. time: 2.14 min.

EXAMPLE 109

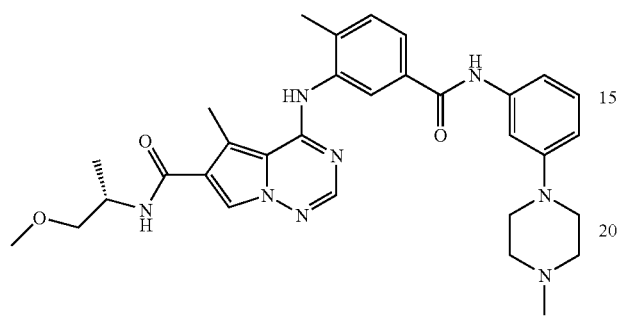

The title compound was prepared as described for the preparation of Example 97.

LCMS (M+H$^+$)=571.4. HPLC Ret. time: 2.22 min.

EXAMPLE 110

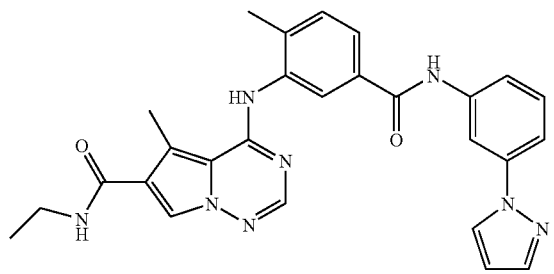

Step A:

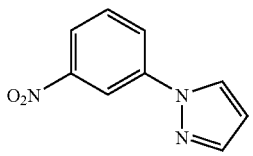
(110A)

A mixture of 3-fluoronitrobenzene (1.0 g, 7.1 mmol), pyrazole (0.58 g, 8.5 mmol), and cesium carbonate (2.8 g, 8.5 mmol) in 4 mL of N-methylpyrrolidinone was heated to 100° C. for 17 h. After cooling to rt, the mixture was diluted with water (75 mL) and extracted with ethyl acetate (3×75 mL) and the combined extracts were washed with brine (20 mL), dried over anhydrous sodium sulfate, filtered, and concentrated in vacuo to afford 1.7 g (71%) of 110A as a dark red oil. LCMS (M+H$^+$)=190.1.

HPLC Ret. time: 2.42 min.

Step B:

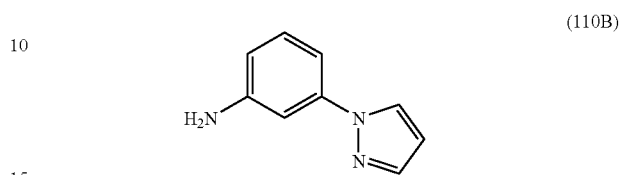
(110B)

A mixture of 110A (0.95 g, 5.0 mmol) and 10% palladium on charcoal (0.27 g) in 10 mL of ethyl acetate was stirred at rt under an atmosphere of hydrogen for 17 h. The resulting mixture was filtered through a pad of celite and the resulting filtrate was concentrated in vacuo to afford 0.73 g (91%) of 110B as a pale yellow oil. LCMS (M+H$^+$)=160.1. HPLC Ret. time: 0.74 min.

Step C: Title Compound

The title compound was prepared as described for the preparation of Example 97 by substituting 97B with 110B in Step D. LCMS (M+H$^+$)=495.3. HPLC Ret. time: 2.91 min.

EXAMPLE 111

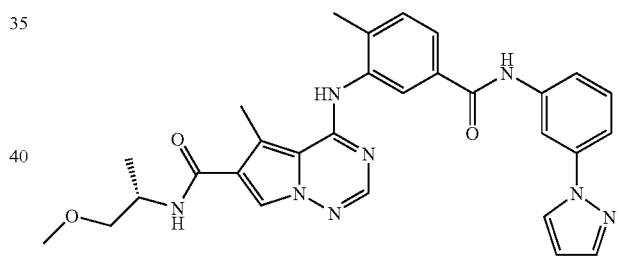

The title compound was prepared as described for the preparation of Example 97.

LCMS (M+H$^+$)=539.3. HPLC Ret. time: 2.97 min.

EXAMPLE 112

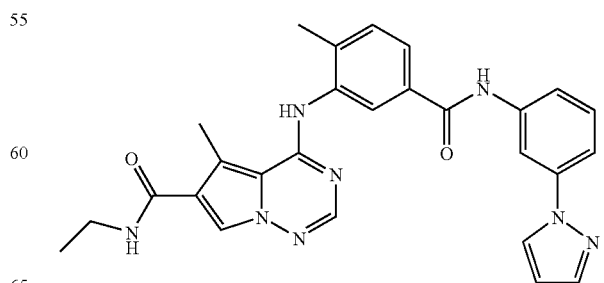

Step A:

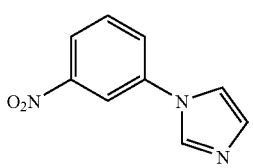
(112A)

A mixture of 3-bromonitrobenzene (1.0 g, 5.0 mmol), imidazole (0.51 g, 7.5 mmol), 1,10-phenanthroline (0.89 g, 5.0 mmol), dibenzylideneacetone (0.06 g, 0.25 mmol), cesium carbonate (1.8 g, 5.5 mmol), and copper(II) triflate benzene adduct (0.12 g, 0.25 mmol) in 1 mL of xylenes was heated at 120° C. for 36 h. After cooling to rt, the mixture was diluted with dichloromethane (100 mL) and washed with saturated aqueous ammonium chloride solution (2×50 mL) and 1 N aqueous HCl (2×75 mL). The combined acidic aqueous portions were neutralized to pH~7 by adding 3N aqueous KOH and then extracted with dichloromethane (3×40 mL). The organic extracts were washed with brine (30 ml), dried over anhyd. sodium sulfate, filtered, and concentrated in vacuo to afford 0.55 g (58%) of 112A as a dark red semi-solid.
LCMS (M+H$^+$)=190.1. HPLC Ret. time: 0.44 min.

Step B:

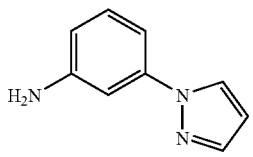
(112B)

A mixture of 112A (0.55 g, 2.9 mmol) and 10% palladium on charcoal (0.15 g) in 15 mL of methanol was stirred at rt under an atmosphere of hydrogen for 17 h. The resulting mixture was filtered through a pad of celite and the resulting filtrate was concentrated in vacuo to afford 0.36 g (77%) of 112B as a pale yellow solid. LCMS (M+H$^+$)=160.1. HPLC Ret. time: 0.19 min.

Step C: Title Compound

The title compound was prepared as described for the preparation of Example 97 by substituting 97B with 112B in Step D. LCMS (M+H$^+$)=495.2. HPLC Ret. time: 2.12 min.

EXAMPLE 113

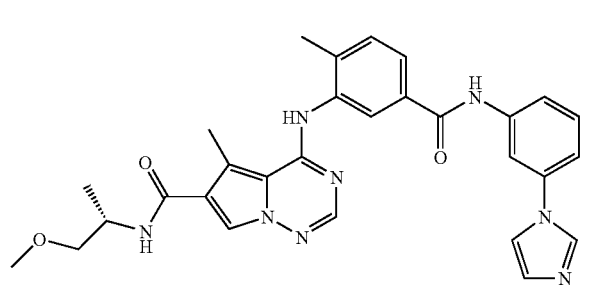

The title compound was prepared as described for the preparation of Example 97.
LCMS (M+H$^+$)=539.3. HPLC Ret. time: 2.32 min.

EXAMPLE 114

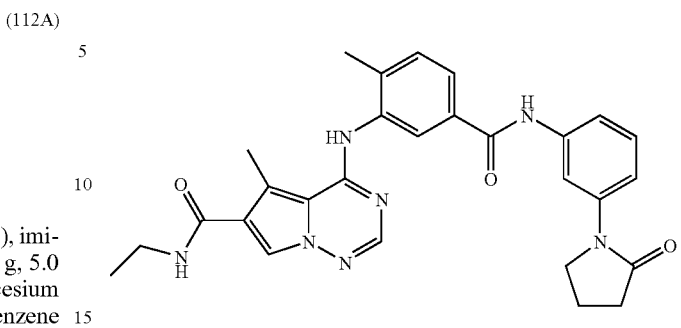

Step A:

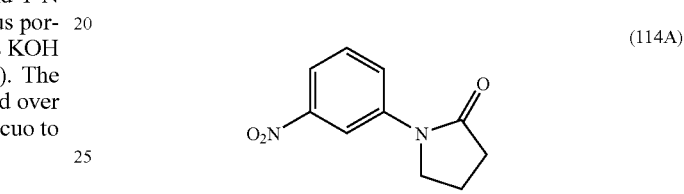
(114A)

To a mixture of 3-bromonitrobenzene (1.0 g, 5.0 mmol), 2-pyrrolidinone (0.50 g, 5.9 mmol), potassium carbonate (1.37 g, 9.9 mmol), and trans-1,2-cyclohexanediamine (0.06 mL, 0.50 mmol) were successively added 2.5 mL of anhydrous 1,4-dioxane and copper (I) iodide (94 mg, 0.50 mmol) and the contents were heated to 110° C. for 24 h. After cooling to rt, the mixture was partitioned between water (50 mL) and ethyl acetate (75 mL). The aqueous layer was extracted with additional ethyl acetate (2×50 mL) and the combined extracts were washed with brine (30 ml), dried over anhyd. sodium sulfate, filtered, and concentrated in vacuo to afford the crude product as a dark brown solid. Purification by flash chromatography on silica gel using a gradient elution from 70% ethyl acetate in hexanes to 100% ethyl acetate gave 0.68 g (68%) of 114A as a pale yellow solid after concentration in vacuo. LCMS (M+H$^+$)=208.1.

HPLC Ret. time: 2.11 min.

Step B:

(114B)

A mixture of 114A (0.68 g, 3.3 mmol) and 10% palladium on charcoal (0.35 g) in 10 mL of methanol was stirred at rt under an atmosphere of hydrogen for 17 h. The resulting mixture was filtered through a pad of celite and the resulting filtrate was concentrated in vacuo to afford 0.55 g (95%) of 114B as an off-white solid. LCMS (M+H$^+$)=177.1. HPLC Ret. time: 0.34 min.

Step C: Title Compound

The title compound was prepared as described for the preparation of Example 97 by substituting 97B with 114B in Step D. LCMS (M+H⁺)=512.2. HPLC Ret. time: 2.68 min.

EXAMPLE 115

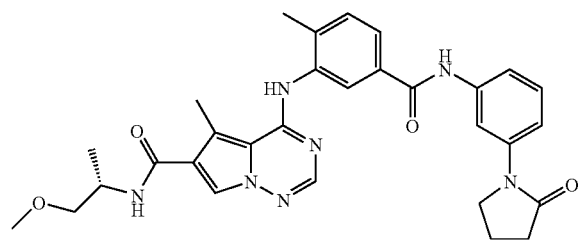

The title compound was prepared as described for the preparation of Example 97.

LCMS (M+H⁺)=556.3. HPLC Ret. time: 2.77 min.

EXAMPLE 116

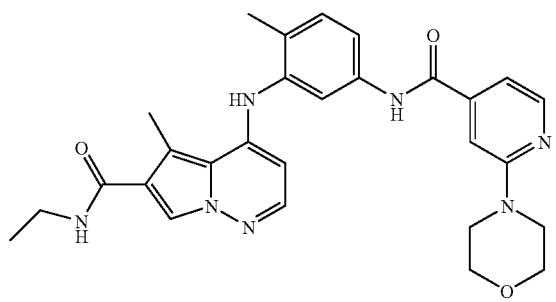

Step A:

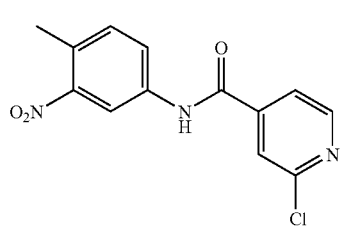
(116A)

To a solution of 4-methyl-3-nitroaniline (3.93 g, 25.8 mmol) in 200 mL of dichloromethane at rt under argon was added 2-chloropyridine-4-carbonyl chloride (5.00 g, 28.4 mmol) followed by triethylamine (8.0 mL, 56.7 mmol) via syringe and the resulting mixture was stirred for 2 h. The solvent removed in vacuo and the residue was triturated with 20 mL of dichloromethane and the solid was collected by filtration to yield 7.50 g (99.6%) of 116A as a yellow solid. HPLC Ret. Time: 3.13 min. MH⁺ (m/z) 292.3.

Step B:

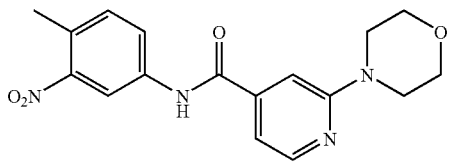
(116B)

To 116A (7.50 g) was added 50 ml of morpholine and the mixture was heated to 100° C. under argon for 20 h then cooled to rt and slowly poured into ice-water (600 mL) with stirring. This mixture was stirred at rt for 15 min and the resulting solid was collected by filtration and dried in vacuo to afford 5.50 g (62.5%) of 116B as a light yellow solid. HPLC Ret. Time: 2.39 min. MH⁺ (m/z) 343.4.

Step C:

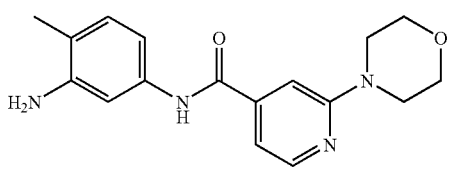
(116C)

To compound 116B (1.50 g) in absolute ethanol (100 mL) was added 10% palladium on carbon (200 mg) and the mixture was shaken under hydrogen (30 psi) for 6 h. The solution was filtered through a pad of celite and the solvent was removed in vacuo to give 1.33 g of 116C as a light yellow solid. HPLC Ret. Time: 0.94 min.

MH⁺ (m/z) 313.3.

Step D:

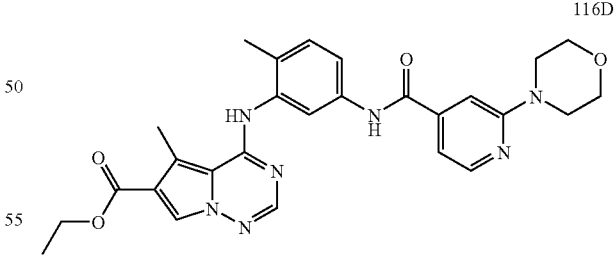
116D

Compound 116C (0.20 g, 0.58 mmol) and 4-chloro-5-methylpyrrolotriazine-6-ethylcarboxylate (0.14 g, 0.58 mmol) in anhydrous DMF was stirred at rt for 20 h. The reaction was diluted with ice-cold water and saturated aqueous sodium bicarbonate and the resulting precipitated solid was collected and washed with water to give 0.30 g of 116D as a light yellow solid. HPLC Ret. Time: 2.96 min. MH⁺ (m/z) 516.2.

Step E:

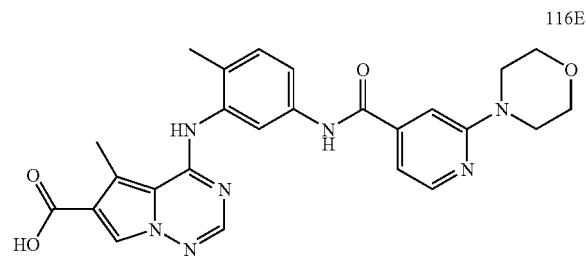

116D (0.30 g, 0.58 mmol) in 3 mL of 1N sodium hydroxide and 2 mL of methanol was heated at 60° C. for 4 h. Methanol was removed in vacuo and the aqueous mixture was acidified with 1N aqueous HCl to pH~2. The resulting solid was collected and washed with water to give 0.24 g of 116E as a pale yellow solid. HPLC Ret. time: 2.26 min. MH+ (m/z) 488.2.

Step F:

Title Compound

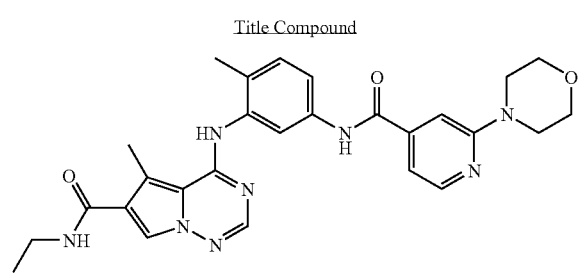

116E (40 mg, 0.082 mmol), EDAC (19 mg, 0.098 mmol), HOBt (13 mg, 0.098 mmol), and Hunig's base (43 μL, 0.25 mmol) were stirred at rt for 0.5 h and ethylamine hydrochloride (13 mg, 0.16 mmol) was added followed by stirring overnight. The crude reaction mixture was purified by reverse-phase preparative HPLC to give 28 mg of the title compound as a white solid. HPLC Ret. time: 2.12 min. MH+ (m/z) 515.1.

EXAMPLE 117

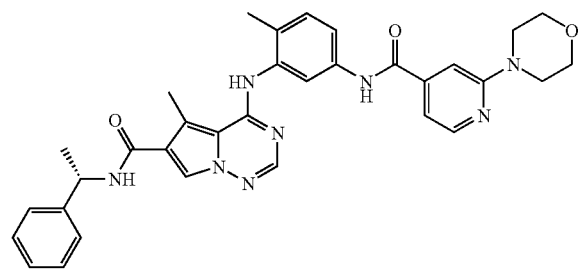

The title compound was prepared from 116E as described in step F for the preparation of Example 116. HPLC Ret. Time: 2.82 min. MH+ (m/z) 591.2.

EXAMPLE 118

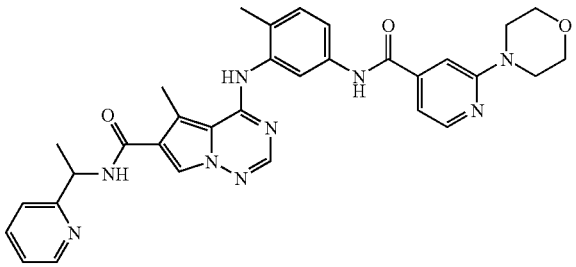

The title compound was prepared from 116E as described in step F for the preparation of Example 116. HPLC Ret. Time: 1.82 min. MH+ (m/z) 592.2.

EXAMPLE 119

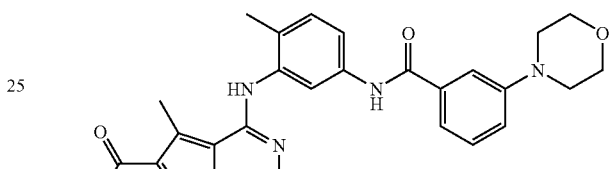

Step A:

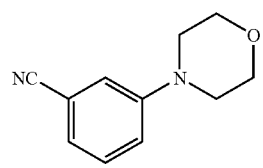

3-Fluorobenzonitrile (10.0 g, 82.6 mmol) and morpholine (40 mL, 0.45 mol) in DMSO (70 mL) was heated at 100° C. for 3 days. The mixture was cooled to rt and poured into 500 mL of cold water. The resulting solid was collected by filtration to give 9.52 g of 119A as a pink solid. HPLC Ret. Time: 2.30 min. MH+ (m/z) 189.2.

Step B:

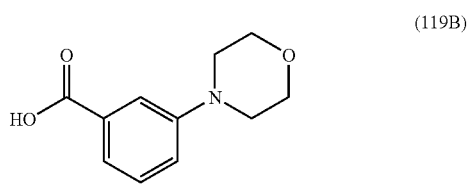

A mixture of 119A (9.50 g) in 6N aqueous sulfuric acid (80 mL) was refluxed for 20 h. After cooling to 0° C., the mixture was brought to a pH of 2 by the slow addition of aqueous sodium hydroxide solution (50% w/w). After stirring for 15 min, the resulting solid was collected by filtration and washed with water then triturated with ethyl acetate (600 ml). The aqueous filtrate was extracted with additional ethyl acetate (450 ml) and the combined organic extracts were dried over anhydrous sodium sulfate, filtered, and concentrated in vacuo to afford 9.50 g of 119B as a light pink solid. HPLC Ret. Time: 1.94 min. MH+ (m/z) 208.1.

Step C:

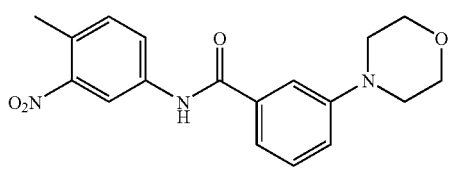
(119C)

To 119B (10.3 g, 50.0 mmol) in anhydrous dichloromethane (300 mL) at rt was slowly added oxalyl chloride (5.2 mL, 60.0 mmol) followed by 1 drop of anhydrous DMF. The reaction was stirred at room temperature for 3 h and the solvent was removed in vacuo to afford an oil which was dissolved in anhydrous dichloromethane (200 mL). To this solution was added 4-methyl-3-nitroaniline (50 mmol) followed by a slow addition of triethylamine (20 mL, 140 mmol) and the mixture was stirred at rt overnight. The reaction was diluted with dichloromethane (400 mL) and washed with water (150 mL×2), saturated aqueous sodium bicarbonate (150 mL×2), then dried over anhydrous magnesium sulfate, filtered, and concentrated in vacuo to afford the crude product which was recrystallized from ethyl acetate to give 9.57 g (56%) of 119C as a yellow solid. HPLC Ret. Time: 3.07 min. MH+ (m/z) 342.1.

Step D:

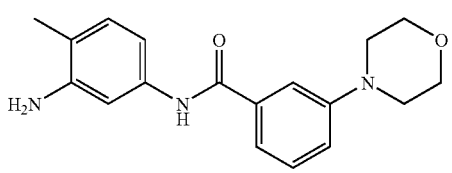
(119D)

Compound 119D was prepared as described for compound 116C.

Step E:

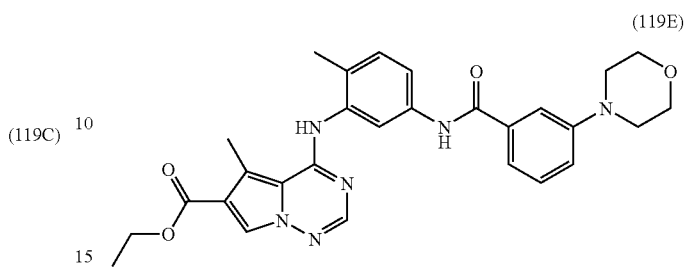
(119E)

119E was prepared from 4-chloro-5-methylpyrrolotriazine-6-ethylcarboxylate as described for 116D by substituting compound 119D for compound 116C. HPLC Ret. Time: 3.39 min. MH+ (m/z) 515.1.

Step F:

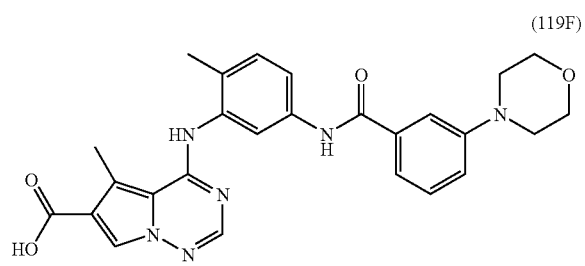
(119F)

119F was prepared from 119E as described for 116E. HPLC Ret. Time: 2.78 min. MH+ (m/z) 487.2.

Step G: Title Compound

The title compound was prepared from 119F as described in Step F for the preparation of Example 116. HPLC Ret. Time: 2.68 min. MH+ (m/z) 514.1.

EXAMPLES 120-123

Examples 120-123 were prepared as described for Example 119.

| Ex. # | Structure | HPLC retention time (min) | (M + H)+ |
|---|---|---|---|
| 120 | 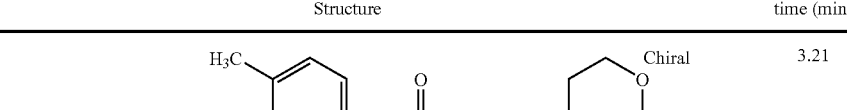 Chiral | 3.21 | 589.7 |

-continued

| Ex. # | Structure | HPLC retention time (min) | (M + H)+ |
|---|---|---|---|
| 121 | 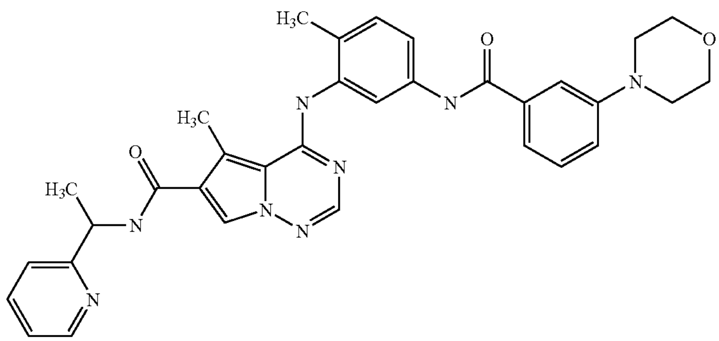 | 2.32 | 591.4 |
| 122 | 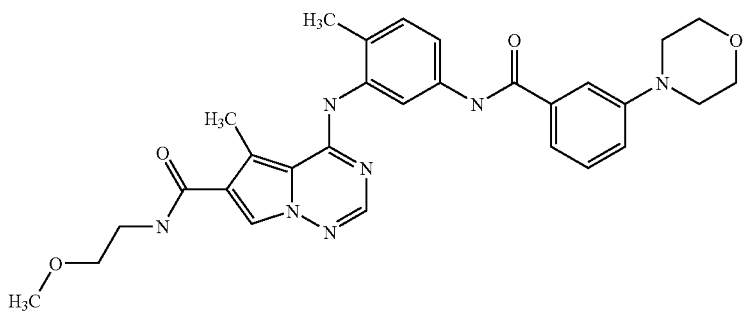 | 2.59 | 544.3 |
| 123 | 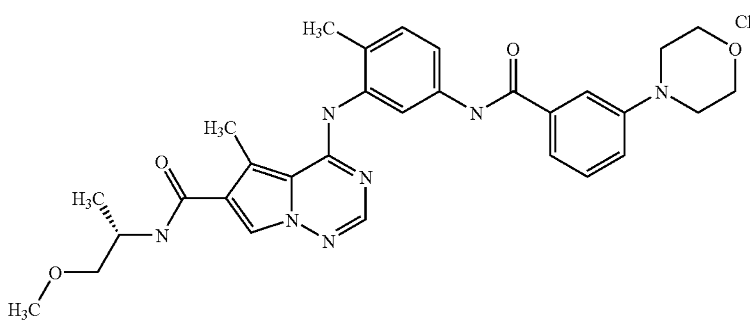 | 2.71 | 558.1 |

EXAMPLE 124

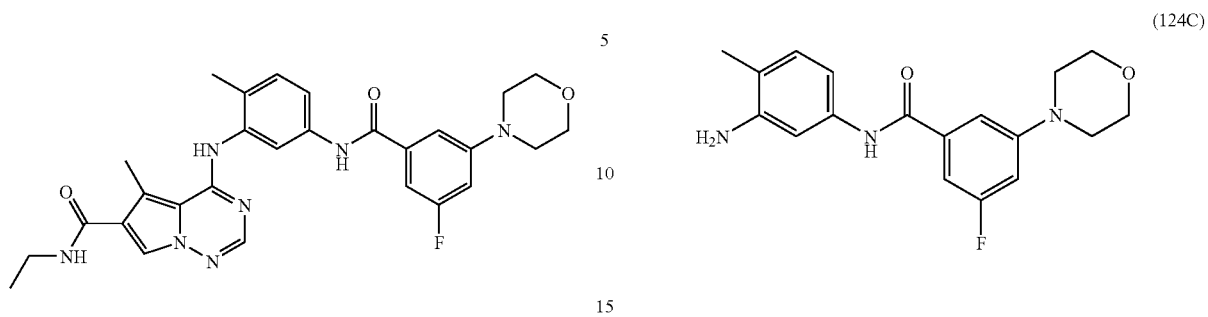

Step A:

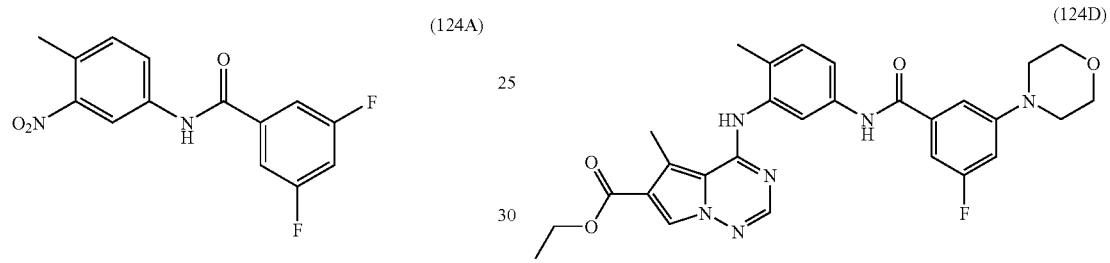
(124A)

Compound 124A was prepared from 4-methyl-3-nitroaniline utilizing the same procedure used for compound 116A by substituting 3,5-difluorobenzoyl chloride for 2-chloropyridine-4- carbonyl chloride.

Step B:

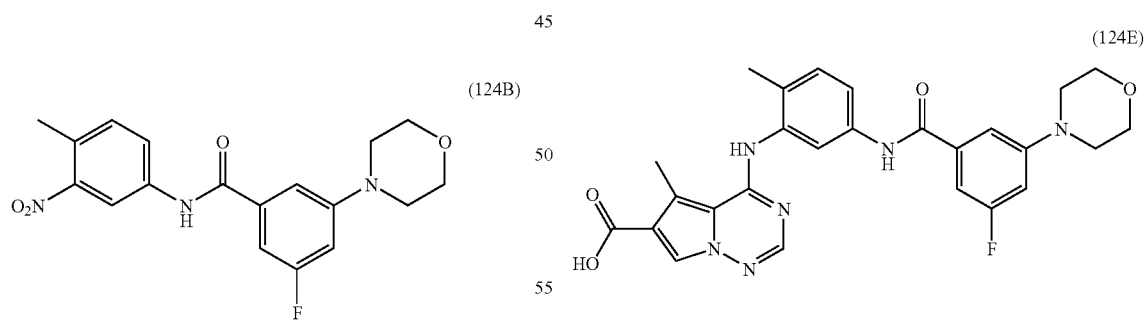
(124B)

Compound 124A (12.2 g) in 80 mL of morpholine was refluxed under argon for 3 days. The resulting mixture was cooled to rt and poured into ice-water (1000 mL) with stirring. The mixture was stirred at rt for 15 min and the resulting solid was collected by filtration and dried in vacuo to afford 14.6 g of 124B as a light yellow solid. HPLC Ret. Time: 3.35 min. MH$^+$ (m/z) 360.1.

Step C:

(124C)

Compound 124C was prepared from by hydrogenation using Pd/C catalyst and hydrogen.

Step D:

(124D)

124D was prepared from 4-chloro-5-methylpyrrolotriazine-6-ethylcarboxylate as described for 116D by substituting compound 124C for compound 116C. HPLC Ret. Time: 3.59 min.

MH$^+$ (m/z) 533.3.

Step E:

(124E)

124E was prepared from 124D as described for 116E. HPLC Ret. Time: 3.06 min.

MH$^+$ (m/z) 505.0.

Step F: Title Compound

The title compound was prepared from 124E as described in Step F for the preparation of Example 116. HPLC Ret. Time: 2.93 min. MH$^+$ (m/z) 532.1.

EXAMPLES 125-147

Examples 125-147 were prepared as described for Example 124.

| Ex. # | Structure | HPLC retention time (min) | (M + H)+ |
|---|---|---|---|
| 125 | 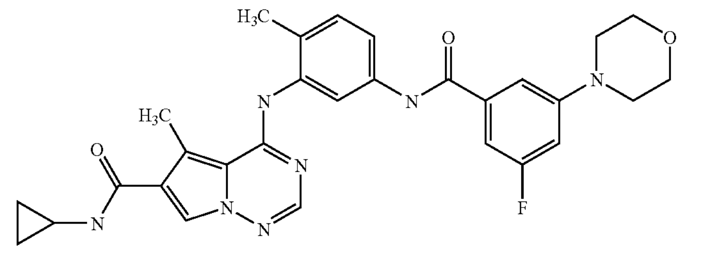 | 2.94 | 544.3 |
| 126 | 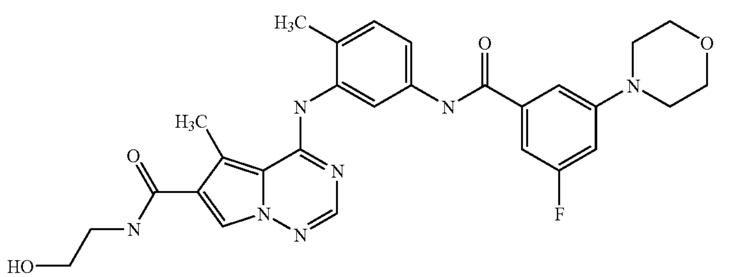 | 2.64 | 548.3 |
| 127 | 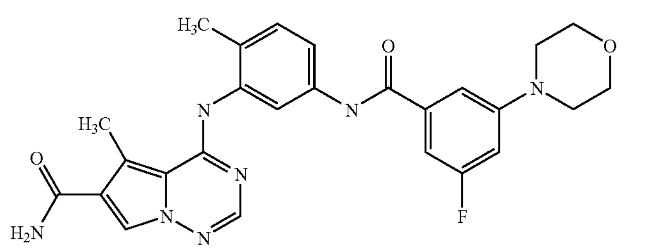 | 2.68 | 504.2 |
| 128 | 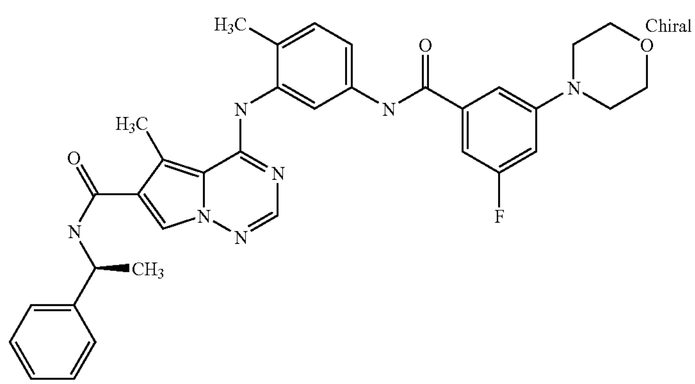 | 3.43 | 608.4 |

-continued

| Ex. # | Structure | HPLC retention time (min) | (M + H)+ |
|---|---|---|---|
| 129 | 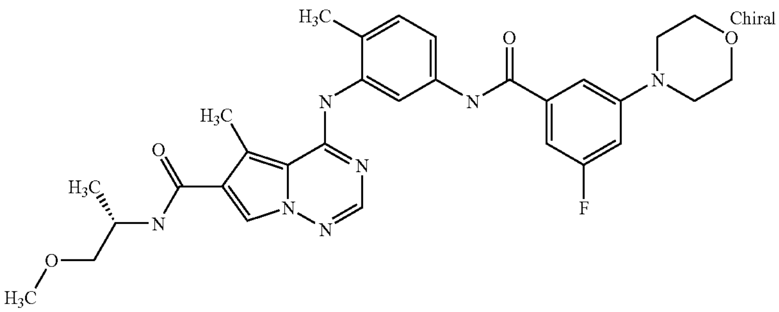 | 2.99 | 576.2 |
| 130 | 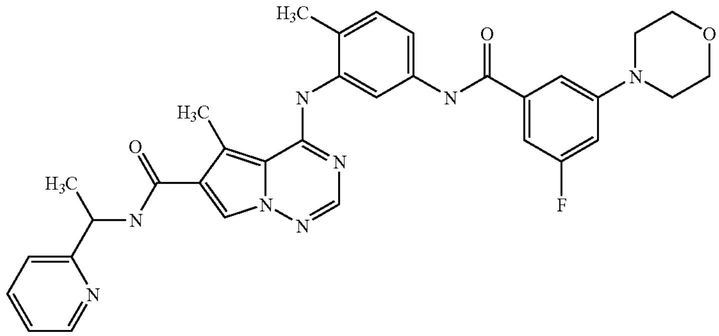 | 2.57 | 609.4 |
| 131 | 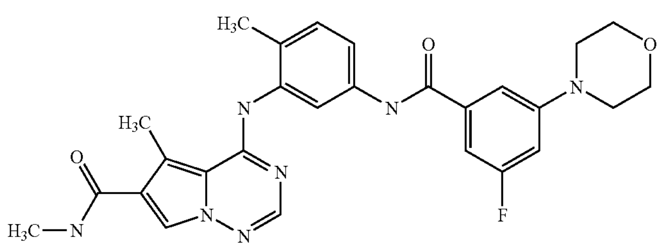 | 2.77 | 518.3 |
| 132 | 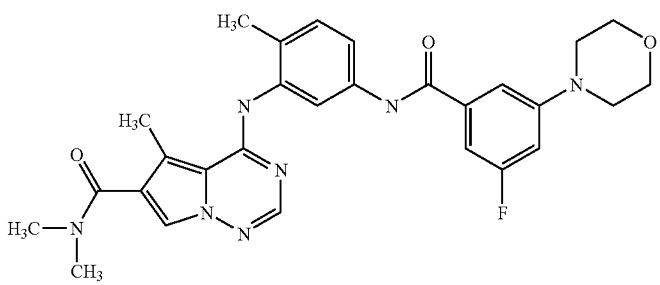 | 2.78 | 532.4 |
| 133 | 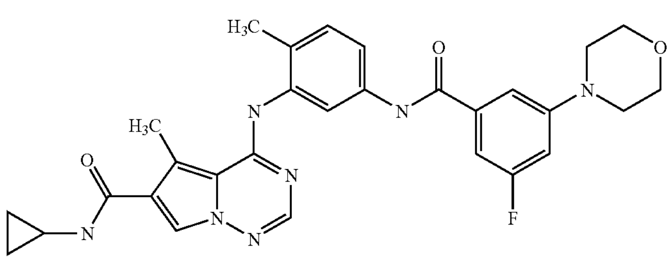 | 2.96 | 544.3 |

-continued

| Ex. # | Structure | HPLC retention time (min) | (M + H)+ |
|---|---|---|---|
| 134 | 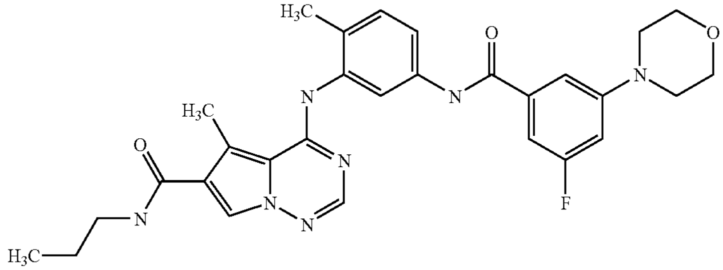 | 3.10 | 546.3 |
| 135 | 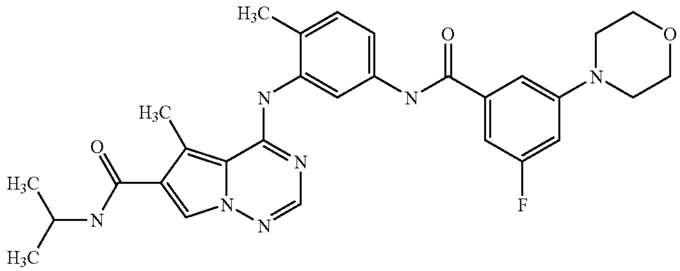 | 3.06 | 546.3 |
| 136 | 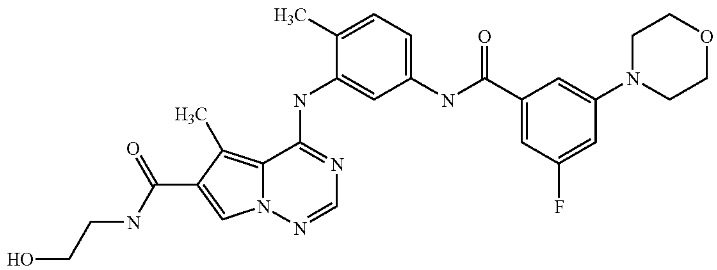 | 2.64 | 548.3 |
| 137 | 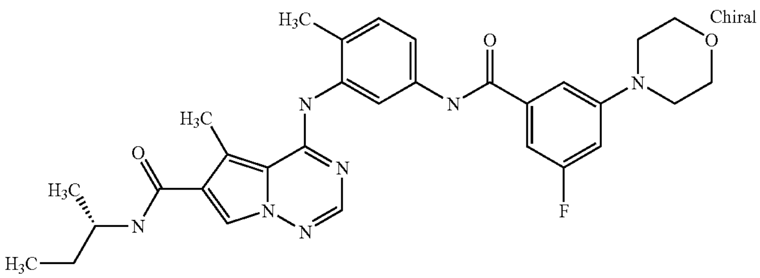 | 3.22 | 560.3 |
| 138 | 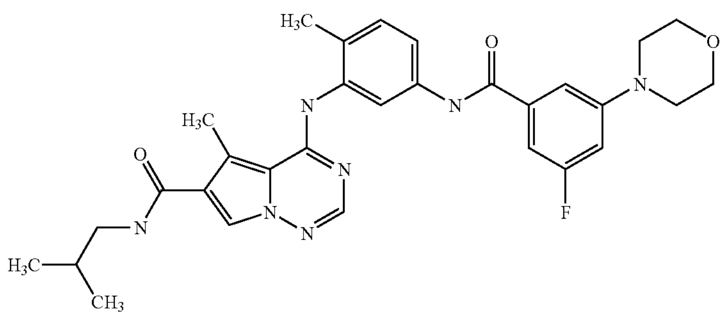 | 3.28 | 560.4 |

-continued

| Ex. # | Structure | HPLC retention time (min) | (M + H)+ |
|---|---|---|---|
| 139 | 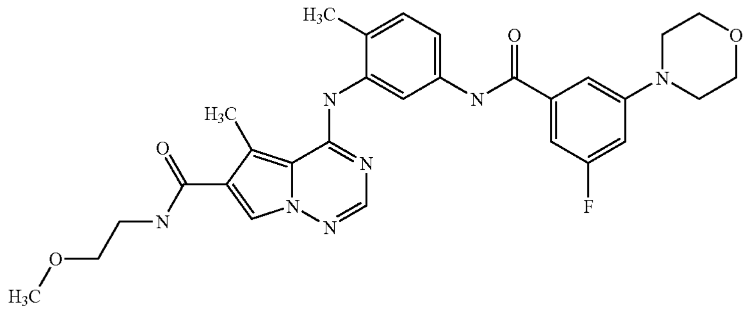 | 2.87 | 562.4 |
| 140 | 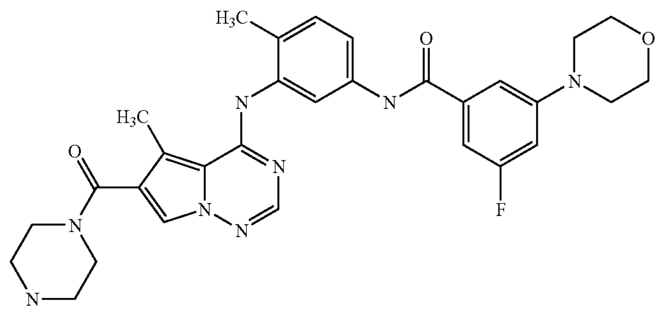 | 2.86 | 562.0 |
| 141 | 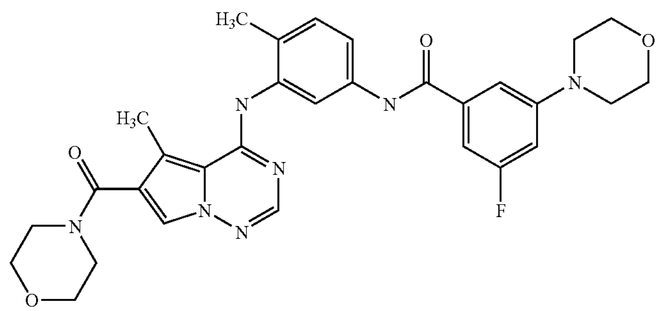 | 2.78 | 574.4 |
| 142 | 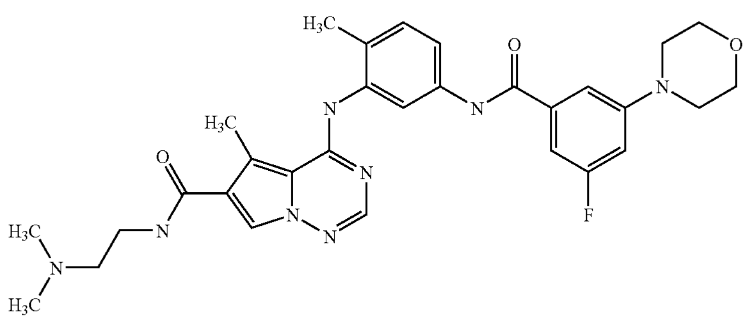 | 2.34 | 575.4 |
| 143 | 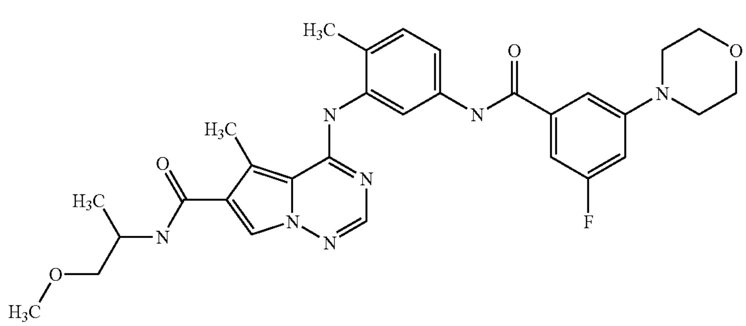 | 2.97 | 576.3 |

-continued

| Ex. # | Structure | HPLC retention time (min) | (M + H)+ |
|---|---|---|---|
| 144 | 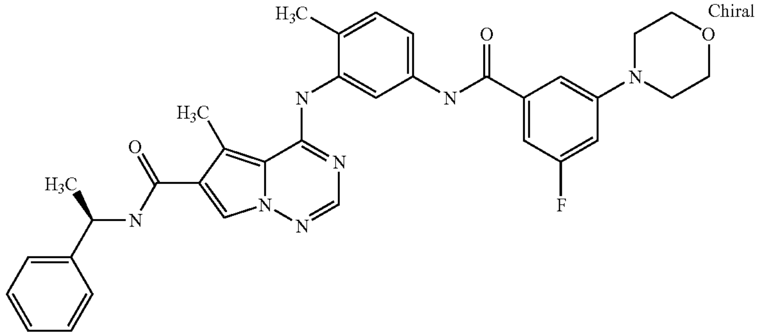 | 3.40 | 608.4 |
| 145 | 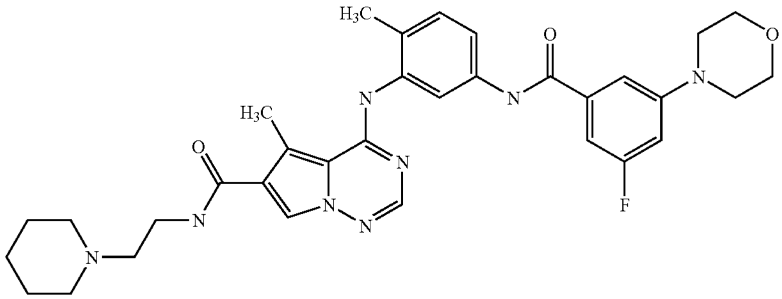 | 2.47 | 615.4 |
| 146 | 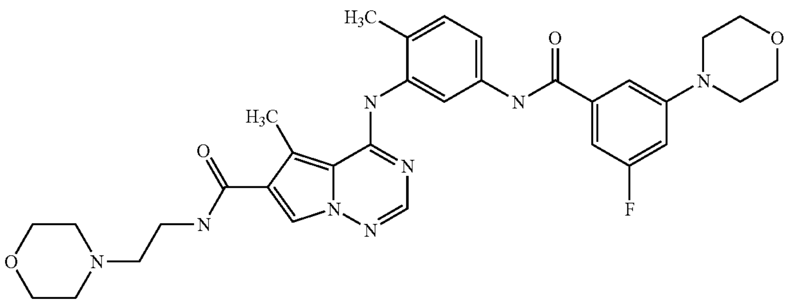 | 2.36 | 617.3 |
| 147 | 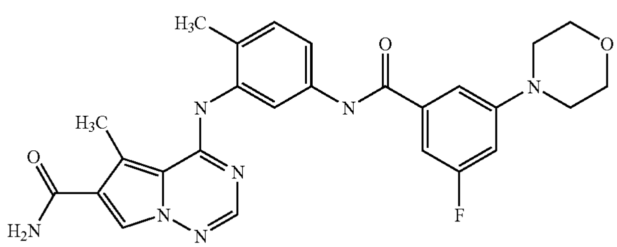 | 2.68 | 504.2 |

EXAMPLE 148

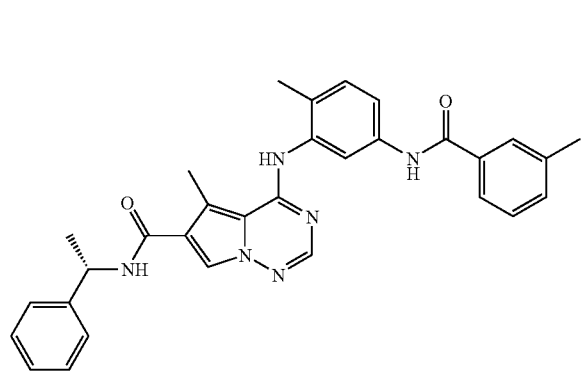

Step A:

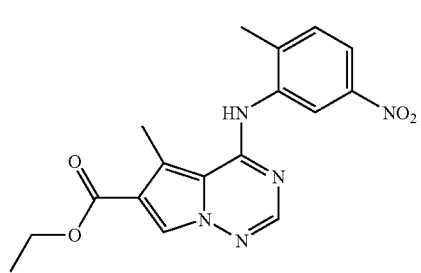
(148A)

148A was prepared from 4-chloro-5-methylpyrrolotriazine-6-ethylcarboxylate as described for 116D by substituting 2-methyl-5-nitroaniline for compound 116C. HPLC Ret. Time: 3.55 min.

MH$^+$ (m/z) 356.3.

Step B:

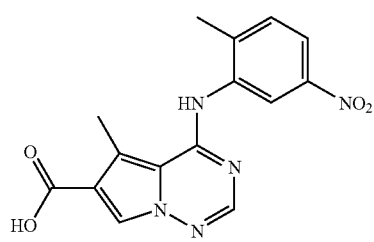
(148B)

148B was prepared from 148A as described for 116E. HPLC Ret. Time: 2.89 min. MH$^+$ (m/z) 328.1.

Step C:

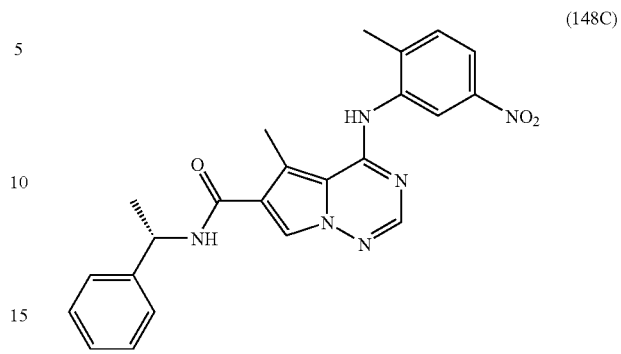
(148C)

Compound 148C was prepared from 148B as described in Step F for the preparation of Example 116 by substituting ethylamine hydrochloride with (S)-(α)-(−)-methylbenzylamine. HPLC Ret. Time: 3.32 min. MH$^+$ (m/z) 431.2.

Step D:

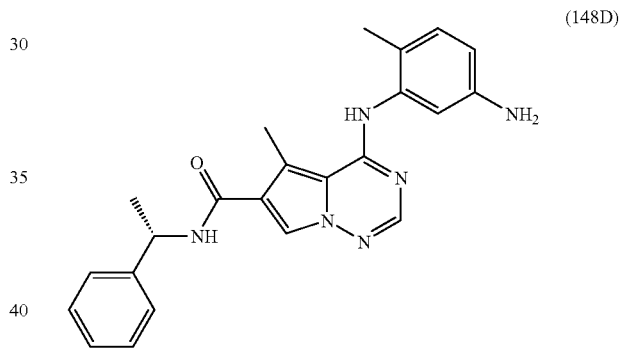
(148D)

Compound 148D was prepared by hydrogenation using Pd/C catalyst and hydrogen.
HPLC Ret. Time: 2.37 min. MH$^+$ (m/z) 401.3.

Step E: Title Compound

To a rt solution of 148D (30 mg, 0.075 mmol) in anhydrous DMF (0.3 mL) were successively added triethylamine (0.14 mmol) and 2-methyl benzoyl chloride (0.11 mmol) and the resulting mixture was stirred overnight. The crude reaction mixture was subjected to purification by reverse-phase preparative HPLC to afford the title compound. HPLC Ret. Time: 3.37 min. MH$^+$ (m/z) 519.2.

EXAMPLES 149-206

The following compounds were prepared as described for the preparation of Example 148 by substituting (S)-(α)-(−)-methylbenzylamine in Step C with the appropriate amine and by substituting 2-methyl benzoyl chloride in Step E with the appropriate acid chloride.

| Ex. # | Structure | | HPLC retention time (min) | (M + H)+ |
|---|---|---|---|---|
| 149 | 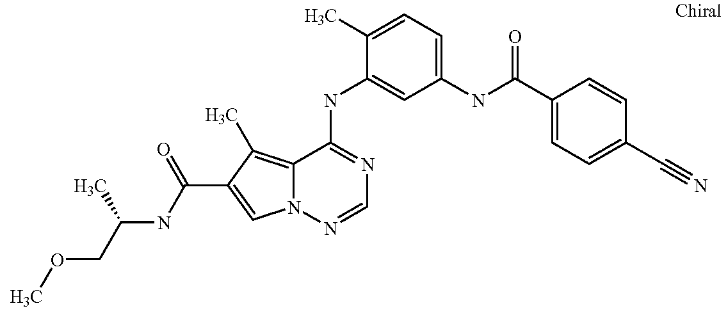 | Chiral | 2.67 | 498.4 |
| 150 | 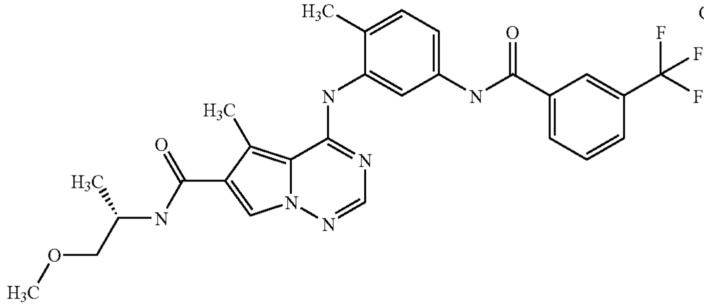 | Chiral | 3.20 | 541.4 |
| 151 | 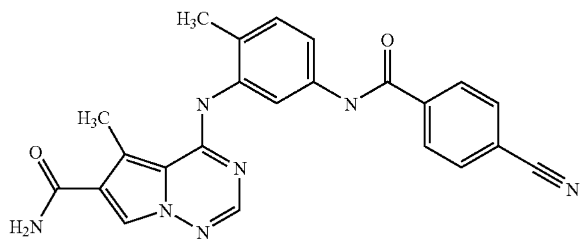 | | 2.33 | 426.3 |
| 152 | 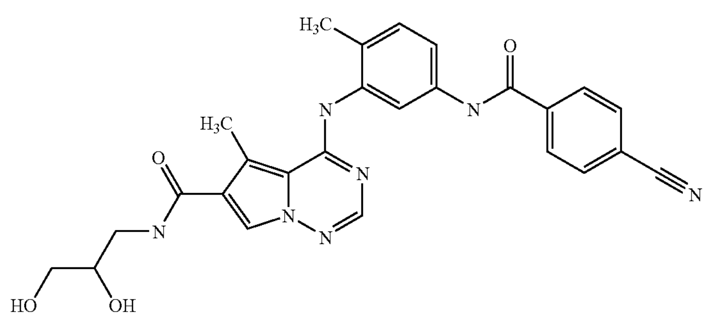 | | 2.26 | 500.4 |
| 153 | 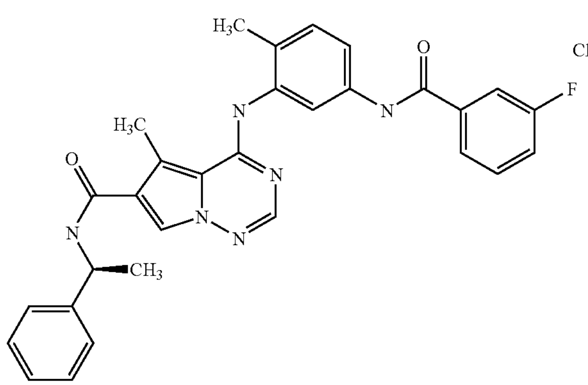 | Chiral | 3.37 | 523.3 |

-continued

| Ex. # | Structure | HPLC retention time (min) | (M + H)+ |
|---|---|---|---|
| 154 | Chiral | 3.20 | 530.2 |
| 155 | Chiral | 3.29 | 535.3 |
| 156 | Chiral | 3.51 | 539.2 |
| 157 | Chiral | 3.57 | 573.2 3.57 |

| Ex. # | Structure | HPLC retention time (min) | (M + H)+ |
|---|---|---|---|
| 158 | Chiral | 3.63 | 589.2 |
| 159 | Chiral | 3.36 | 519.3 |
| 160 | Chiral | 3.24 | 530.1 |
| 161 | Chiral | 3.20 | 535.2 |

-continued
| Ex. # | Structure | HPLC retention time (min) | (M + H)+ |
|---|---|---|---|
| 162 | 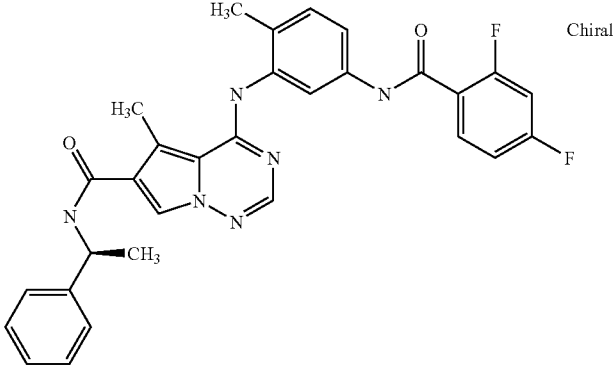 | 3.28 | 541.2 |
| 163 | 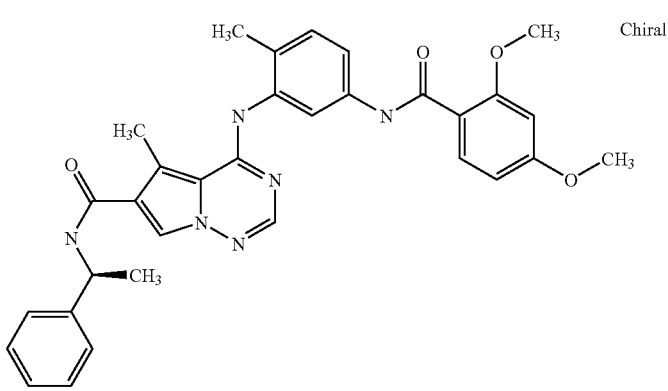 | 3.41 | 565.3 |
| 164 | 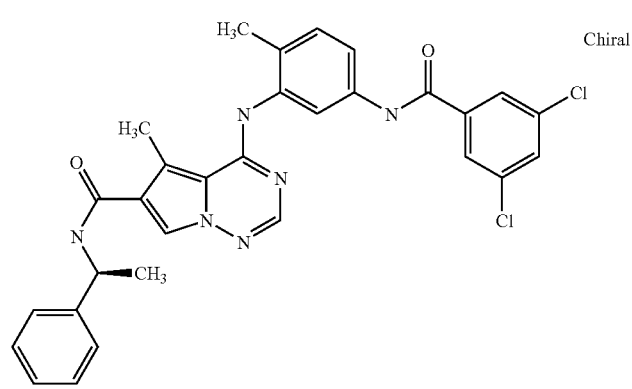 | 3.84 | 573.2 |
| 165 | 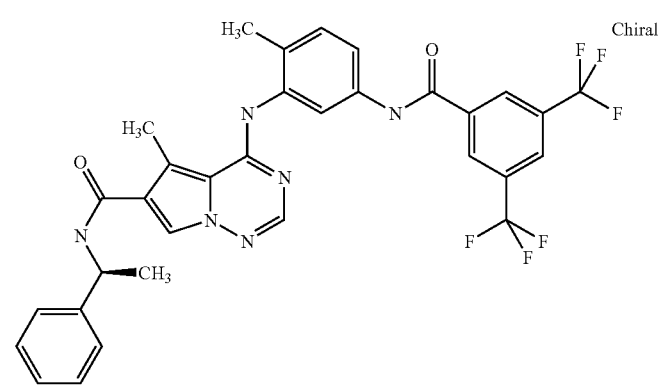 | 3.93 | 641.2 |

-continued

| Ex. # | Structure | HPLC retention time (min) | (M + H)+ |
|---|---|---|---|
| 166 | 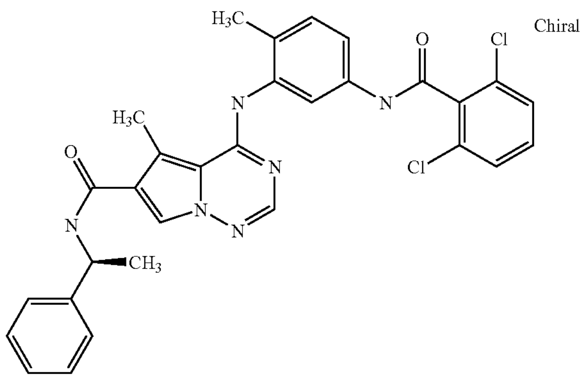 | 3.27 | 573.2 |
| 167 | 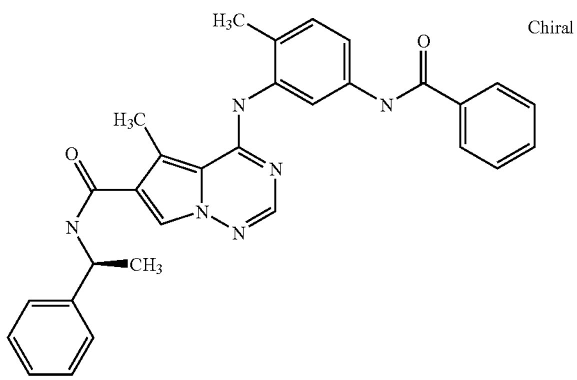 | 3.18 | 505.2 |
| 168 | 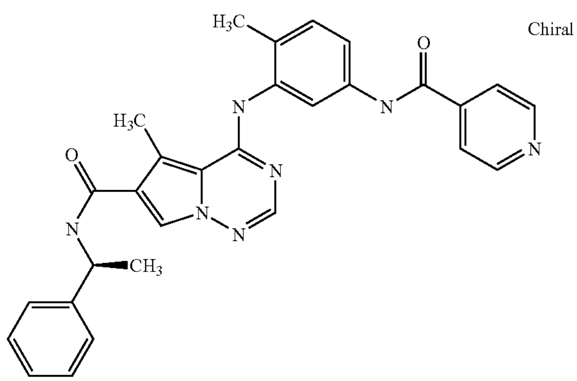 | 2.77 | 506.3 |
| 169 | 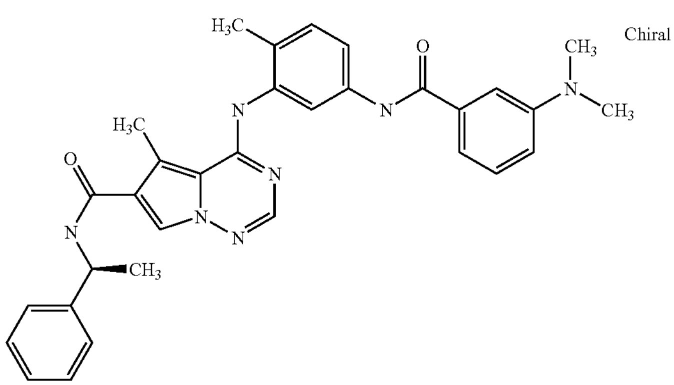 | 3.26 | 548.3 |

-continued

| Ex. # | Structure | | HPLC retention time (min) | (M + H)+ |
|---|---|---|---|---|
| 170 | 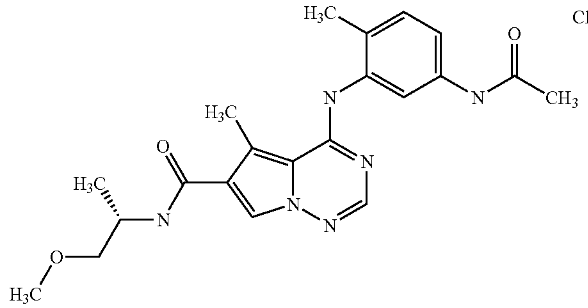 | Chiral | 2.05 | 411.2 |
| 171 | 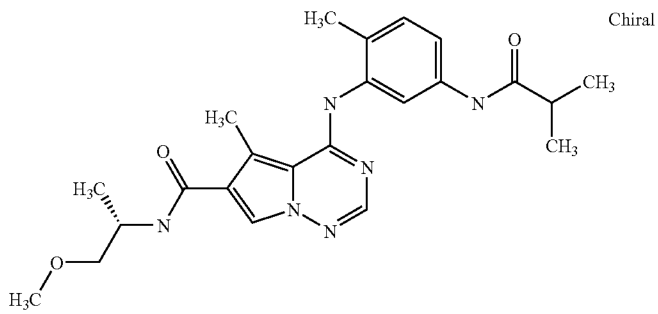 | Chiral | 2.39 | 439.5 |
| 172 | 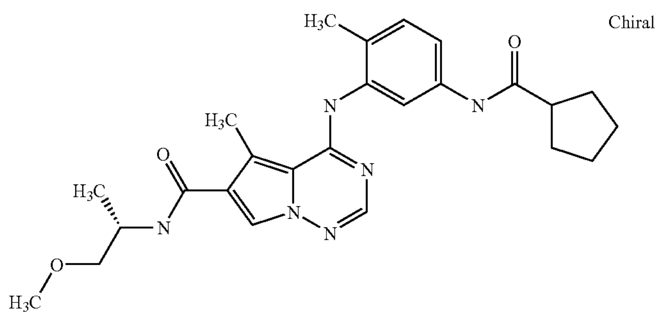 | Chiral | 2.68 | 465.4 |
| 173 | 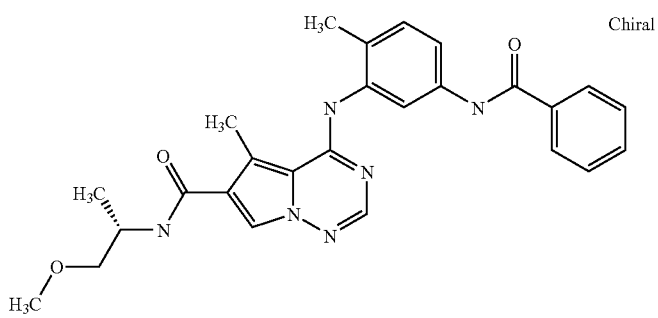 | Chiral | 2.65 | 473.2 |
| 174 | 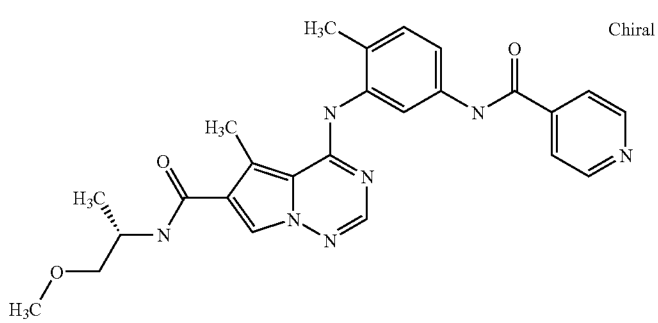 | Chiral | 2.11 | 474.4 |

-continued

| Ex. # | Structure | HPLC retention time (min) | (M + H)+ |
|---|---|---|---|
| 175 | 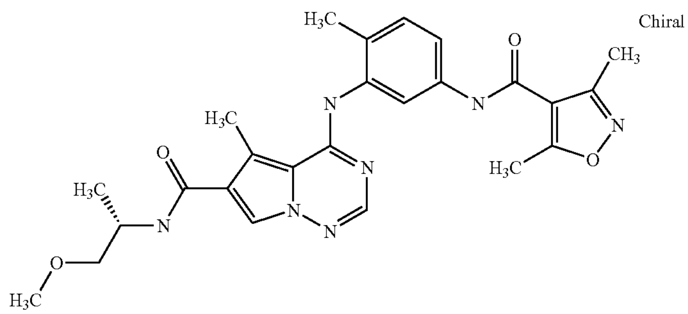 | 2.51 | 492.4 |
| 176 | 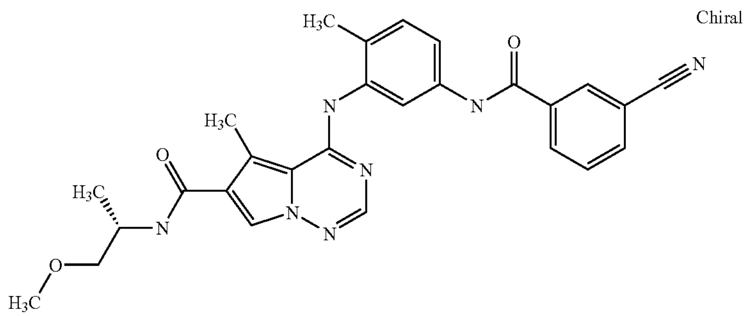 | 2.70 | 498.4 |
| 177 | 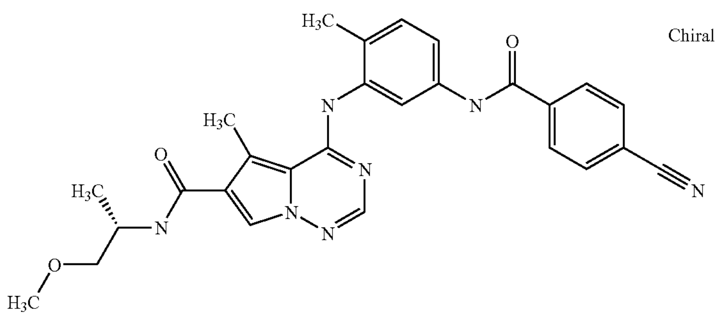 | 2.70 | 498.4 |
| 178 | 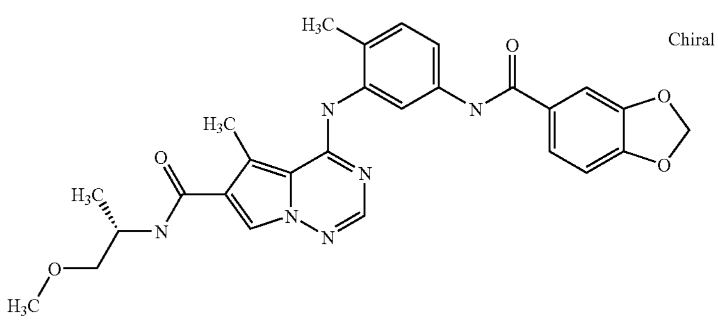 | 2.71 | 517.3 |

| Ex. # | Structure | | HPLC retention time (min) | (M + H)+ |
|---|---|---|---|---|
| 179 | 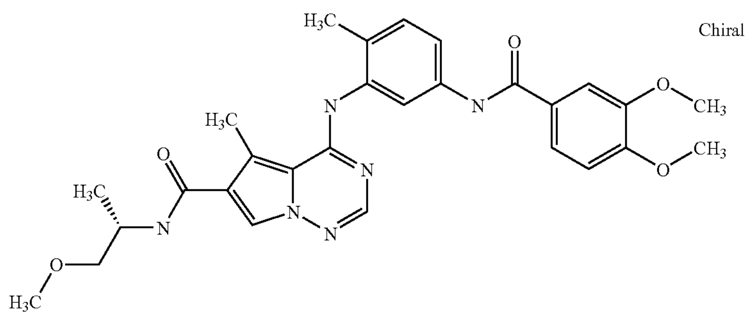 | Chiral | 2.67 | 533.4 |
| 180 | 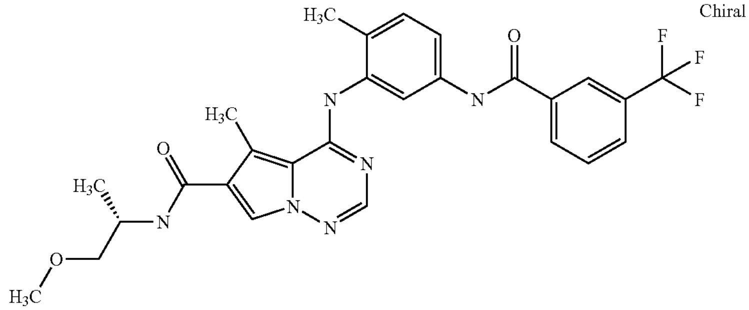 | Chiral | 3.20 | 541.4 |
| 181 | 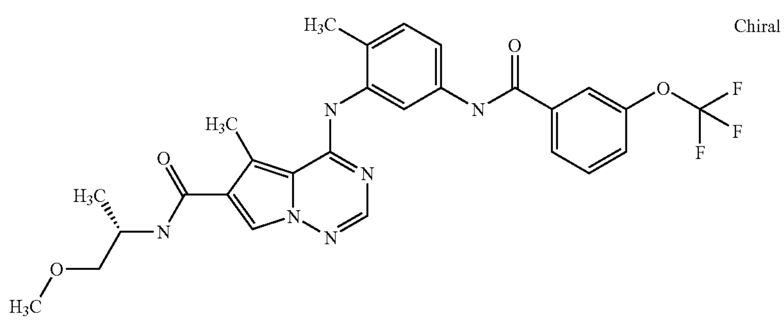 | Chiral | 3.28 | 557.4 |
| 182 | 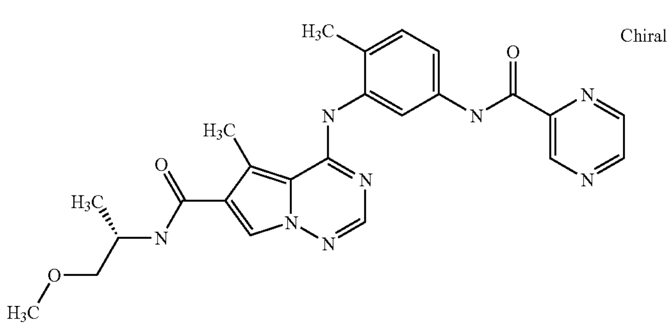 | Chiral | 2.50 | 475.2 |

-continued

| Ex. # | Structure | HPLC retention time (min) | (M + H)+ |
|---|---|---|---|
| 183 | Chiral | 2.06 | 513.4 |
| 184 | Chiral | 2.73 | 515.2 |
| 185 | 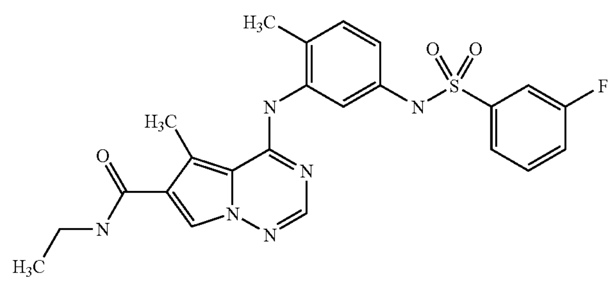 | 2.83 | 483.0 |
| 186 | Chiral | 3.23 | 559.0 |
| 187 | Chiral | 2.89 | 527.0 |

-continued

| Ex. # | Structure | HPLC retention time (min) | (M + H)+ |
|---|---|---|---|
| 188 | 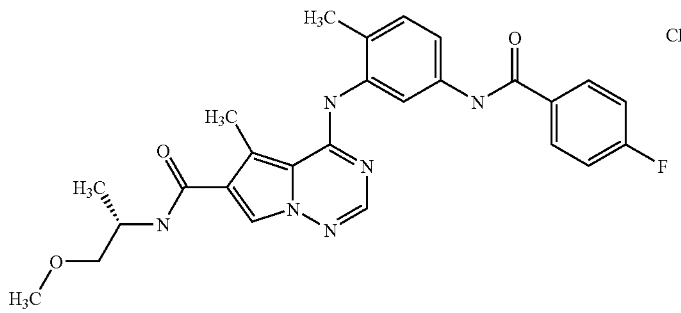 | 2.77 | 491.4 |
| 189 | 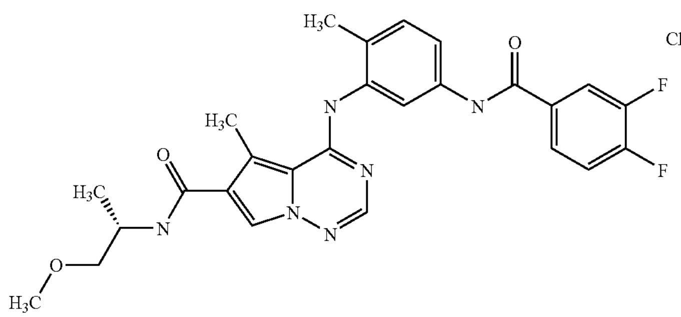 | 2.95 | 509.2 |
| 190 | 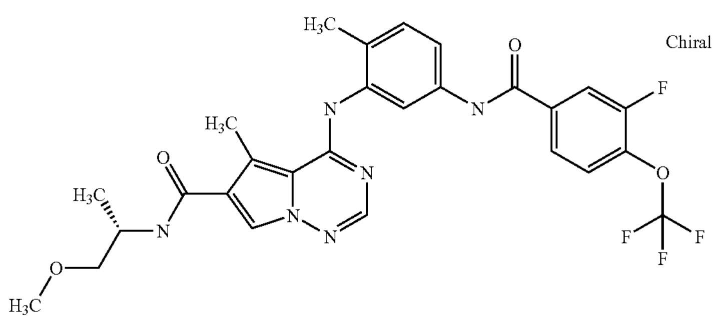 | 3.31 | 559.3 |
| 191 | 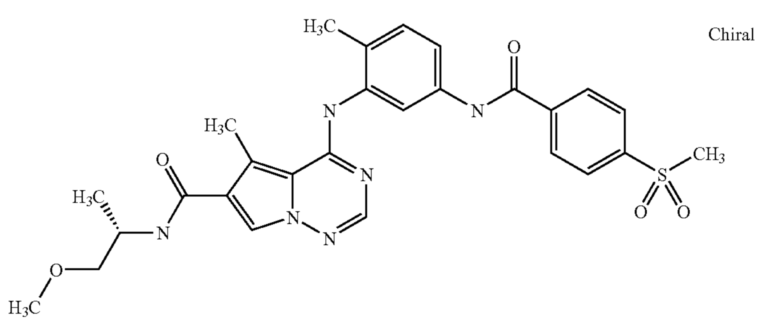 | 2.43 | 551.3 |

-continued

| Ex. # | Structure | HPLC retention time (min) | (M + H)+ |
|---|---|---|---|
| 192 | Chiral | 2.95 | 576.3 |
| 193 | 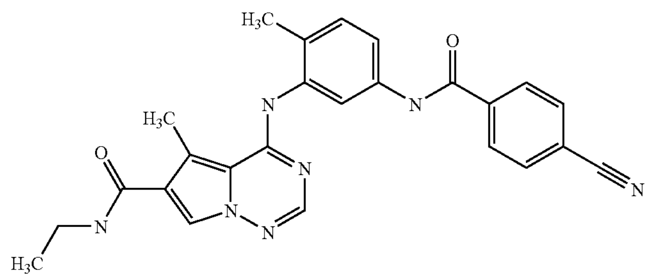 | 2.57 | 454.2 |
| 194 | 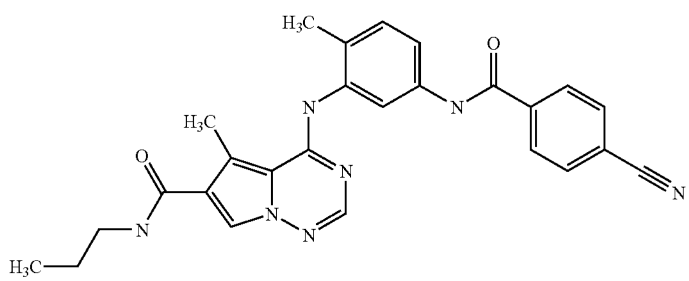 | 2.78 | 468.3 |
| 195 | 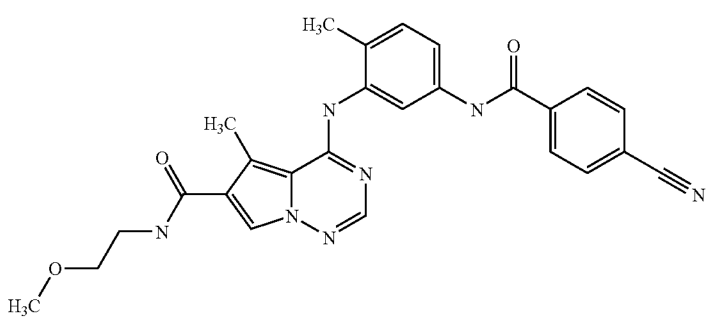 | 2.52 | 484.4 |
| 196 | 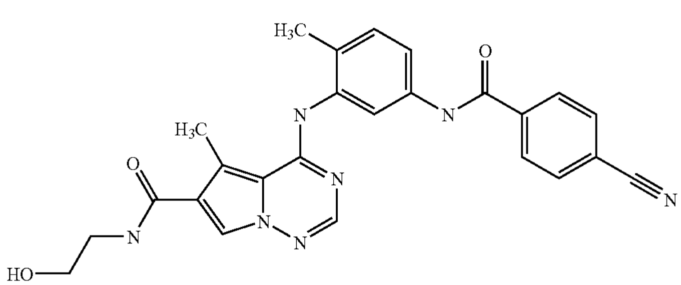 | 2.31 | 470.1 |

| Ex. # | Structure | HPLC retention time (min) | (M + H)+ |
|---|---|---|---|
| 197 | 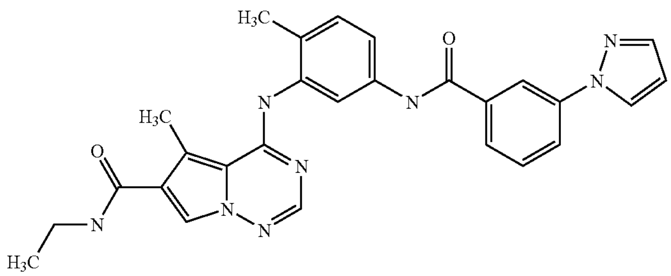 | 2.74 | 495.2 |
| 198 | 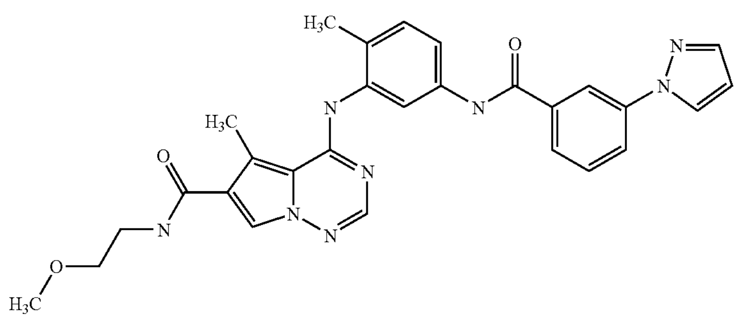 | 2.72 | 524.2 |
| 199 | 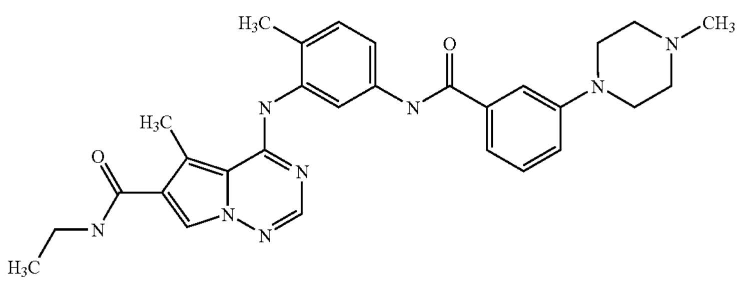 | 2.00 | 527.4 |
| 200 | 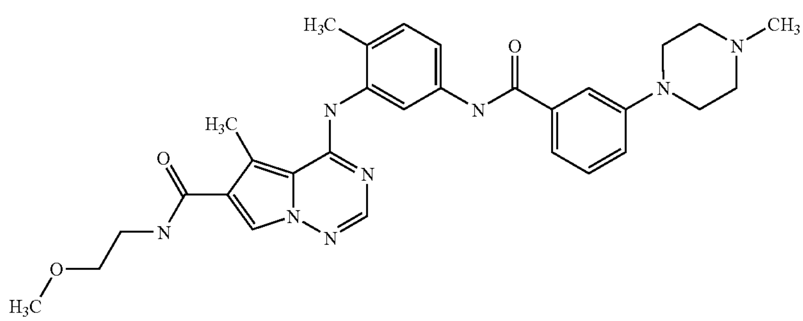 | 2.01 | 557.4 |
| 201 | 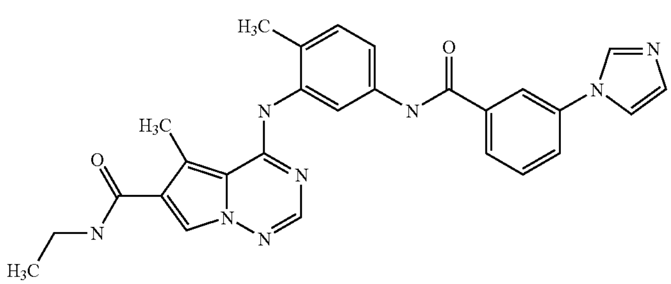 | 1.98 | 495.4 |

-continued

| Ex. # | Structure | HPLC retention time (min) | (M + H)+ |
|---|---|---|---|
| 202 | 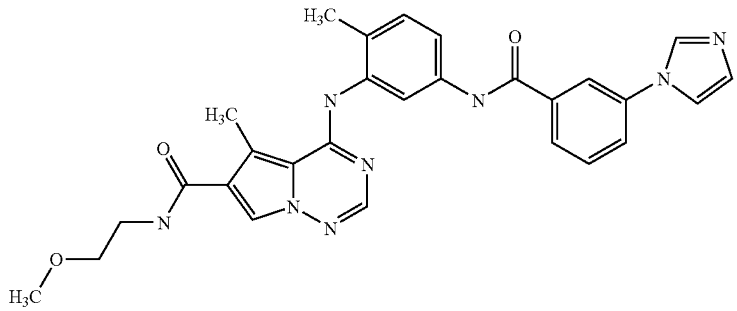 | 1.95 | 525.3 |
| 203 | 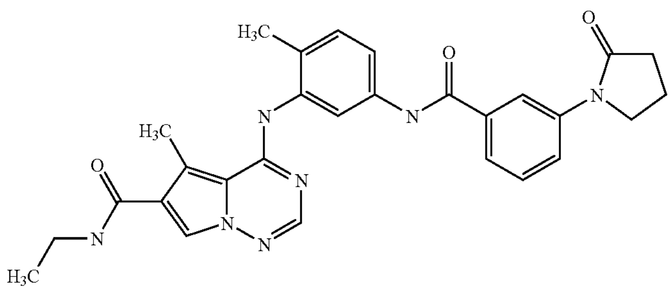 | 2.54 | 512.3 |
| 204 | 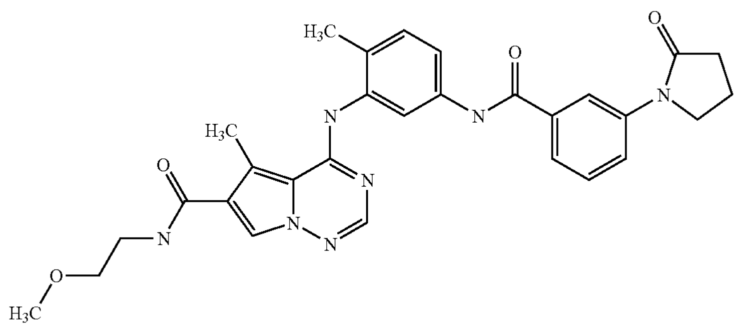 | 2.51 | 542.4 |
| 205 | 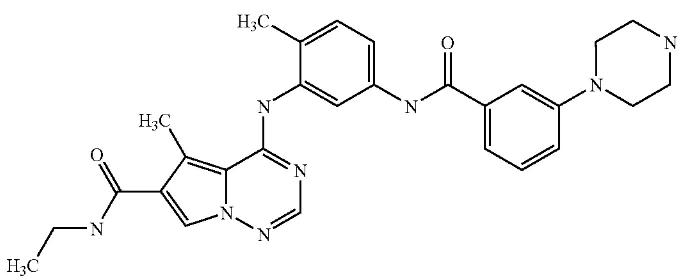 | 2.04 | 513.3 |
| 206 | 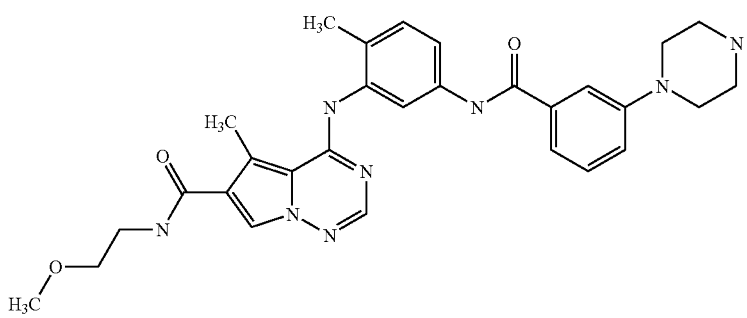 | 2.03 | 543.3 |

EXAMPLE 207

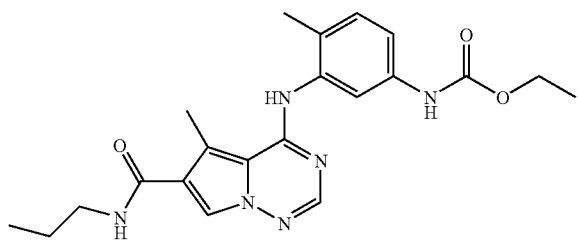

Step A

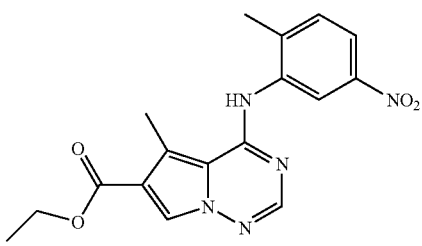

A suspension of chloropyrrolotriazine (2.03 g, 8.47 mmol) and 3-nitro-5-methyl aniline (1.41 g, 9.3 mmol) in DMF (25 mL) was stirred at rt for 24 h. Water (125 mL) was added over 30 min and the solution stirred for 1 h upon which the pH was adjusted to neutral with sat. aq. NaHCO$_3$. The solids were filtered, washed with water, and dried to give compound A (2.589 g, 85% yield) as a pale tan solid.

Step B:

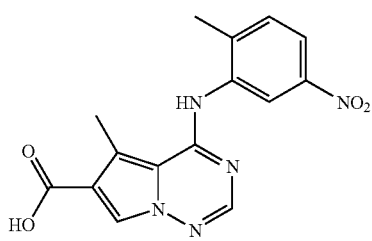

To a solution of Compound A (825 mg, 2.32 mmol) in THF (2 mL) and MeOH (1 mL) was added 1N NaOH (6 mL) and the reaction heated at 60° C. for 24 h. The reaction mixture was cooled, concentrated to remove the organic solvents, and the pH was adjusted to neutral with 1 N HCl. The solids were filtered, washed with water, and dried to give compound B. LCMS (M+H$^+$)=328.1. HPLC (Condition A): 3.40 min.

Step C:

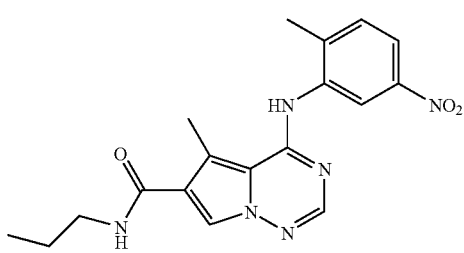

A solution of compound B (2.32 mmol), EDCI (489 mg, 2.55 mmol), and HOBt (345 mg, 2.55 mmol) in DMF (6 mL) was stirred at rt for 1 h, and then n-propyl amine (0.38 mL, 6.4 mmol) was added. The reaction was stirred for 4 h and water was added to precipitate the product. The solids were filtered and purified via column chromatography on silica (33% ethyl acetate\hexanes) to give compound C (0.79 g, 93% yield) as a white solid. $^1$H NMR (CDCl$_3$): δ 9.11 (s, 1H), 7.92 (m, 2H), 7.71 (s, 1H), 7.36 (d, J=8.4 Hz, 1H), 5.82 (br m, 1H), 3.34 (q, J=6.7 Hz, 2H), 2.86 (s, 3H), 2.41 (s, 3H), 1.58 (m, 2H), 1.16 (t, J=7.5 Hz, 3H). LCMS (M+H$^+$)=369.3.

HPLC (Condition A): 3.42 min.

Step D:

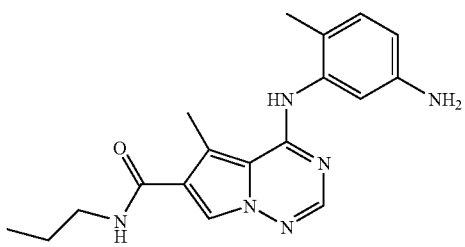

A solution of compound C (794 mg, 2.16 mmol) and 10% Pd/C (250 mg, wet) in MeOH (20 mL) was degassed and backfilled with hydrogen three times and stirred for 2 h. The solution was filtered and concentrated to give compound D (691 mg, 95% yield). $^1$H NMR (CDCl$_3$): δ 7.94 (s, 1H), 7.73 (s, 1H), 7.53 (s, 1H), 7.23 (m, 1H), 7.06 (d, J=8.1 Hz, 1H), 6.53 (dd, J=8.1, 2.2 Hz, 1H) 5.86 (br m, 1H), 3.43 (q, J=6.6 Hz, 2H), 2.91 (s, 3H), 2.27 (s, 3H), 1.68 (m, 2H), 1.02 (t, J=7.3 Hz, 3H).

LCMS (M+H$^+$)=339.2. HPLC (Condition A): 2.39 min.

Step E: Title Compound

To a suspension of 2.5 g (7.4 mmol) of compound D in 50 mL of CH$_2$Cl$_2$ was added 1.42 μL of DIPEA at rt. The reaction mixture was cooled to 0° C. and added ethylchloroformate (0.77 mL). The reaction was stirred for 2 h at room temperature and then quenched with MeoH. The solvents were removed and the product precipitated with water (40 mL). The product was collected by vacuum filtration and washed with water (2×) then dissolved in hot MeOH, decolorized with charcoal and recrystallized from EtOH to give 2.10 g (70%) of the titled compound as a pure product.

EXAMPLES 208-233

Compounds having the formula below, wherein W and B$^a$ have the values listed in the Table provided below, were prepared following the same procedure described for Example 1, using the appropriate acid chloride, chloroformate or isocyanate.

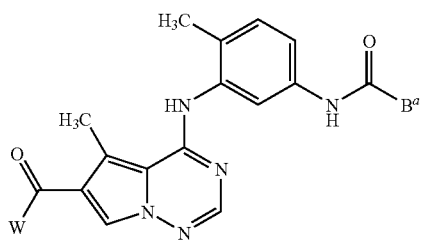

| Ex. No. | W | B$^a$ | HPLC ret. time (min.) | MS (M + H)+ |
|---|---|---|---|---|
| 208 | —NHCH$_2$CH$_3$ | —CH$_3$ | 2.41 | 367.2 |
| 209 | —NHCH$_2$CH$_2$CH$_3$ | —CH$_3$ | 2.74 | 381.4 |
| 210 | —NHCH$_2$CH$_3$ | —CH$_2$CH$_3$ | 2.85 | 381.2 |
| 211 | —NHCH$_2$CH$_2$CH$_3$ | —CH$_2$CH$_3$ | 2.85 | 395.2 |
| 212 | —OCH$_3$ | —OCH$_2$CH$_3$ | 3.51 | 384.2 |
| 213 | —NHCH$_2$CH$_2$CH$_3$ | —OCH$_2$CH$_3$ | 3.16 | 411.2 |
| 214 | ![H$_3$C, O, N-methoxy-2-propylamino group] | —OCH$_2$CH$_3$ | 3.00 | 441.3 |
| 215 | ![sec-butylamino group] | —OCH$_2$CH$_3$ | 3.29 | 425.3 |
| 216 | —NHCH$_2$CH$_3$ | —OCH$_2$CH$_3$ | 2.89 | 397.3 |
| 217 | —NHCH(CH$_3$)$_2$ | —OCH$_2$CH$_3$ | 3.10 | 411.2 |
| 218 | —NHCH$_2$CH$_2$OH | —OCH$_2$CH$_3$ | 2.54 | 413.2 |
| 219 | —NHCH$_2$CH$_2$CH$_3$ | —OCH$_3$ | 2.94 | 397.2 |
| 220 | —NHCH$_2$CH$_2$CH$_3$ | —OCH$_2$CH$_2$CH$_3$ | 3.03 | 425.2 |
| 221 | —NHCH$_2$CH$_2$CH$_3$ | —OCH(CH$_3$)$_2$ | 3.38 | 425.3 |
| 222 | —NHCH$_2$CH$_2$CH$_3$ | —OCH2CH$_2$F | 3.00 | 429.2 |
| 223 | —NHCH$_2$CH$_2$CH$_3$ | ![phenoxy] | 3.38 | 459.2 |
| 224 | —NHCH$_2$CH$_2$CH$_3$ | ![4-methylphenoxy] | 3.72 | 473.3 |
| 225 | —NHCH$_2$CH$_3$ | —CH$_2$OCH$_3$ | 2.39 | 381.2 |
| 226 | —NHCH$_2$CH$_2$CH$_3$ | —CH$_2$OCH$_3$ | 2.83 | 411.2 |
| 227 | —NHCH$_2$CH$_2$CH$_3$ | ![3-tert-butyl-1-methyl-1H-pyrazol-5-yl] | 3.86 | 503.5 |
| 228 | —OCH$_3$ | ![3-tert-butyl-1-methyl-1H-pyrazol-5-yl amino dimethyl] | 2.46 | 491.2 |

-continued

| Ex. No. | W | B$^a$ | HPLC ret. time (min.) | MS (M + H)+ |
|---|---|---|---|---|
| 229 | (S)-methoxyisopropylamino group | 3-tert-butyl-1-methyl-1H-pyrazol-5-ylamino | 3.46 | 584.4 |
| 230 | —NHCH$_2$CH$_3$ | 3-tert-butyl-1-methyl-1H-pyrazol-5-ylamino | 3.38 | 504.3 |
| 231 | —NHCH$_2$CH$_2$CH$_3$ | 3-tert-butyl-1-methyl-1H-pyrazol-5-ylamino | 3.56 | 518.3 |
| 232 | (S)-sec-butylamino | 3-tert-butyl-1-methyl-1H-pyrazol-5-ylamino | 3.67 | 532.3 |
| 233 | —NHCH(CH$_3$)$_2$ | 3-tert-butyl-1-methyl-1H-pyrazol-5-ylamino | 3.53 | 518.4 |

EXAMPLE 234

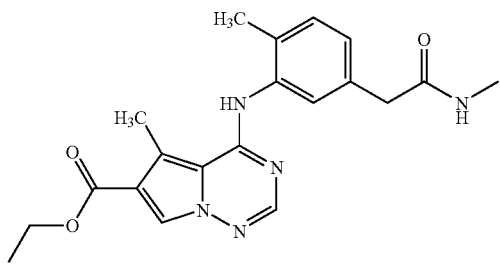

Step A:

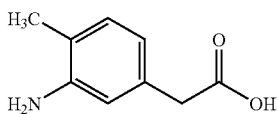

p-Tolyl acetic acid (0.6 g, 4.1 mmol) was added H$_2$SO$_4$ (5.5 mL) with cooling in an ice bath. NaNO$_3$ (0.35 g, 4.1 mmol) was added slowly and mixture was stirred at 0-5° C. for 8 h. The solution was carefully poured onto ice and the solids filtered and washed with water to give 3-nitro p-tolylacetic acid (0.59 g, 74%).

The crude solid (160 mg) was hydrogenated under H$_2$ balloon in MeOH (15 mL) in the presence of 10% Pd—C at rt for 2 h. Filtration gave 3-amino p-tolylacetic acid as a yellow solid (131 mg, 97%).

Step B:

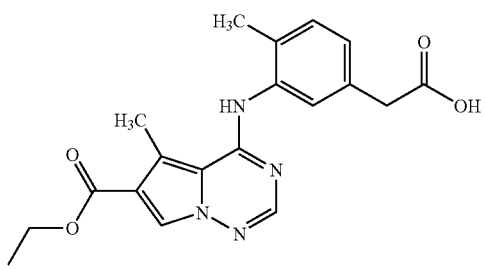

3-Amino p-tolylacetic acid (131 mg, 0.8 mmol) and 1B (220 mg, 0.92 mmol) were stirred for 18 h in DMF (2 mL). Water was added to precipitate the product and the pH was adjusted to 6 with aq NaHCO$_3$. The solids were filtered, washed with water and dried to afford the above ester (62%).

Step C: Title Compound

To the above acid (86 mg, 0.23 mmol) in DMF (2 mL) was added EDC (49 mg, 0.26 mmol) and HOBt (35 mg, 0.26 mmol). The mixture was stirred for 1 h followed by addition of methylamine (0.25 ml, 2M in THF). The reaction was stirred for 18 h then added water (12 mL). The solids were filtered to obtain the title compound (75 mg, 84%). (M+H)+: 395.2, HPLC retention time: 2.85 min.

EXAMPLE 235 AND 236

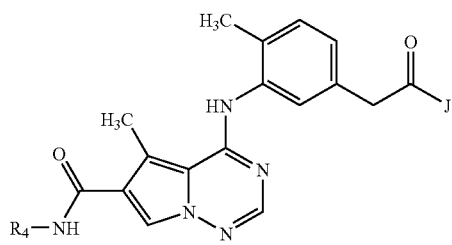

Examples 235 and 236 were prepared from Example 234 following the procedure described in Example 2 and 3.

| Ex. No. | R4 | J | HPLC ret. time (min.) | MS (M + H)+ |
|---|---|---|---|---|
| 235 | —NHCH$_2$CH$_2$CH$_3$ | —NHCH$_3$ | 395.1 | 2.67 |
| 236 | —NHCH$_2$CH$_3$ | —NHCH$_3$ | 381.2 | 2.39 |

EXAMPLE 237

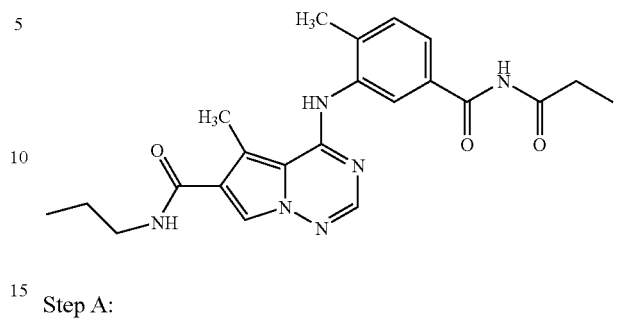

Step A:

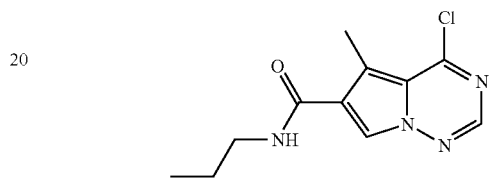

Compound 1B was hydrolyzed under standard saponification methods and coupled with n-propylamine using the EDC/HOBt method to furnish the C-6 n-propylamido oxopyrrolotriazine. A solution of this compound (1.65 g, 7 mmol) in toluene (50 mL) was added POCl$_3$ (0.8 mL, 8.45 mmol) and DIPEA (1 mL, 5.6 mmol) and the solution heated at reflux for 10 h. The reaction was cooled and poured into ice cold aqueous NaHCO$_3$. The solution was extracted with EtOAc (3×), dried over Na$_2$SO$_4$, filtered and concentrated to give the chloride as a yellow solid (1.65 g, 93%) which was used without further purification.

Step B:

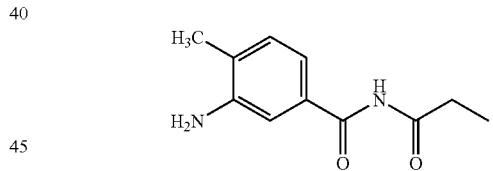

A solution of 3-nitro-4-methyl benzamide (402 mg, 2.2 mmol) in dichloroethane (15 mL) was added propionic anhydride (2.45 mmol) and DMAP (381 mg, 3.1 mmol) and the reaction mixture heated at 55° C. Additional propionic anhydride (2.45 mmol) and DMAP (1.4 eq) was added and the reaction temperature increased to 85° C. for 2 h. The reaction vessel was cooled and poured into CH$_2$Cl$_2$ (50 mL) and water (25 mL). The organic layer was washed with 1N HCl and brine, dried over Na$_2$SO$_4$, filtered and concentrated in vacuo to an oil which was purified via column chromatography (15% then 30% EtOAc/hexane) to give the nitro imide (333 mg, 63%).

The above compound (152 mg, 0.6 mmol) was dissolved in EtOH (6 mL) and added 5% Pd—C (wet, 35 mg) and evacuated and back filled under a hydrogen balloon. The reaction was stirred for 2 h, filtered and concentrated to a white solid which was used without further purification (132 mg, 99%).

The above aniline (20 mg) and chloride (20 mg) were combined in DMF (0.25 mL) and stirred for 18 h. The solution was added water (1 mL) drop wise and neutralized with dilute aq. NaHCO$_3$. The solids were stirred rapidly for 2 h then filtered and washed with water to give 33.6 mg, 98% yield.

EXAMPLE 238

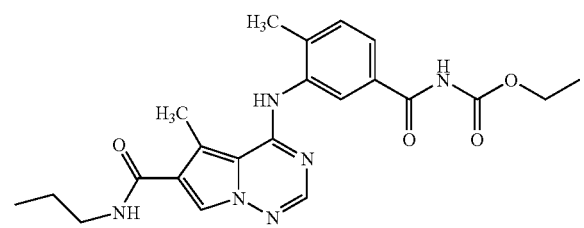

Step A:

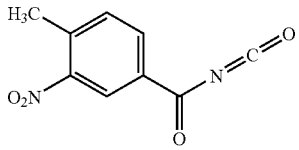

3-nitro-4-methyl benzamide (0.2 g, 1.1 mmol) was suspended in dichloroethane (6 mL) and added oxalyl chloride (0.12 mL, 1.3 mmol) at 0° C. The solution was allowed to warm to room temperature and stir for 1 h followed by heating at reflux for 18 h. The reaction was cooled, concentrated to remove volatiles and dried under vacuum to give the desired product which was used without further purification.

Step B:

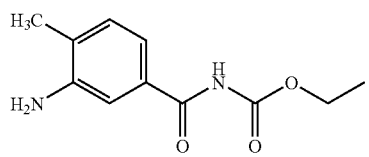

To the crude acyl isocyanate was added CH$_2$Cl$_2$ (5 mL) and dry EtOH (1 mL) and the reaction stirred for 1 h. The solvents were removed in vacuo and the solids filtered with EtOAc and washed with ether to give a white solid (203 mg, 73%). The crude solids were dissolved in MeOH (25 mL) and hydrogenated under hydrogen balloon in the presence of 5% Pd—C for 2 h to give a white solid after filtration (174 mg, 97%).

Step C: Title Compound

This solid from the previous step was coupled with the above pyrrolotriazine chloride under standard conditions to afford the title compound in 55% yield.

EXAMPLES 239-267

Examples 239-267 were prepared as described in Example 238 by reacting the acyl isocyanate with an appropriate amine.

| Ex. No. | W | J | HPLC ret. time (min.) | MS (M + H)+ |
|---|---|---|---|---|
| 239 | —NHCH$_2$CH$_2$CH$_3$ | —OCH$_3$ | 425.5 | 2.98 |
| 240 | —NHCH$_2$CH$_2$CH$_3$ | —OCH$_2$CH$_3$ | 439.3 | 3.12 |
| 241 | —NHCH$_2$CH$_2$CH$_3$ | —OCH(CH$_3$)$_2$ | 435.4 | 3.30 |
| 242 | —NHCH$_2$CH$_2$CH$_3$ | -O-Ph | 487.6 | 3.53 |
| 243 | —NHCH$_2$CH$_3$ | —OCH$_3$ | 411.2 | 2.66 |
| 244 | —NHCH$_2$CH$_3$ | —OCH$_2$CH$_3$ | 425.3 | 2.86 |
| 245 | —NHCH$_2$CH$_3$ | —OCH(CH$_3$)$_2$ | 439.3 | 3.09 |
| 246 | —NHCH$_2$CH$_3$ | -O-Ph | 473.5 | 3.32 |
| 247 | —NHCH$_3$ | —OCH$_3$ | 397.2 | 2.47 |
| 248 | —NHCH$_3$ | —OCH$_2$CH$_3$ | 411.2 | 2.67 |
| 249 | —NHCH$_3$ | —OCH(CH$_3$)$_2$ | 425.3 | 2.93 |
| 250 | —NHCH$_3$ | -O-Ph | 459.2 | 3.11 |
| 251 | —NHCH(CH$_3$)$_2$ | —OCH$_3$ | 425.3 | 2.87 |
| 252 | —NHCH(CH$_3$)$_2$ | —OCH$_2$CH$_3$ | 439.4 | 3.07 |
| 253 | —NHCH(CH$_3$)$_2$ | —OCH(CH$_3$)$_2$ | 453.4 | 3.27 |
| 254 | —NHCH(CH$_3$)$_2$ | -O-Ph | 487.4 | 3.42 |
| 255 | —NHCH$_3$ | —NHCH$_3$ | 396.0 | 2.68 |
| 256 | —NHCH$_3$ | -HN-cyclopropyl | 422.0 | 3.09 |
| 257 | —NHCH$_2$CH$_3$ | -HN-cyclopropyl | 436.3 | 3.26 |
| 258 | —NHCH$_2$CH$_2$CH$_3$ | -HN-cyclopropyl | 450.4 | 3.49 |
| 259 | —NHCH$_2$CH$_2$CH$_3$ | —NHCH$_3$ | 424.2 | 3.16 |

-continued

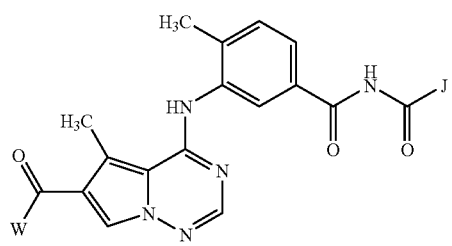

| Ex. No. | W | J | HPLC ret. time (min.) | MS (M + H)+ |
|---|---|---|---|---|
| 260 | —OCH$_2$CH$_3$ | —CH$_3$ | 396.3 | 3.63 |
| 261 | —OCH$_2$CH$_3$ | —OCH$_3$ | 412.2 | 3.56 |
| 262 | —NHCH$_2$CH$_2$CH$_3$ | —CH$_3$ | 409.2 | 2.99 |
| 263 | —NHCH$_2$CH$_2$CH$_3$ | —CH(CH$_3$)$_2$ | 437.3 | 3.31 |
| 264 | —NHCH$_2$CH$_2$CH$_3$ | —CH$_2$CH$_3$ | 423.2 | 3.16 |
| 265 | —NHCH$_2$CH$_2$CH$_3$ | cyclopropyl | 435.3 | 3.18 |
| 266 | —NHCH$_2$CH$_3$ | cyclopropyl | 421.3 | 2.92 |
| 267 | —NHCH$_2$CH$_3$ | —CH$_2$CH$_3$ | 409.3 | 2.95 |

EXAMPLES 268-284

Step A

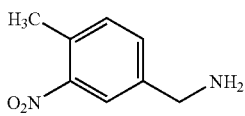

A solution of 4-methyl-3-nitrobenzyl chloride (1.09 g, 5.87 mmol) in DMF (10 mL) was added phthalimide (0.86 g, 5.87 mmol), Bu$_4$NI (50 mg) and K$_2$CO$_3$ (0.97 g) and the reaction mixture stirred rapidly for 4 h. Water (40 mL) was added dropwise and the slurry was stirred for 15 min. The solids were filtered and washed with water to give the protected amine (1.68 g, 97%).

The above solids (0.75 g) was suspended in EtOH (25 mL) and added hydrazine (0.39 mL). The reaction mixture was heated to 60° C. for 8 h then cooled. MeOH (25 mL) was added and the suspension stirred rapidly to break up the solids. The product was filtered and rinsed with MeOH (2×) to give the product (0.38 g, 90%).

Step B

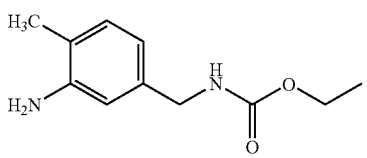

The amine (0.38 g, 2.3 mmol) was dissolved in CH$_2$Cl$_2$ (10 mL) and cooled to 0° C. and added DIPEA (0.44 mL, 2.5 mmol). Ethyl chloroformate (0.22 mL, 2.3 mmol) was added and the reaction stirred for 5 minutes followed by the addition of MeOH (0.1 mL). The mixture was concentrated to an oil and dissolved in EtOAc (30 mL) followed by washing with water, dilute aq NaHCO$_3$ and brine. The organic layer was dried over Na$_2$SO$_4$, filtered and concentrated to an oil. Purification via column chromatography (25% EtOAc/hexane) afforded the nitro product (500 mg, 92%).

The above product was dissolved in EtOH (5 mL) and EtOAc (5 mL) and added 5% Pd—C (wet) followed by evacuation and backfilling with hydrogen (3×). The mixture was stirred for 1 h and filtered to give the product (177 mg, 99%).

This amine was then coupled and elaborated in a similar fashion as outlined in Example 1 to give the examples in the Table provided below.

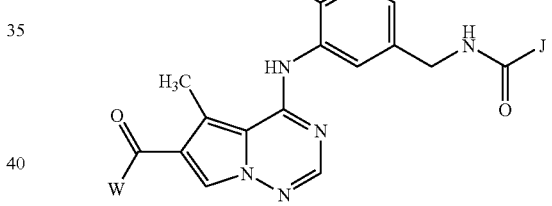

| Ex. No. | W | J | HPLC ret. time (min.) | MS (M + H)+ |
|---|---|---|---|---|
| 268 | —OCH$_2$CH$_3$ | —OCH$_2$CH$_3$ | 3.75 | 412.3 |
| 269 | —OCH$_2$CH$_3$ | phenyl | 3.88 | 444.2 |
| 270 | —OCH$_2$CH$_3$ | —CH$_3$ | 3.41 | 382.3 |
| 271 | —OCH$_2$CH$_3$ | —CH$_2$OCH$_3$ | 3.51 | 412.4 |
| 272 | —OCH$_2$CH$_3$ | —CH$_2$CH$_3$ | 3.53 | 396.4 |
| 273 | —OCH$_2$CH$_3$ | 4-cyanophenyl | 3.82 | 469.3 |
| 274 | —NHCH$_2$CH$_3$ | phenyl | 3.08 | 444.3 |

-continued

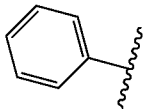

| Ex. No. | W | J | HPLC ret. time (min.) | MS (M + H)+ |
|---|---|---|---|---|
| 275 | —NHCH$_2$CH$_2$CH$_3$ | 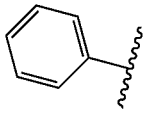 | 3.32 | 458.5 |
| 276 | —NHCH$_2$CH$_2$OH | 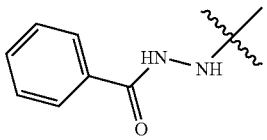 | 2.80 | 459.2 |
| 277 | —NHCH$_2$CH$_3$ | —CH$_2$OCH$_3$ | 2.52 | 411.2 |

-continued

| Ex. No. | W | J | HPLC ret. time (min.) | MS (M + H)+ |
|---|---|---|---|---|
| 278 | —NHCH$_2$CH$_2$CH$_3$ | —CH$_2$OCH$_3$ | 2.81 | 425.2 |
| 279 | —NHCH$_2$CH$_2$OH | —CH$_2$OCH$_3$ | 2.15 | 427.1 |
| 280 | —NHCH$_2$CH$_3$ | —CH$_2$CH$_3$ | 2.57 | 395.5 |
| 281 | —NHCH$_2$CH$_2$CH$_3$ | —CH$_2$CH$_3$ | 2.88 | 409.2 |
| 282 | —NHCH$_2$CH$_2$OH | —CH$_2$CH$_3$ | 2.21 | 411.5 |
| 283 | —NHCH$_2$CH$_3$ | —OCH$_2$CH$_3$ | 2.90 | 411.3 |
| 284 | —NHCH$_2$CH$_2$CH$_3$ | —OCH$_2$CH$_3$ | 3.15 | 425.3 |

EXAMPLES 285-290

The following compounds were prepared according to the procedure outlined in Example 31.

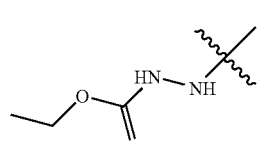

| Ex. No. | W | J | HPLC ret. time (min.) | MS (M + H)+ |
|---|---|---|---|---|
| 285 | —NHCH$_2$CH$_3$ | —NHNHCOH | 2.26 | 396.3 |
| 286 | —NHCH$_2$CH$_3$ | 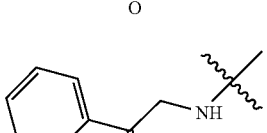 | 2.71 | 472.4 |
| 287 | —NHCH$_2$CH$_3$ | | 2.53 | 440.3 |
| 288 | —NHCH$_2$CH$_3$ | | 3.17 | 471.2 |

-continued

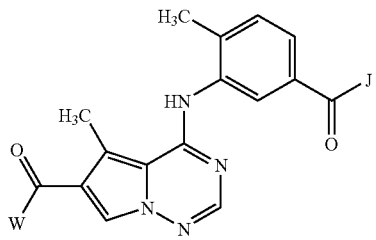

| Ex. No. | W | J | HPLC ret. time (min.) | MS (M + H)+ |
|---|---|---|---|---|
| 289 | —NHCH$_2$CH$_3$ | 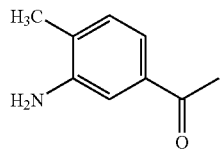 | 2.21 | 410.2 |
| 290 | —NHCH$_2$CH$_2$CH$_3$ | —NH$_2$ | 2.68 | 367.3 |

EXAMPLES 291-293

Step A

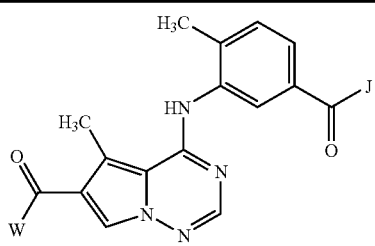

A solution of 3-nitro-4-methylacetophenone (0.4 g, 2.23 mmol) in EtOH (12 mL) was added 5% Pd—C (wet, 100 mg). The flask was evacuated and backfilled under hydrogen balloon (3×). The reaction was stirred for 3 h, filtered and concentrated to give 3-amino-4-methylacetophenone (330 mg, 99%).

Step B 3-amino-4-methylacetophenone was then coupled with 1B as in Example 1 and elaborated to the C-6 amide in an identical fashion as in Example 2 and 3 to produce the compounds listed in the below Table.

| Ex. No. | W | J | HPLC ret. time (min.) | MS (M + H)+ |
|---|---|---|---|---|
| 291 | —OCH$_2$CH$_3$ | —CH$_3$ | 3.75 | 353.3 |
| 292 | —NHCH$_2$CH$_3$ | —CH$_3$ | 2.84 | 352.3 |
| 293 | —NHCH$_2$CH$_2$CH$_3$ | —CH$_3$ | 3.08 | 366.4 |

EXAMPLE 294

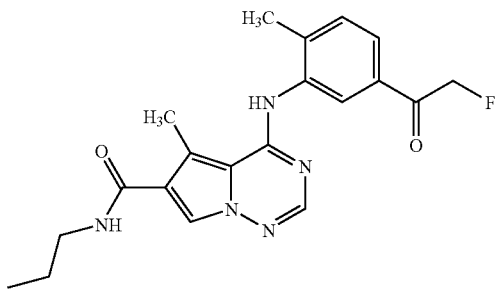

Step A:

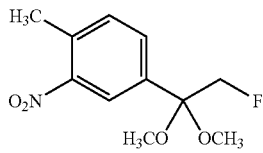

A solution of 3-nitro-4-methylacetophenone (0.1 g, 0.53 mmol) in MeOH (5 mL) was added Accufluor and the solution heated at reflux for 18 h. The reaction was cooled, concentrated and suspended in CH$_2$Cl$_2$. The solution was filtered and the organic filtrates were washed with sat. NaHCO$_3$ and water. The organic layer was dried over Na$_2$SO$_4$, filtered and concentrated to an oil which was purified via column chromatography (10% the 25% EtOAc/hexane) to furnish the above product (70 mg, 54%).

Step B: Title Compound

This product was reduced to the amine in an identical fashion as the above examples to furnish 60 mg (98%) which was coupled directly with the intermediate obtained in Step A in the preparation of Example 237, to afford 73 mg of the crude ketal which was treated with 3N HCl (0.1 mL) in acetone (3 mL) for 2 d. The reaction was neutralized with sat aq. NaHCO$_3$ and diluted with water (3 mL). The solids were filtered to give 55.3 mg of the title compound.

EXAMPLE 295

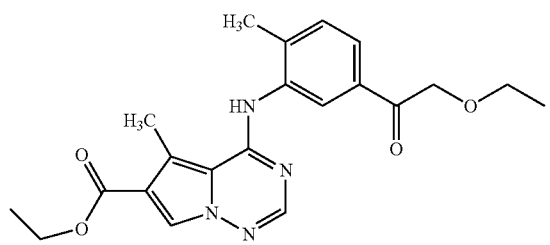

Step A:

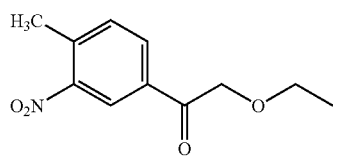

A solution of 3-nitro-4-methylbenzoyl chloride (1.6 g) in THF (50 mL) and MeCN (50 mL) was added trimethylsilyl-diazomethane (5 mL, 2M in hexanes) and TEA (1.4 mL) at 0° C. The reaction mixture was stirred at 0° C. for 24 h. The volatiles were removed in vacuo to give 3.3 g of a crude yellow solid. A portion was purified via column chromatography (25% EtOAc/hexane).

The above diazoketone (44 mg, 0.22 mmol) was dissolved in CH$_2$Cl$_2$ (1 mL) and EtOH (0.09 mL) and added BF$_3$OEt$_2$ (0.006 mL) was added. The mixture was stirred for 90 min and a second addition of BF$_3$OEt$_2$ (0.005 mL) was made. The reaction mixture was stirred for 16 h and purified directly through a silica gel plug to afford the ketone (42.1 mg, 88%).

Step B:

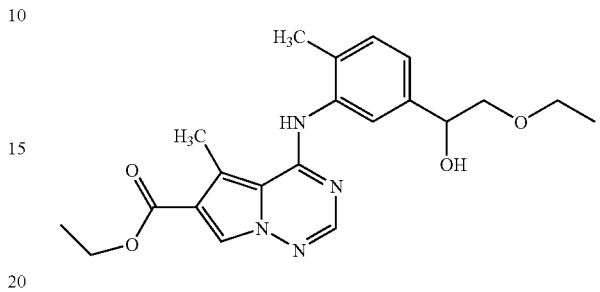

The ketone was reduced to the amino-alcohol in an identical fashion as the above examples and coupled to the chloropyrrolotriazine as in Example 1 to give the alcohol (58 mg).

Step C: Title Compound

The alcohol (56 mg, 0.14 mmol) was dissolved in CH$_2$Cl$_2$ and added PCC (36.3 mg, 0.17 mmol). The reaction was stirred at rt for 24 h, filtered through celite and purified via column chromatography (25% EtOAc/hexane) to give the ketone (44 mg, 79%).

EXAMPLES 296-305

Examples 296-305 were prepared according to the procedure outlined in Example 31.

| Ex. | Structure | MW | HPLC ret. t (min) | MS (MH+) |
|---|---|---|---|---|
| 296 | 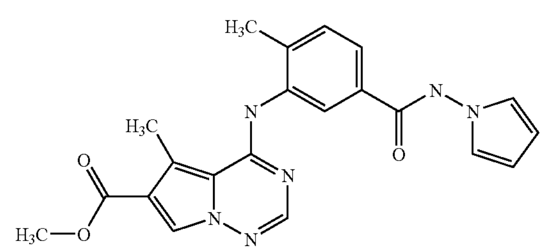 | 404.43 | 2.96 | 405.2 |
| 297 | 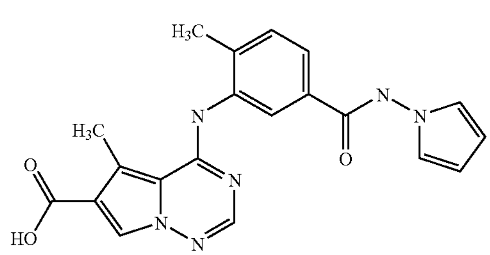 | 390.4 | 2.56 | 391.2 |

-continued

| Ex. | Structure | MW | HPLC ret. t (min) | MS (MH+) |
|---|---|---|---|---|
| 298 | 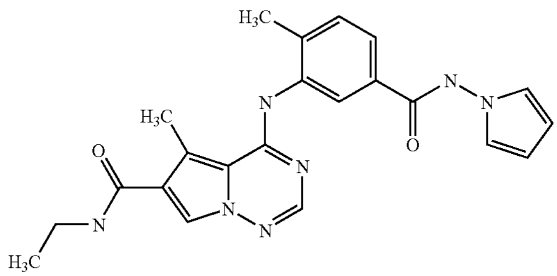 | 417.47 | 2.37 | 418.3 |
| 299 | 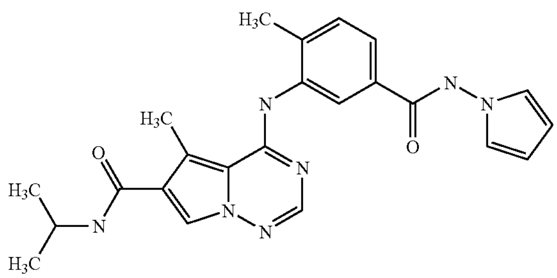 | 431.5 | 2.6 | 432.3 |
| 300 | Chiral | 493.57 | 3.07 | 494.3 |
| 301 | 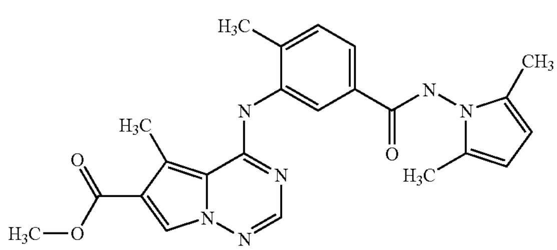 | 432.49 | 3.17 | 433.2 |
| 302 | 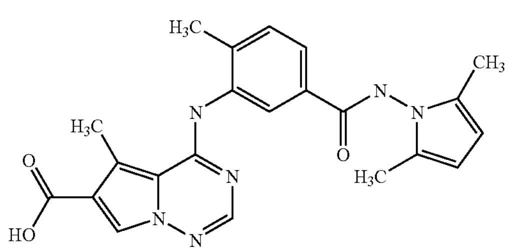 | 418.46 | 2.75 | 419.3 |

| Ex. | Structure | | MW | HPLC ret. t (min) | MS (MH+) |
|---|---|---|---|---|---|
| 303 | 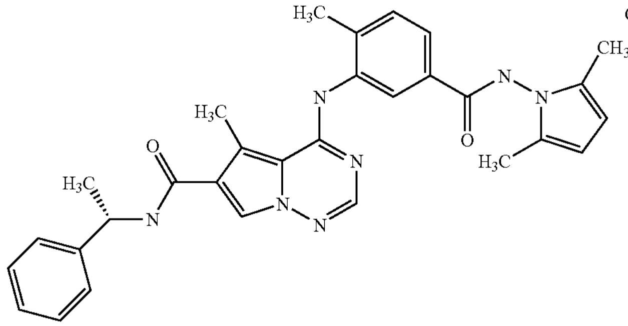 | Chiral | 521.63 | 3.22 | 522.2 |
| 304 | 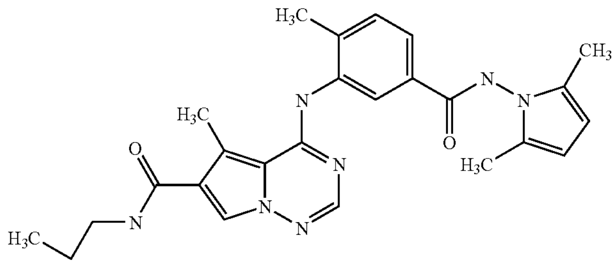 | | 459.56 | 2.84 | 460.3 |
| 305 | 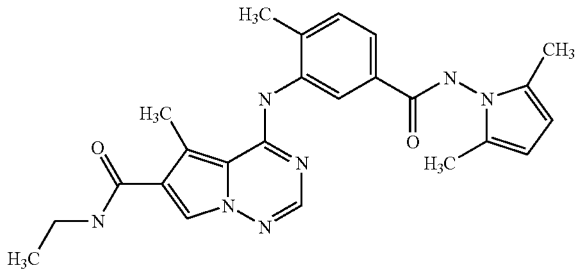 | | 445.53 | 2.62 | 446.4 |
EXAMPLES 306-307
Examples 306-307 were prepared following the same procedure described for Example 3.
| Ex. | Structure | MW | HPLC ret. t (min) | MS (MH+) |
|---|---|---|---|---|
| 306 | 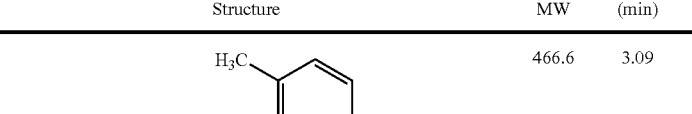 | 466.6 | 3.09 | 467 |

-continued

| Ex. | Structure | MW | HPLC ret. t (min) | MS (MH+) |
|---|---|---|---|---|
| 307 | 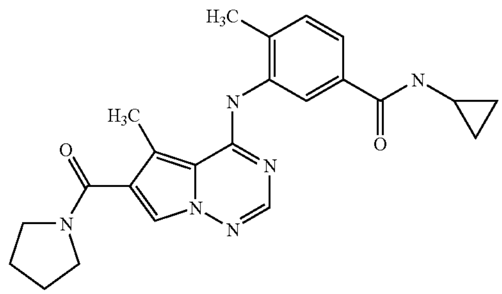 | 416.5 | 2.40 | 417 |

EXAMPLES 308-311

Examples 308-311 were prepared following procedures similar to that described in Example 48.

| Ex. | Structure | MW | HPLC ret. T (min) | MS (MH+) |
|---|---|---|---|---|
| 308 | 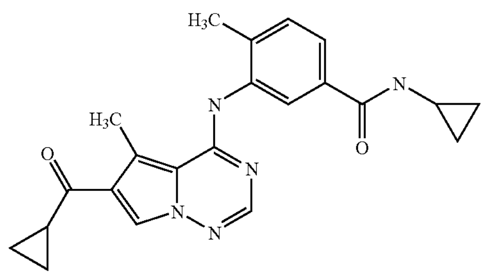 | 389.5 | 2.63 | 390 |
| 309 | 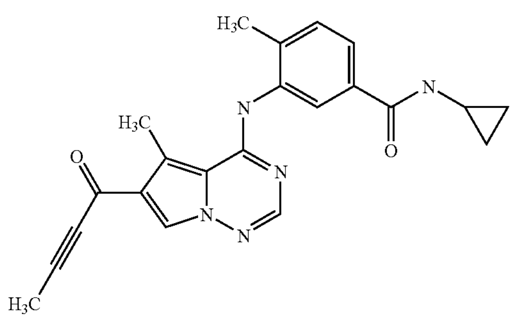 | 387.4 | 3.00 | 388 |
| 310 | 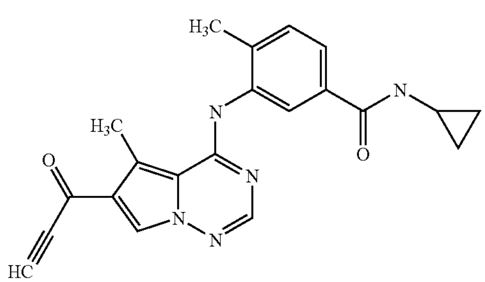 | 373.4 | 2.89 | 374 |

| Ex. | Structure | MW | HPLC ret. T (min) | MS (MH+) |
|---|---|---|---|---|
| 311 | 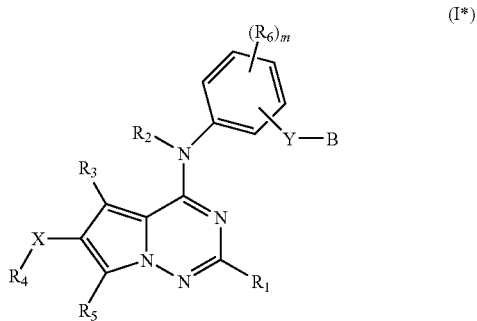 | 391.5 | 3.15 | 392 |

We claim:

1. A compound having the formula (I*):

$$\text{(I*)}$$

an enantiomer, diastereomer, or pharmaceutically-acceptable salts thereof wherein X is selected from —O—, —OC(=O)—, —S—, —S(=O)—, —SO$_2$—, —C(=O)—, —CO$_2$—, —NR$_8$—, —NR$_8$C(=O)—, —NR$_8$C(=O)NR$_9$—, —NR$_8$CO$_2$—, —NR$_8$SO$_2$—, —NR$_8$SO$_2$NR$_9$—, —SO$_2$NR$_8$—, —C(=O)NR$_8$—, halogen, nitro, and cyano, or X is absent;

Y is —NR$_{10}$SO$_2$ or —SO$_2$NR$_{10}$;

B is optionally-substituted cycloalkyl, heterocyclo, or heteroaryl; or aryl substituted with one R$_{11}$ and zero to two R$_{12}$;

R$_1$ and R$_5$ are independently selected from hydrogen, alkyl, substituted alkyl, —OR$_{14}$, —SR$_{14}$, —OC(=O)R$_{14}$, —CO$_2$R$_{14}$, —C(=O)NR$_{14}$R$_{14a}$, —NR$_{14}$R$_{14a}$, —S(=O)R$_{14}$, —SO$_2$R$_{14}$, —SO$_2$NR$_{14}$R$_{14a}$, —NR$_{14}$SO$_2$NR$_{14a}$R$_{14b}$, —NR$_{14a}$SO$_2$R$_{14}$, —NR$_{14}$C(=O)R$_{14a}$, —NR$_{14}$CO$_2$R$_{14a}$, —NR$_{14}$C(=O)NR$_{14a}$R$_{14b}$, halogen, nitro, and cyano;

R$_2$ is hydrogen or C$_{1-4}$alkyl;

R$_3$ is hydrogen, methyl, perfluoromethyl, methoxy, halogen, cyano, NH$_2$, or NH(CH$_3$);

R$_4$ is selected from:
a) hydrogen, provided that R$_4$ is not hydrogen if X is —S(=O)—, —SO$_2$—, —NR$_8$CO$_2$—, or —NR$_8$SO$_2$—;
b) alkyl, alkenyl, and alkynyl optionally substituted with keto and/or one to four R$_{17}$;
c) aryl and heteroaryl optionally substituted with one to three R$_{16}$; and
d) heterocyclo and cycloalkyl optionally substituted with keto and/or one to three R$_{16}$; or
e) R$_4$ is absent if X is halogen, nitro, or cyano;

R$_6$ is attached to any available carbon atom of phenyl ring A and at each occurrence is independently selected from alkyl, halogen, trifluoromethoxy, trifluoromethyl, hydroxy, alkoxy, alkanoyl, alkanoyloxy, thiol, alkylthio, ureido, nitro, cyano, carboxy, carboxyalkyl, carbamyl, alkoxycarbonyl, alkylthiono, arylthiono, arylsulfonylamine, alkylsulfonylamine, sulfonic acid, alkysulfonyl, sulfonamido, phenyl, benzyl, aryloxy, and benzyloxy, wherein each R$_6$ group in turn may be further substituted by one to two R$_{18}$;

R$_8$ and R$_9$ are independently selected from hydrogen, alkyl, substituted alkyl, aryl, cycloalkyl, heterocyclo, and heteroaryl;

R$_{10}$ and R$_{10a}$ are independently selected from hydrogen, alkyl, substituted alkyl, alkoxy, and aryl;

R$_{11}$ is selected from optionally-substituted cycloalkyl, heterocyclo, and heteroaryl;

R$_{12}$ is selected from alkyl, R$_{17}$, and C$_{1-4}$alkyl substituted with keto (=O) and/or one to three R$_{17}$;

R$_{13}$ and R$_{13a}$ are selected from hydrogen, alkyl, and substituted alkyl;

R$_{14}$, R$_{14a}$ and R$_{14b}$ are independently selected from hydrogen, alkyl, substituted alkyl, aryl, cycloalkyl, heterocyclo, and heteroaryl, except when R$_{14}$ is joined to a sulphonyl group as in —S(=O)R$_{14}$, —SO$_2$R$_{14}$, and —NR$_{14a}$SO$_2$R$_{14}$, then R$_{14}$ is not hydrogen;

R$_{16}$ is selected from alkyl, R$_{17}$, and C$_{1-4}$alkyl substituted with keto (=O) and/or one to three R$_{17}$;

R$_{17}$ is selected from halogen, haloalkyl, haloalkoxy, nitro, cyano, —SR$_{23}$, —OR$_{23}$, —NR$_{23}$R$_{24}$, —NR$_{23}$SO$_2$R$_{25}$, —SO$_2$R$_{25}$, —SO$_2$NR$_{23}$R$_{24}$, —CO$_2$R$_{23}$, —C(=O)R$_{23}$, —C(=O)NR$_{23}$R$_{24}$, —OC(=O)R$_{23}$, —OC(=O)NR$_{23}$R$_{24}$, —NR$_{23}$C (=O)R$_{24}$, —NR$_{23}$CO$_2$R$_{24}$, aryl or heteroaryl optionally substituted with one to three R$_{26}$; or cycloalkyl or heterocyclo optionally substituted with keto(=O) and/or one to three R$_{26}$;

R$_{18}$ and R$_{26}$ are independently selected from C$_{1-6}$alkyl, C$_{2-6}$alkenyl, halogen, haloalkyl, haloalkoxy, cyano, nitro, amino, C$_{1-4}$alkylamino, aminoC$_{1-4}$alkyl, hydroxy, hydroxyC$_{1-4}$alkyl, alkoxy, C$_{1-4}$alkylthio, phenyl, benzyl, phenyloxy, and benzyloxy;

R$_{23}$ and R$_{24}$ are each independently selected from hydrogen, alkyl, alkenyl, substituted alkyl, substituted alkenyl, aryl, cycloalkyl, heteroaryl, and heterocyclo;

$R_{25}$ is selected from alkyl, substituted alkyl, aryl, heteroaryl, cyclo alkyl and heterocyclo; and m is 0, 1, 2 or 3.

2. A compound according to claim 1, or an enantiomer, diastereomer, or pharmaceutically-acceptable salt-thereof, in which:

B is a $C_{3-7}$cycloalkyl optionally substituted with one to two $R_7$, a five membered heteroaryl optionally substituted with one to two $R_7$, a five or six membered heterocyclo optionally substituted with one to two $R_7$, aryl substituted with one $R_{11}$ and zero to two $R_{12}$;

$R_7$ is attached to any available carbon or nitrogen atom of ring B and at each occurrence is independently selected from keto (=O), alkyl, substituted alkyl, halogen, haloalkoxy, ureido, cyano, —$SR_{20}$, —$OR_{20}$, —$NR_{20}R_{21}$, —$NR_{20}SO_2R_{21}$, —$SO_2R_{19}$, —$SO_2NR_{20}R_{21}$, —$CO_2R_{20}$, —$C(=O)R_{20}$, —$C(=O)NR_{20}R_{21}$, —$OC(=O)R_{20}$, —$OC(=O)NR_{20}R_{21}$, —$NR_{20}C(=O)R_{21}$, —$NR_{20}CO_2R_{21}$, aryl, cycloalkyl, heterocycle, and heteroaryl; and/or when B is cycloalkyl, two $R_7$ groups may join to form an optionally-substituted carbon-carbon bridge of three to four carbon atoms, or two $R_7$ groups may join to form a fused carbocyclic, heterocyclic or heteroaryl ring, said fused ring being in turn optionally substituted with one to three $R_{22}$;

$R_{20}$ and $R_{21}$ are selected from hydrogen, alkyl, alkenyl, substituted alkyl, substituted alkenyl, phenyl, $C_{3-7}$cycloalkyl, and five-to-six membered heterocyclo or heteroaryl; and $R_{12}$ and $R_{22}$ are independently selected from $C_{1-6}$alkyl, $C_{2-6}$alkenyl, halogen, haloalkyl, haloalkoxy, cyano, nitro, amino, $C_{1-4}$alkylamino, amino$C_{1-4}$alkyl, hydroxy, hydroxy$C_{1-4}$alkyl, alkoxy, alkylthio, phenyl, benzyl, phenyloxy, and benzyloxy.

3. A compound according to claim 1, having the formula (Ia),

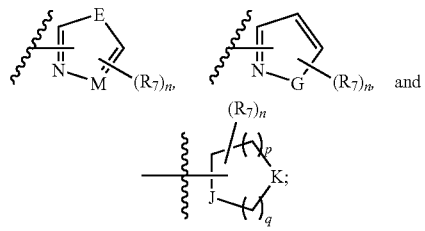

or an enantiomer, diastereomer, or pharmaceutically-acceptable salt-thereof, wherein:

$R_3$ is methyl, —$CF_3$, or —$OCF_3$;

X is —C(=O)—, —$NR_8C(=O)$—, or —$C(=O)NR_8$—, wherein $R_8$ is hydrogen or $C_{1-4}$alkyl;

Y is —$NHSO_2$—;

R4 is hydrogen, $C_{2-6}$alkyl, $C_{1-4}$alkyl optionally substituted with one to three $R_{17}$, cycloalkyl or heterocycle optionally-substituted with keto (=O) and/or one to three $R_{16}$; or aryl or heteroaryl optionally substituted with one to three $R_{16}$;

$R_{6a}$ and $R_{6b}$ are independently selected from hydrogen, $C_{1-6}$alkyl, substituted $C_{1-4}$alkyl, halogen, trifluoromethoxy, trifluoromethyl, —$OR_{27}$, —C(=O)alkyl, —OC(=O)alkyl, —$NR_{27}R_{28}$, —$SR_{27}$, —$NO_2$, —CN, —$CO_2R_{27}$, —$CONH_2$, —$SO_3H$, —S(=O)alkyl, —S(=O)aryl, —$NHSO_2$-aryl-$R_{27}$, —$SO_2NHR_{27}$, —$CONHR_{27}$, and —$NHC(=O)NHR_{27}$;

$R_{16}$ is selected from $C_{1-4}$alkyl, $R_{17}$, and $C_{1-4}$alkyl substituted with keto (=O) and/or one to two $R_{17}$;

$R_{17}$ is selected from halogen, hydroxy, $C_{1-4}$alkoxy, trifluoromethyl, trifluoromethoxy, cyano, nitro, phenyl, benzyl, phenyloxy, benzyloxy, $NH_2$, $NH(C_{1-4}$alkyl), $N(C_{1-4}$alkyl$)_2$, $C_{3-7}$cycloalkyl, or five or six membered heteroaryl or heterocycle; and $R_{27}$ and $R_{28}$ are selected from hydrogen, $C_{1-4}$alkyl, phenyl, $C_{3-7}$cycloalkyl, and five-to-six membered heterocyclo or heteroaryl.

4. A compound according to claim 1, or an enantiomer, diastereomer, or pharmaceutically-acceptable salt-thereof, wherein:

ring B is phenyl substituted with heterocycle and zero to one $R_{12}$, or is a cycloalkyl, heteroaryl, or heterocyclo ring selected from:

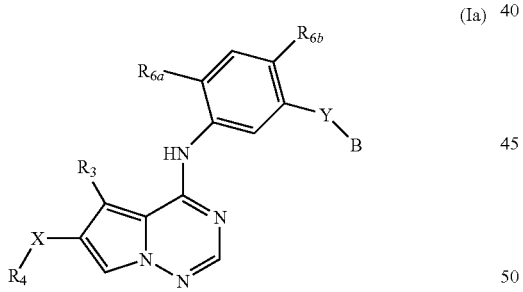

wherein E, G, J and K are selected from O, S, NH and $CH_2$, provided that when q is 0, then J and K are not simultaneously selected from O and S; and M is N or CH; wherein each hydrogen atom of E, G, J, K and M may optionally be replaced with an $R_7$ group;

$R_7$ and $R_{12}$ are independently selected from $C_{1-6}$alkyl, substituted $C_{1-4}$alkyl, halogen, trifluoromethoxy, trifluoromethyl, hydroxy, —$C_{1-4}$alkoxy, —C(=O)alkyl, —OC(=O)alkyl, $NH_2$, $NH(C_{1-4}$alkyl), $N(C_{1-4}$alkyl$)_2$, —CN, —$CO_2$alkyl, —$CONH_2$, —$CONH(CH_3)$, —$CON(CH_3)_2$, phenyl, benzyl, $C_{3-7}$ cycloalkyl, and five-to-six membered heterocyclo or heteroaryl;

n is 0, 1 or 2; and p and q are selected from 0, 1, 2, 3 and 4, provided that p and q taken together are not greater than 4.

5. A compound according to claim 1, or an enantiomer, diastereomer, or pharmaceutically-acceptable salt-thereof, in which $R_1$ and $R_5$ are independently hydrogen or $CH_3$.

6. A compound according to claim 1, or an enantiomer, diastereomer, or pharmaceutically-acceptable salt-thereof, in which $R_2$ is hydrogen.

7. A compound according to claim 1, or an enantiomer, diastereomer, or pharmaceutically-acceptable salt-thereof, in which $R_3$ is methyl, —$CF_3$, or —$OCF_3$.

8. A compound according to claim 1, or an enantiomer, diastereomer, or pharmaceutically-acceptable salt-thereof, in which X is —C(=O)— or —C(=O)NH—.

9. A compound according to claim 1, or an enantiomer, diastereomer, or Pharmaceutically-acceptable salt-thereof, which X is —C(=O)NH— and $R_4$ is $C_{2-6}$alkyl, optionally-substituted benzyl, or a heterocyclic or heteroaryl ring selected from diazepinyl, morpholinyl, piperidinyl, and pyrrolidinyl, said heterocycle being optionally substituted with one to two of $C_{1-4}$alkyl, hydroxy, $C_{1-4}$alkoxy, phenyl, and/or benzyl.

10. A compound according to claim 1, or an enantiomer, diastereomer, or Pharmaceutically-acceptable salt-thereof, in which X is —C(=O)— and $R_4$ is phenyl, pyridyl, pyrimidinyl, or pyrazinyl optionally-substituted with one to two of $C_{1-4}$alkyl, halogen, hydroxy, $C_{1-4}$alkoxy, trifluoromethyl, trifluoromethoxy, cyano, nitro, phenyl, benzyl, phenyloxy, benzyloxy, $NH_2$, $NH(C_{1-4}alkyl)$, $N(C_{1-4}alkyl)_2$ and/or a $C_{1-4}$alkyl substituted with one to two of halogen, hydroxy, $C_{1-4}$alkoxy, trifluoromethyl, trifluoromethoxy, cyano, nitro, phenyl, benzyl, phenyloxy, benzyloxy, $NH_2$, $NH(C_{1-4}alkyl)$, and/or $N(C_{1-4}alkyl)_2$.

11. A compound according to claim 1, or an enantiomer, diastereomer, or pharmaceutically-acceptable salt-thereof, in which B is cyclopropyl or cyclobutyl optionally substituted with one to two $R_7$, phenyl substituted with a five or six membered heterocycle and zero to two $R_{12}$, or B is selected from one of:

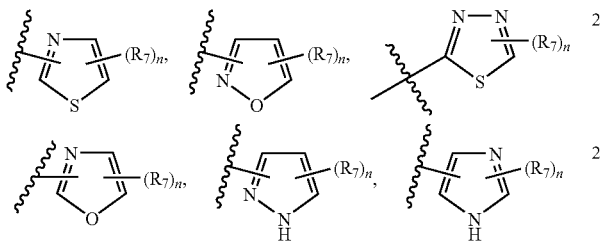

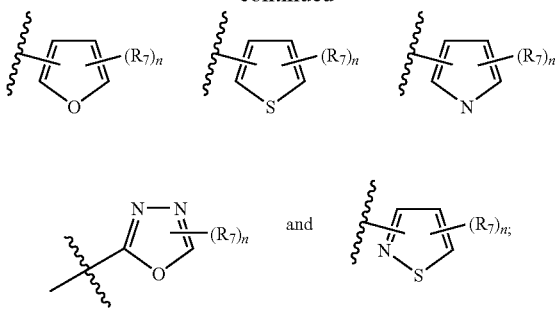

$R_7$ and $R_{12}$ are independently selected from $C_{1-4}$alkyl, trifluoromethyl, trifluoromethoxy, halogen, cyano, amino, $C_{1-4}$alkylalmino, hydroxy, $C_{1-4}$alkoxy, phenyl, benzyl, phenyloxy, and benzyloxy; and n is 0, 1 or 2.

12. A pharmaceutical composition comprising at least one compound according to claim 1 and a pharmaceutically-acceptable carrier or diluent.

* * * * *

UNITED STATES PATENT AND TRADEMARK OFFICE
CERTIFICATE OF CORRECTION

PATENT NO. : 7,759,343 B2  Page 1 of 2
APPLICATION NO. : 12/259483
DATED : July 20, 2010
INVENTOR(S) : Alaric Dyckman et al.

It is certified that error appears in the above-identified patent and that said Letters Patent is hereby corrected as shown below:

On the Title Page:

Related U.S. Application Data:

Item (62), after "Division", insert -- of application No. 11/585,598, filed on Oct. 24, 2006, now U.S. Pat. No. 7,462,616, which is a Division --.

Item (56), References Cited, under OTHER PUBLICATIONS:

Column 2, Wolft, Manfred E. reference, change "Wolft" to -- Wolff --.

The reference should read:

-- Wolff, Manfred E. "Burger's Medicinal Chemistry, 5ed, Part 1", John Wiley & Sons, 1995, pp. 975-977.* --.

Column 2, Banker, G.S. et al. reference, change "Pharmaceutices" to -- Pharmaceutics --.

The reference should read:

-- Banker, G.S. et al, "Modern Pharmaceutics, 3ed.", Marcel Dekker, New York. 1996, p. 596.* --.

In the Specification:

Column 1, line 5, after "This application", insert -- is a Division of application No. of 11/585,598, filed on Oct. 24, 2006, now U.S. Pat. No. 7,462,616, which is a Division of application No. 10/420,399, filed on Apr. 22, 2003, now Pat. No. 7,160,883, which claims --.

Signed and Sealed this
Twenty-seventh Day of December, 2011

David J. Kappos
*Director of the United States Patent and Trademark Office*

CERTIFICATE OF CORRECTION (continued)
U.S. Pat. No. 7,759,343 B2

In the Claims:

Claim 1:

Column 155, line 45, change "—$NR_{10}SO_2$ or —$SO_2NR_{10}$" to -- —$NR_{10}SO_2$— or —$SO_2NR_{10}$— --.

Claim 3:

Column 157, line 59, change "R4" to -- $R_4$ --.

Claim 9:

Column 158, line 61, change "Pharmaceutically" to -- pharmaceutically --.

Column 158, line 61, after "salt-thereof,", insert -- in --.

Claim 10:

Column 159, line 2, change "Pharmaceutically" to -- pharmaceutically --.